US007015235B2

United States Patent
Goulet et al.

(10) Patent No.: US 7,015,235 B2
(45) Date of Patent: Mar. 21, 2006

(54) ACYLATED PIPERIDINE DERIVATIVES AS MELANOCORTIN-4 RECEPTOR AGONISTS

(75) Inventors: Mark T. Goulet, Westfield, NJ (US); Ravi P. Nargund, East Brunswick, NJ (US); Iyassu K. Sebhat, New York, NY (US); Feroze Ujjainwalla, Scotch Plains, NJ (US); Thomas F. Walsh, Watchung, NJ (US); Daniel Warner, Stoneham, MA (US); Zhixiong Ye, Princeton, NJ (US); Jonathan R. Young, Kendall Park, NJ (US); Raman K. Bakshi, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 45 days.

(21) Appl. No.: 10/468,515

(22) PCT Filed: Feb. 25, 2002

(86) PCT No.: PCT/US02/05623

§ 371 (c)(1),
(2), (4) Date: Aug. 19, 2003

(87) PCT Pub. No.: WO02/068387

PCT Pub. Date: Sep. 6, 2002

(65) Prior Publication Data

US 2004/0097546 A1 May 20, 2004

Related U.S. Application Data

(60) Provisional application No. 60/300,572, filed on Jun. 22, 2001, provisional application No. 60/272,258, filed on Feb. 28, 2001.

(51) Int. Cl.
*A61K 31/445* (2006.01)
*C07D 211/06* (2006.01)

(52) U.S. Cl. ................ 514/330; 514/317; 514/323; 546/208; 546/212; 546/224; 546/226

(58) Field of Classification Search ............... 514/317, 514/323; 546/208, 212, 224
See application file for complete search history.

(56) References Cited

U.S. PATENT DOCUMENTS

6,350,760 B1 * 2/2002 Bakshi et al. ............. 514/323
6,511,994 B1 * 1/2003 Kim et al. ................. 514/319
6,818,658 B1 * 11/2004 Ujjainwalla et al. ....... 514/326

FOREIGN PATENT DOCUMENTS

| WO | WO 99/09984 | 3/1999 |
|---|---|---|
| WO | WO 01/58891 | 8/2001 |
| WO | WO 02/067869 | 9/2002 |

OTHER PUBLICATIONS

Tsubouchi et al. "Preparation of 2,3-dihydro . . . " CA 140:357387 (2004).*
Lendaris et al. "Reach through claims . . . " Intellectual property update, vol. 4, No. 5, (2004).*
Baker Botts "Reach through claims" Attorneys practice profile new and events (2002).*
Uckert et al., Expert Opin. Investig. Drugs (2003), vol. 12(9), pp. 1521-1533, "Current and future trends in the oral pharmacotherapy of male erectile dysfunction".

* cited by examiner

*Primary Examiner*—Celia Chang
(74) *Attorney, Agent, or Firm*—Baerbel R. Brown; Melvin Winokur

(57) ABSTRACT

Certain novel 4-substituted N-acylated piperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

12 Claims, No Drawings

ACYLATED PIPERIDINE DERIVATIVES AS MELANOCORTIN-4 RECEPTOR AGONISTS

CROSS-REFERENCE TO RELATED APPLICATIONS

This application is a U.S. National Phase application under 35 U.S.C. §371 of PCT Application Ser. No. PCT/US02/05623, filed Feb. 25, 2002, which claims priority under 35 U.S.C. §119 from U.S. Provisional Application Nos. 60/300,572, filed Jun. 22, 2001, and 60/272,258, filed Feb. 28, 2001.

FIELD OF THE INVENTION

The present invention relates to acylated piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," *Brain Research*, 80: 302–306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., *Cell*, 88: 131–141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," *Biochem. Biophys. Res. Commun.*, 245: 90–93 (1998)). MC-5R is expressed in many tissues, including white fat, placenta and exocrine glands. A low level of expression is also observed in the brain. MC-5R knockout mice reveal reduced sebaceous gland lipid production (Chen et al., *Cell*, 91: 789–798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387–390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," *Exp. Opin. Ther. Patents* 9: 1689–1696 (1999)). Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," *Life Sci.*, 62: 309–318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. Tadalafil or IC-351 (ICOS Corp.) is claimed to have greater selectivity for PDE-V over PDE-VI than sildenafil. Other PDE-V inhibitors include vardenafil from Bayer, M-54033 and M-54018 from Mochida Pharmaceutical Co., and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives*, 9: 572–575 (1996); "Oral Pharmacotherapy in Erectile Dysfunction," *Current Opinion in Urology*, 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389–393 (1998); *Fifteenth American Peptide Symposium*, Jun. 14–19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology*, 56: 641–646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine and piperidine derivatives have been disclosed in WO 99/64002 (16 Dec. 1999); WO 00/74679 (14 Dec. 2000); WO 01/70708 (27 Sep. 2001); WO 01/70337 (27 Sep. 2001); and WO 01/91752 (6 Dec. 2001) as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated piperidine derivatives which are melanocortin receptor agonists and thereby useful to treat obesity, diabetes, male sexual dysfunction, and female sexual dysfunction.

It is another object of the present invention to provide acylated piperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a subject in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a subject in need thereof.

It is another object of the present invention to provide methods for the treatment of erectile dysfunction by administering the compounds and pharmaceutical compositions of the present invention to a subject in need thereof.

These and other objects will become readily apparent from the detailed description that follows.

SUMMARY OF THE INVENTION

The present invention relates to novel 4-substituted N-acylated piperidines of structural formula I:

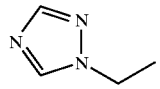

These acylated piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin receptor in a subject in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to treat or prevent the condition.

The present invention also relates to methods for treating or preventing diabetes by administering the compounds of the present invention in combination with a therapeutically effective amount of another agent known to be useful to treat or prevent the condition.

DETAILED DESCRIPTION OF THE INVENTION

The present invention relates to 4-substituted N-acylated piperidine derivatives useful as melanocortin receptor agonists, in particular, as selective MC-4R agonists. Compounds of the present invention are described by structural formula I:

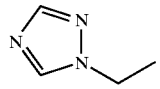

or a pharmaceutically acceptable salt thereof;

wherein
r is 1 or 2;
s is 0, 1, or 2;
n is 0, 1, or 2;
p is 0, 1, or 2;
$R^1$ is selected from the group consisting of
  hydrogen,
  amidino,
  $C_{1-4}$ alkyliminoyl,
  $C_{1-10}$ alkyl,
  $(CH_2)_n$—$C_{3-7}$ cycloalkyl,
  $(CH_2)_n$-phenyl,
  $(CH_2)_n$-naphthyl, and
  $(CH_2)_n$-heteroaryl wherein heteroaryl is selected from the group consisting of
    (1) pyridinyl,
    (2) furyl,
    (3) thienyl,
    (4) pyrrolyl,
    (5) oxazolyl,
    (6) thiazolyl,
    (7) imidazolyl,
    (8) pyrazolyl,
    (9) isoxazolyl,
    (10) isothiazolyl,
    (11) pyrimidinyl,
    (12) pyrazinyl,
    (13) pyridazinyl,
    (14) quinolyl,
    (15) isoquinolyl,
    (16) benzimidazolyl,
    (17) benzofuryl,
    (18) benzothienyl,
    (19) indolyl,
    (20) benzthiazolyl, and
    (21) benzoxazolyl;

in which phenyl, naphthyl, and heteroaryl are unsubstituted or substituted with one to three groups independently selected from $R^3$; and alkyl and cycloalkyl are unsubstituted or substituted with one to three groups independently selected from $R^3$ and oxo;
$R^2$ is selected from the group consisting of
  phenyl,
  naphthyl, and
  heteroaryl wherein heteroaryl is selected from the group consisting of
    (1) pyridinyl,
    (2) furyl,
    (3) thienyl,
    (4) pyrrolyl,
    (5) oxazolyl,
    (6) thiazolyl,
    (7) imidazolyl,
    (8) pyrazolyl,
    (9) isoxazolyl,
    (10) isothiazolyl,
    (11) pyrimidinyl,
    (12) pyrazinyl,
    (13) pyridazinyl,
    (14) quinolyl,
    (15) isoquinolyl,
    (16) benzimidazolyl,
    (17) benzofuryl,
    (18) benzothienyl,

(19) indolyl,
(20) benzthiazolyl, and
(21) benzoxazolyl;

in which phenyl, naphthyl, and heteroaryl are unsubstituted or substituted with one to three groups independently selected from $R^3$;

$R^3$ is selected from the group consisting of
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
$OR^4$,
$(CH_2)_nN(R^4)_2$,
$(CH_2)_nC\equiv N$,
$CO_2R^4$,
$C(R^4)(R^4)N(R^4)_2$,
$NO_2$,
$(CH_2)_nNR^4SO_2R^4$,
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$,
$(CH_2)_nNR^4C(O)R^4$,
$(CH_2)_nNR^4CO_2R^4$,
$CF_3$,
$CH_2CF_3$,
$OCF_3$, and
$OCH_2CF_3$;

in which heteroaryl is as defined above; phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and $(CH_2)_n$ is unsubstituted or substituted with one to two groups independently selected from halogen, hydroxy, and $C_{1-4}$ alkyl;

each $R^4$ is independently selected from the group consisting of
hydrogen,
$C_{1-6}$ alkyl,
$(CH_2)_n$-phenyl,
$(CH_2)_n$-naphthyl, and
$(CH_2)_nC_{3-7}$ cycloalkyl;

wherein cycloalkyl is unsubstituted or substituted with one to three groups independently selected from halogen, $C_{1-4}$ alkyl, and $C_{1-4}$ alkoxy; or two $R^4$ groups together with the atom to which they are attached form a 4- to 8-membered mono- or bicyclic ring system optionally containing an additional heteroatom selected from O, S, and $NC_{1-4}$ alkyl;

each $R^5$ is independently selected from the group consisting of
hydrogen,
$C_{1-8}$ alkyl,
$(CH_2)_n$-phenyl,
$(CH_2)_n$-naphthyl,
$(CH_2)_n$-heteroaryl, and
$(CH_2)_nC_{3-7}$ cycloalkyl;

wherein heteroaryl is as defined above; phenyl, naphthyl, and heteroaryl are unsubstituted or substituted with one to three groups independently selected from $R^3$; and alkyl, cycloalkyl, and $(CH_2)_n$ are unsubstituted or substituted with one to three groups independently selected from $R^3$ and oxo; or two $R^5$ groups together with the atom to which they are attached form a 5- to 8-membered mono- or bicyclic ring system optionally containing an additional heteroatom selected from O, S, and $NC_{1-4}$ alkyl;

X is selected from the group consisting of
$C_{1-8}$ alkyl,
$(CH_2)_nC_{3-8}$ cycloalkyl,
$(CH_2)_n$-phenyl,
$(CH_2)_n$-naphthyl,
$(CH_2)_n$-heteroaryl,
$(CH_2)_n$heterocyclyl,
$(CH_2)_nC\equiv N$,
$(CH_2)_nCON(R^5R^5)$,
$(CH_2)_nCO_2R^5$,
$(CH_2)_nCOR^5$,
$(CH_2)_nNR^5C(O)R^5$,
$(CH_2)_nNR^5CO_2R^5$,
$(CH_2)_nNR^5C(O)N(R^5)_2$,
$(CH_2)_nNR^5SO_2R^5$,
$(CH_2)_nS(O)_pR^5$,
$(CH_2)_nSO_2N(R^5)(R^5)$,
$(CH_2)_nOR^5$,
$(CH_2)_nOC(O)R^5$,
$(CH_2)_nOC(O)OR^5$,
$(CH_2)_nOC(O)N(R^5)_2$,
$(CH_2)_nN(R^5)(R^5)$, and
$(CH_2)_nNR^5SO_2N(R^5)(R^5)$;

wherein heteroaryl is as defined above; phenyl, naphthyl, and heteroaryl are unsubstituted or substituted with one to three groups independently selected from $R^3$; and alkyl, $(CH_2)_n$, cycloalkyl, and heterocyclyl are unsubstituted or substituted with one to three groups independently selected from $R^3$ and oxo;

Y is selected from the group consisting of
hydrogen,
$C_{1-8}$ alkyl,
$C_{2-6}$ alkenyl,
$(CH_2)_nC_{3-8}$ cycloalkyl,
$(CH_2)_n$-phenyl,
$(CH_2)_n$-naphthyl,
$(CH_2)_n$-heteroaryl, and
$(CH_2)_n$-heterocyclyl;

wherein heteroaryl is as defined above, and phenyl, naphthyl, and heteroaryl are unsubstituted or substituted with one to three groups independently selected from $R^3$; and alkyl, $(CH_2)_n$, cycloalkyl, and heterocyclyl are optionally substituted with one to three groups independently selected from $R^3$ and oxo.

In one embodiment of the compounds of structural formula I, $R^1$ is selected from the group consisting of hydrogen, $C_{1-6}$ alkyl, $(CH_2)_{0-1}C_{3-6}$ cycloalkyl, and $(CH_2)_{0-1}$-phenyl; wherein phenyl is unsubstituted or substituted with one to three groups independently selected from $R^3$; and alkyl and cycloalkyl are optionally substituted with one to three groups independently selected from $R^3$ and oxo.

In a second embodiment of the compounds of structural formula I, $R^2$ is phenyl or thienyl optionally substituted with one to three groups independently selected from $R^3$. In a class of this embodiment, $R^2$ is phenyl optionally substituted with one to three groups independently selected from $R^3$.

In a third embodiment of the compounds of structural formula I, X is selected from the group consisting of $C_{1-6}$ alkyl, $(CH_2)_n$-phenyl, $(CH_2)n$-naphthyl, $(CH_2)_n$-heteroaryl, $(CH_2)_n$-heterocyclyl, $(CH_2)_nC(O)N(R^5)(R^5)$, $(CH_2)_nCO_2R^5$, $(CH_2)_nS(O)_pR^5$, $(CH_2)_nOR^5$, $(CH_2)_nNR^5C(O)R^5$, and $(CH_2)_n NR^5SO_2R^5$; wherein heteroaryl is as defined above, and phenyl, naphthyl, and heteroaryl are optionally substituted with one to three groups independently selected from $R^3$; alkyl and heterocyclyl are optionally substituted with one to three groups independently selected from $R^3$ and oxo; and the $(CH_2)_n$ group is optionally substituted with one to three groups independently selected from $R^4$, halogen, $S(O)_pR^4$, $N(R^4)_2$, and $OR^4$. In a class of this embodiment, X is selected from the group consisting of $C_{1-6}$ alkyl, $(CH_2)_{0-1}$-phenyl, $(CH_2)_{0-1}$-heteroaryl, $(CH_2)$0-1-heterocyclyl, $(CH_2)_{0-1}NHC(O)R^5$, $(CH_2)_{0-1}CO_2R^5$, and $(CH_2)_{0-1}C(O)N(R^5)(R^5)$; wherein phenyl and heteroaryl are optionally substituted with one to three groups independently selected from $R^3$; and alkyl and heterocyclyl are optionally substituted with one to three groups independently selected from $R^3$ and oxo. In a subclass of this class, heteroaryl is selected from the group consisting of pyridyl, pyrazinyl, pyrimidinyl, triazolyl, tetrazolyl, thiadiazolyl, oxadiazolyl, pyrazolyl, and imidazolyl.

In a fourth embodiment of compounds of formula I, Y is selected from the group consisting of $C_{1-8}$ alkyl, $C_{2-6}$ alkenyl, $(CH_2)C_{3-8}$ cycloalkyl, $(CH_2)$-phenyl, $(CH_2)$-naphthyl, $(CH_2)$-heterocyclyl, and $(CH_2)$-heteroaryl, wherein phenyl, naphthyl, and heteroaryl are optionally substituted with one to three groups independently selected from $R^3$; and $(CH_2)_n$, alkyl, cycloalkyl, and heterocyclyl are optionally substituted with one to three groups independently selected from $R^3$ and oxo. In a class of this embodiment, Y is selected from the group consisting of $C_{1-8}$ alkyl, $C_{2-6}$ alkenyl, $C_{5-7}$ cycloalkyl, and phenyl; wherein phenyl is unsubstituted or substituted with one to three groups independently selected from $R^3$; and alkyl and cycloalkyl are unsubstituted or substituted with one to three groups independently selected from $R^3$ and oxo. In a subclass of this class, Y is cyclohexyl or $C_{1-6}$ alkyl; wherein the cyclohexyl and alkyl groups are unsubstituted or substituted with one to three groups independently selected from $R^3$ and oxo.

In yet a further embodiment of compounds of structural formula I, r is 1 or 2 and s is 1.

In yet a further embodiment of the compounds of the present invention, there are provided compounds of structural formula IIa or IIb of the indicated relative stereochemical configurations having the trans orientation of the $R^2$ and piperidinecarbonyl substituents:

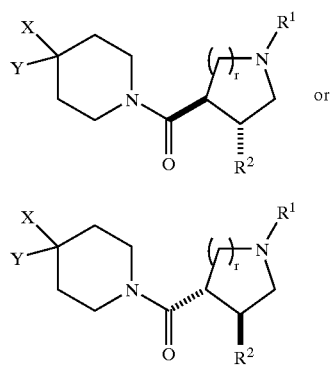

or a pharmaceutically acceptable salt thereof;
wherein
r is 1 or 2;
n is 0, 1, or 2;
p is 0, 1, or 2;

$R^1$ is hydrogen, amidino, $C_{1-4}$ alkyliminoyl, $C_{1-6}$ alkyl, $C_{5-6}$ cycloalkyl, $(CH_2)_{0-1}$ phenyl, $(CH_2)_{0-1}$ heteroaryl; wherein phenyl and heteroaryl are unsubstituted or substituted with one to three groups independently selected from $R^3$, and alkyl and cycloalkyl are unsubstituted or substituted with one to three groups independently selected from $R^3$ and oxo;

$R^2$ is phenyl or thienyl optionally substituted with one to three groups independently selected from $R^3$;

$R^3$ is selected from the group consisting of
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
$OR^4$,
$(CH_2)_nN(R^4)_2$,
$(CH_2)_nC≡N$,
$CO_2R^4$,
$C(R^4)(R^4)N(R^4)_2$,
$NO_2$,
$(CH_2)_nNR^4SO_2R^4$
$(CH_2)_nSO_2N(R^4)_2$,
$(CH_2)_nS(O)_pR^4$,
$(CH_2)_nNR^4C(O)N(R^4)_2$,
$(CH_2)_nC(O)N(R^4)_2$,
$(CH_2)_nNR^4C(O)R^4$,
$(CH_2)_nNR^4CO_2R^4$,
$CF_3$,
$CH_2CF_3$,
$OCF_3$, and
$OCH_2CF_3$;

in which heteroaryl is as defined above; phenyl, naphthyl, heteroaryl, cycloalkyl, and heterocyclyl are unsubstituted or substituted with one to two substituents independently selected from halogen, hydroxy, $C_{1-4}$ alkyl, trifluoromethyl, and $C_{1-4}$ alkoxy; and $(CH_2)_n$ is unsubstituted or substituted with one to two groups independently selected from halogen, hydroxy, and $C_{1-4}$ alkyl;

each $R^4$ is independently selected from the group consisting of
hydrogen,
$C_{1-8}$ alkyl, and
$C_{3-6}$ cycloalkyl;

wherein cycloalkyl is unsubstituted or substituted with one to three groups independently selected from halogen, $C_{1-4}$ alkyl, and $C_{1-4}$ alkoxy; or two $R^4$ groups together with the atom to which they are attached form a 4- to 8-membered mono- or bicyclic ring system optionally containing an additional heteroatom selected from O, S, and $NC_{1-4}$ alkyl;

Y is selected from the group consisting of
$C_{1-8}$ alkyl,
$C_{2-6}$ alkenyl,
$(CH_2)_{0-1}C_{3-8}$ cycloalkyl,
$(CH_2)_{0-1}$-phenyl,
$(CH_2)_{0-1}$-naphthyl, and
$(CH_2)_{0-1}$-heteroaryl;

wherein phenyl, naphthyl, and heteroaryl are unsubstituted or substituted with one to three groups independently selected from $R^3$; and alkyl, $(CH_2)$, and cycloalkyl are unsubstituted or substituted with one to three groups independently selected from $R^3$ and oxo; and X is selected from the group consisting of:

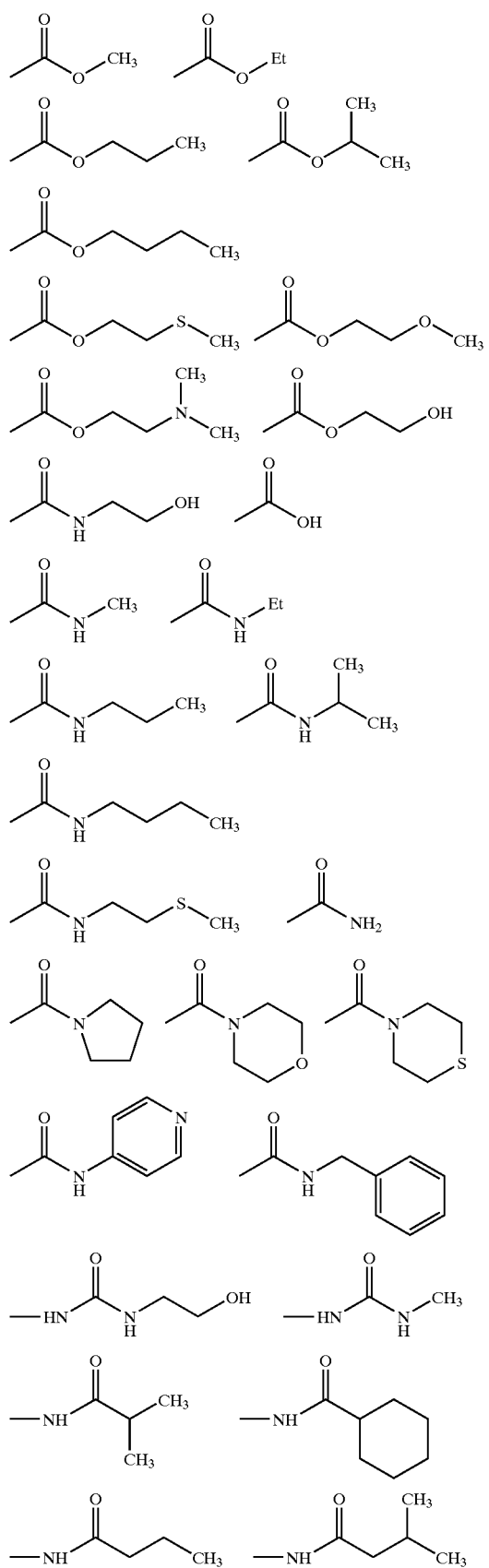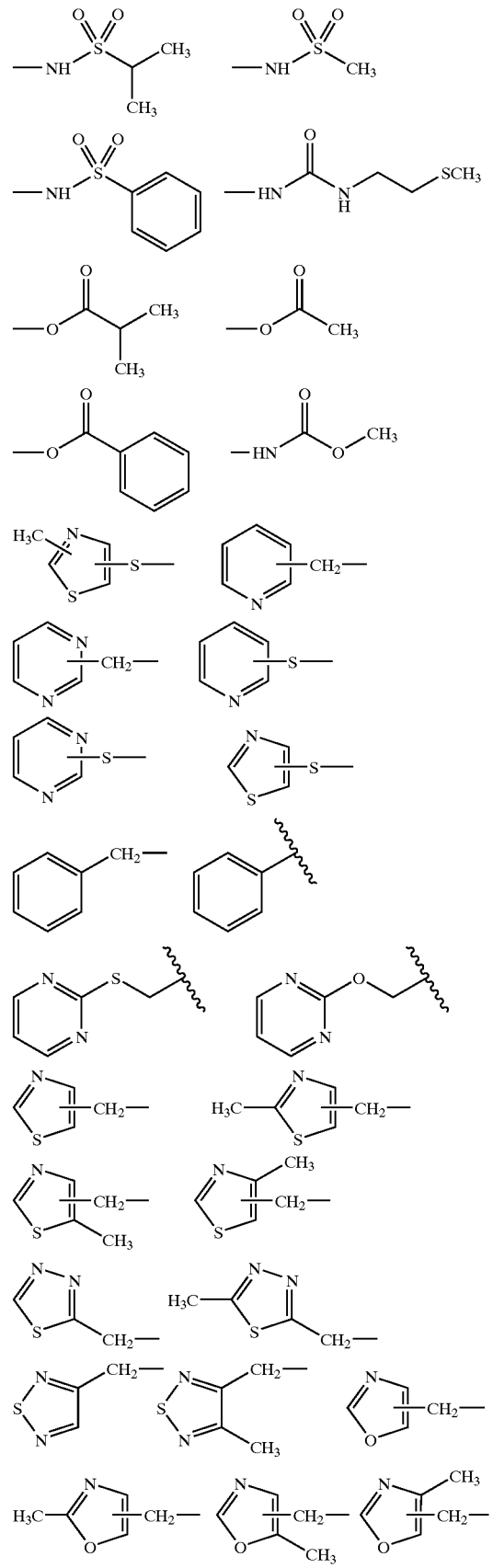

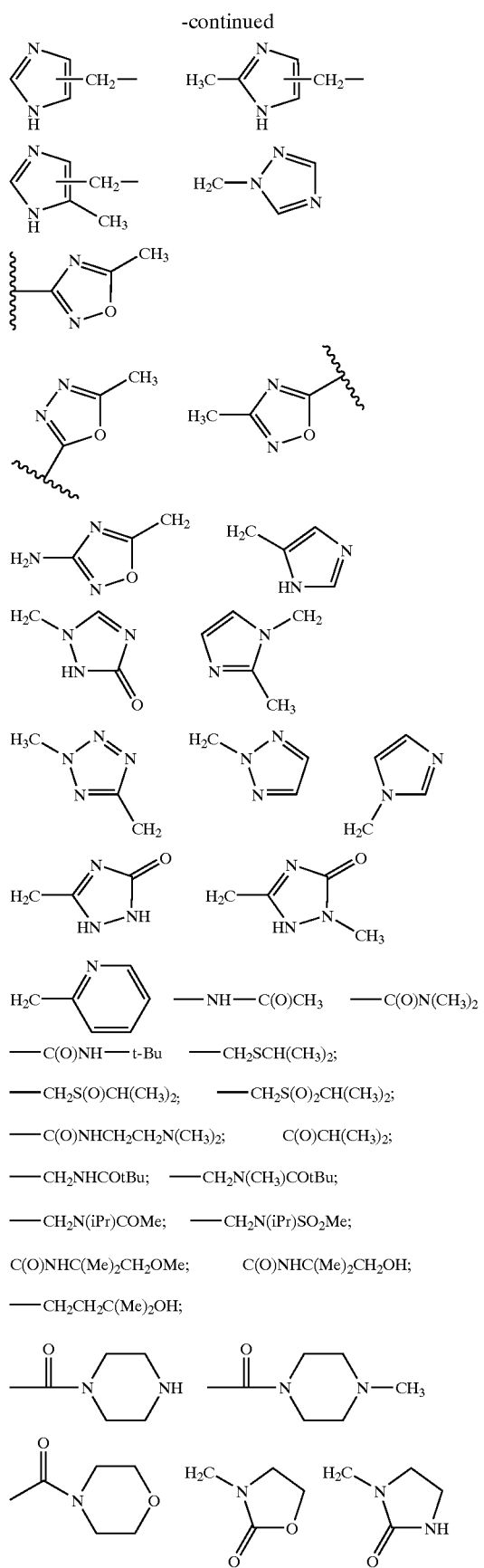
In yet a further embodiment of the compounds of the present invention, there are provided compounds of structural formula IIIa or IIIb of the indicated relative stereochemical configurations having the trans orientation of the phenyl and piperidinecarbonyl substituents:
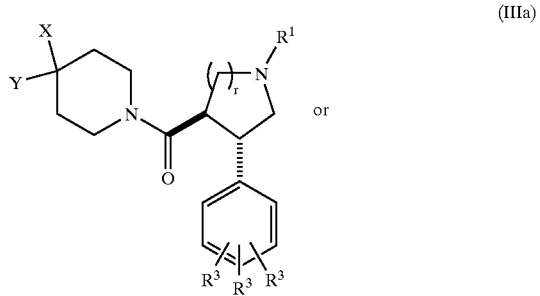

-continued

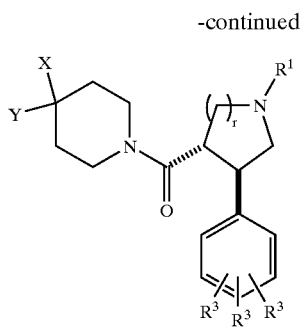
(IIIb)

or a pharmaceutically acceptable salt thereof;

wherein r is 1 or 2;

$R^1$ is hydrogen, $C_{1-4}$ alkyl or $(CH_2)_{0-1}$ phenyl;

each $R^3$ is independently selected from the group consisting of hydrogen, halogen, $C_{1-4}$ alkyl, trifluoromethyl, and $C_{1-4}$ alkoxy;

Y is cyclohexyl or phenyl; and

X is selected from the group consisting of

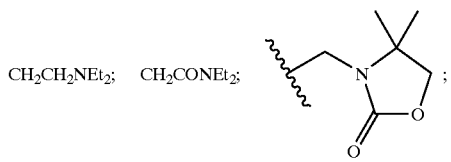

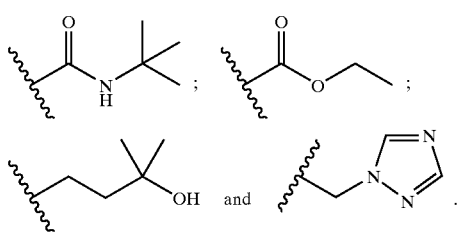

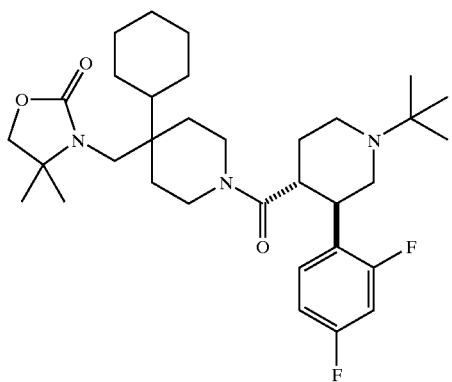

Illustrative but nonlimiting examples of compounds of the present invention that are useful as melanocortin agonists are the following:

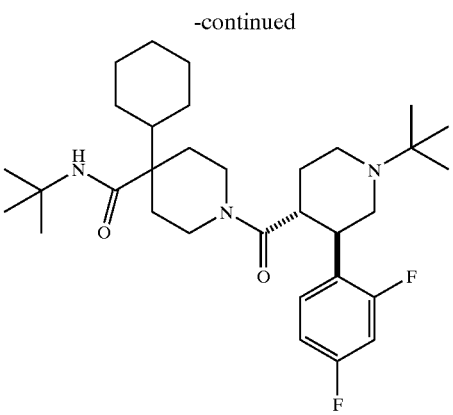

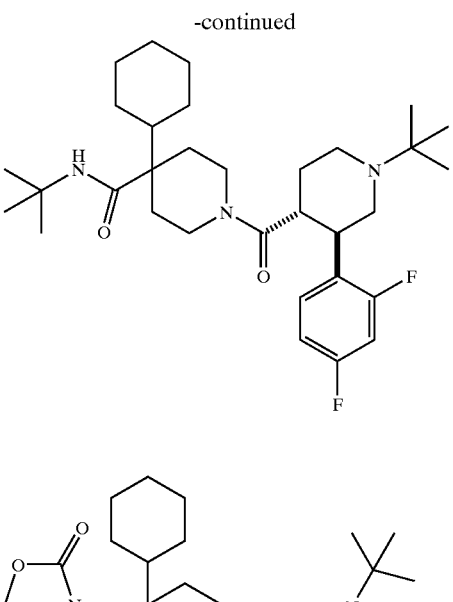

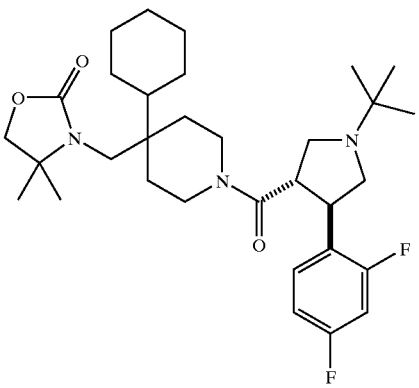

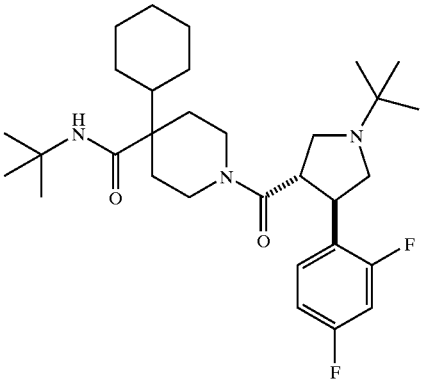

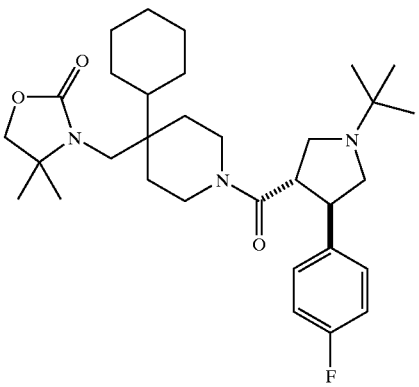

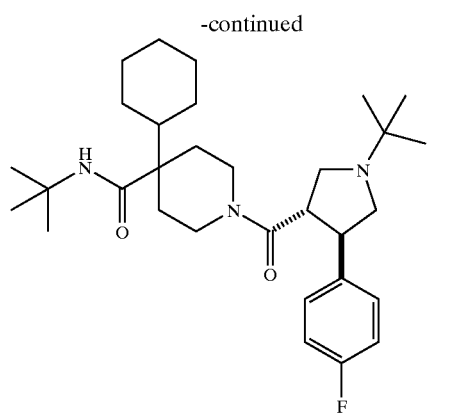
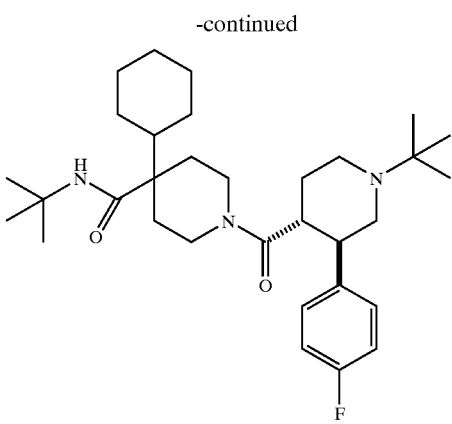
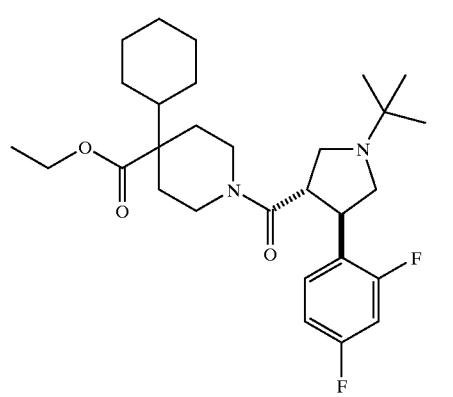
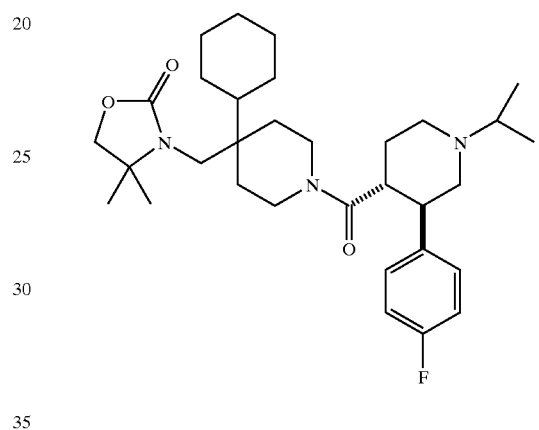
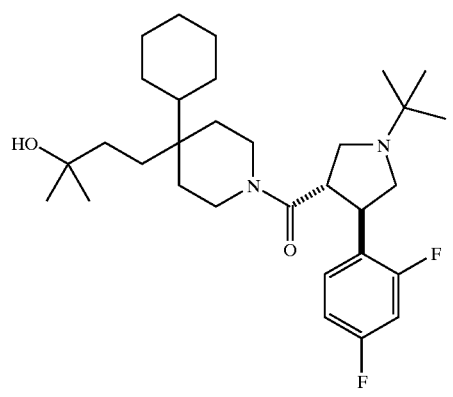
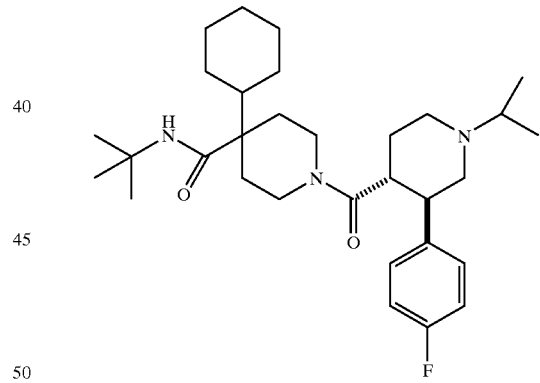
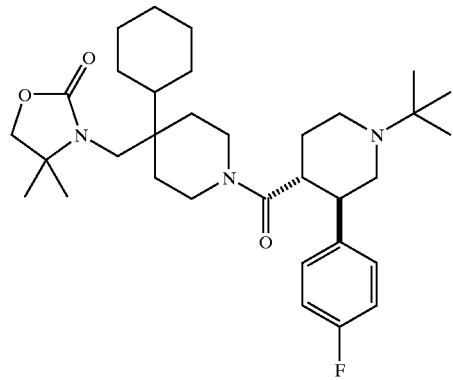
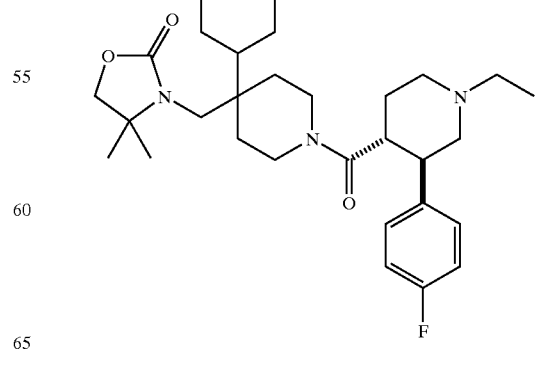

-continued
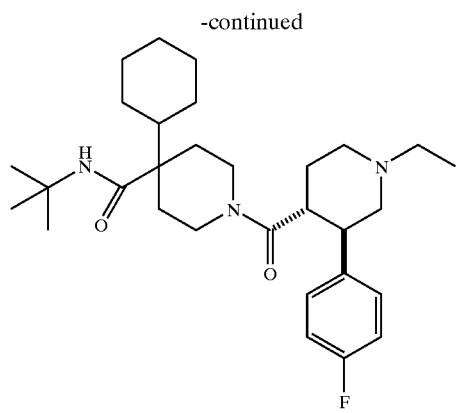
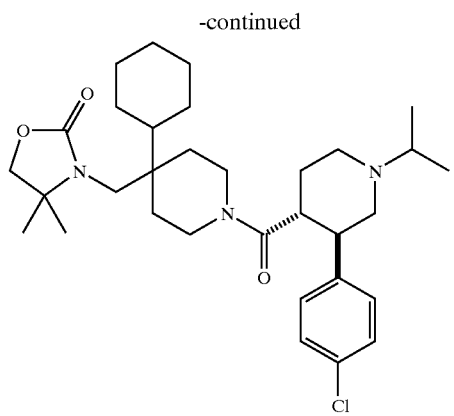
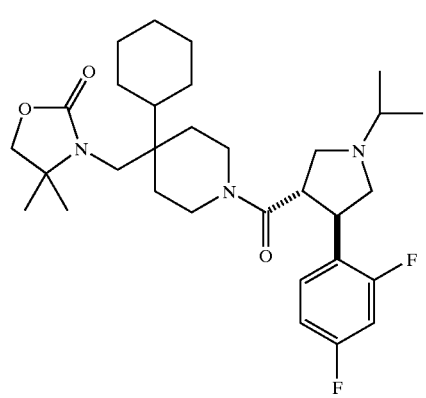
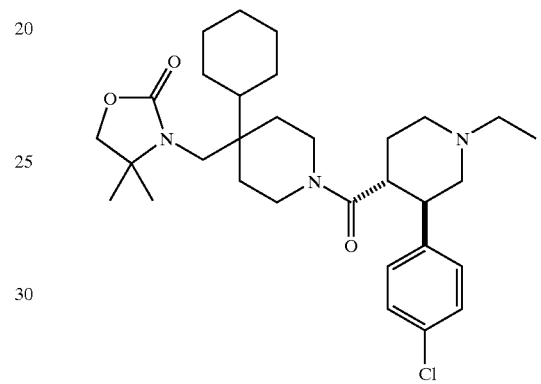
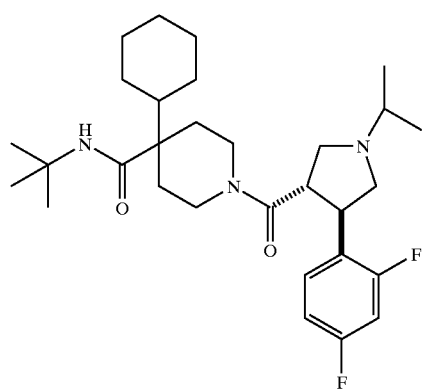
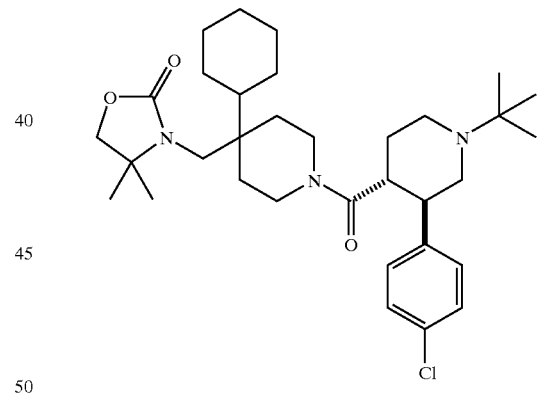
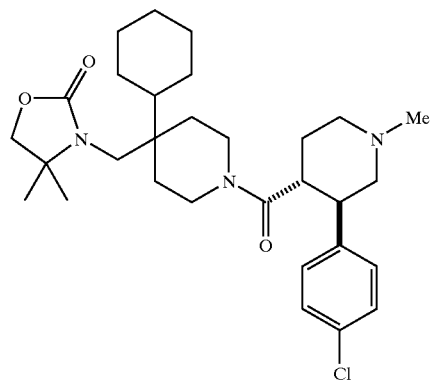
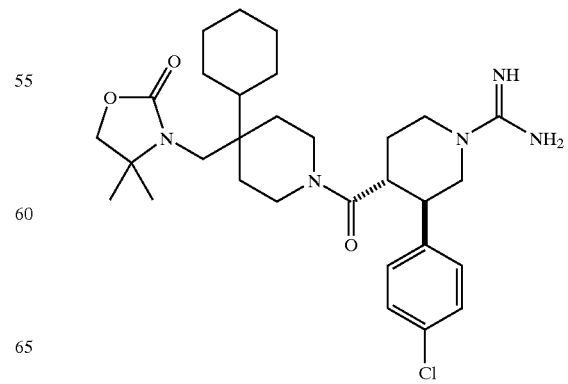

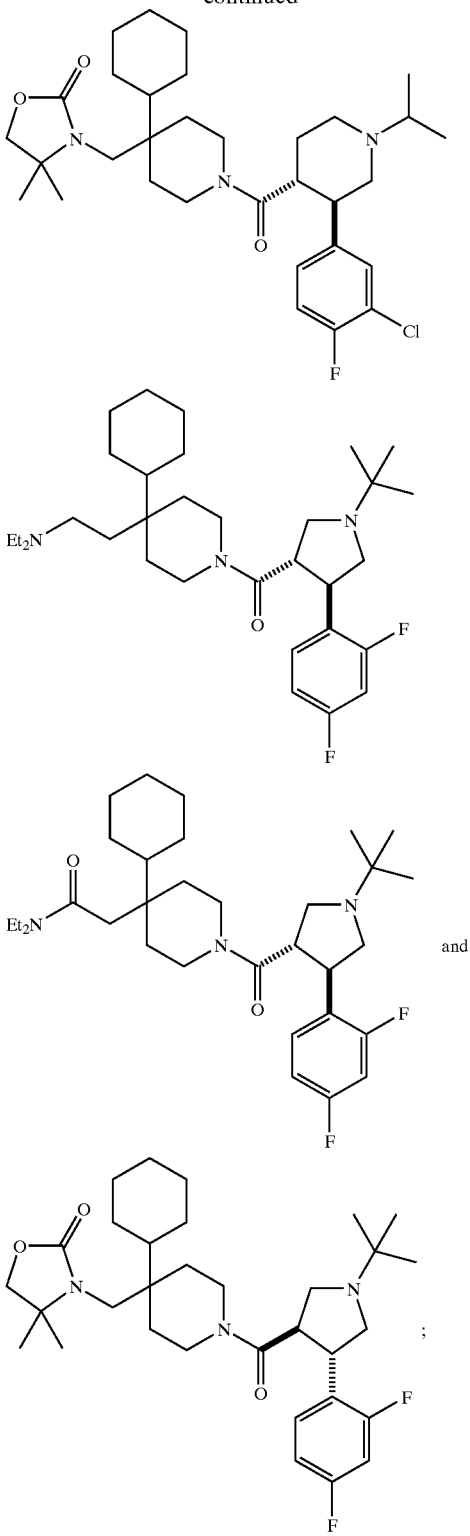

or a pharmaceutically acceptable salt thereof.

The compounds of structural formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a subject in need thereof which comprises administering to said subject a therapeutically or prophylactically effective amount of a compound of structural formula I.

Another aspect of the present invention provides a method for the treatment or prevention of male or female sexual dysfunction including erectile dysfunction which comprises administering to a subject in need of such treatment or prevention a therapeutically or prophylactically effective amount of a compound of structural formula I.

Another aspect of the present invention provides a pharmaceutical composition comprising a compound of structural formula I and a pharmaceutically acceptable carrier.

Yet another aspect of the present invention provides a method for the treatment or prevention of male or female sexual dysfunction including erectile dysfunction which comprises administering to a subject in need of such treatment or prevention a therapeutically or prophylactically effective amount of a compound of structural formula I in combination with a therapeutically effective amount of another agent known to be useful for the treatment of these conditions.

Yet another aspect of the present invention provides a method for the treatment or prevention of obesity which comprises administering to a subject in need of such treatment or prevention a therapeutically or prophylactically effective amount of a compound of structural formula I in combination with a therapeutically effective amount of another agent known to be useful for the treatment of this condition.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "$C_{1-4}$ alkyliminoyl" means $C_{1-3}C(=NH)-$.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-Membered heteroaryl" represents a monocyclic heteroaromatic ring; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include nonaromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

An embodiment of the term "mammal in need thereof" is a "human in need thereof," said human being either male or female.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, IIa, IIb, IIIa, and IIIb may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor relative to MC-1R, MC-2R, MC-3R, and MC-5R, which makes them especially useful in the prevention and treatment of obesity, as well as male and/or female sexual dysfunction, including erectile dysfunction.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose), (e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) anti-obesity serotonergic agents, such as fenfluramine, dexfenfluramine, phentermine, and sibutramine;

(h) β3-adrenoreceptor agonists;

(i) pancreatic lipase inhibitors, such as orlistat;

(j) feeding behavior modifying agents, such as neuropeptide YY1 and Y5 antagonists, such as those disclosed in WO 97/19682, WO 97/20820, WO 97/20821, WO 97/20822, WO 97/20823, WO 01/14376, and U.S. Pat. No. 6,191,160;

(k) orexin-1 receptor antagonists;

(l) PPARα agonists such as described in WO 97/36579 by Glaxo;

(m) PPARγ antagonists as described in WO 97/10813;

(n) serotonin reuptake inhibitors such as fluoxetine, paroxetine, and sertraline;

(o) growth hormone secretagogues, such as MK-0677;

(p) cannabinoid receptor ligands, such as cannabinoid $CB_1$ receptor antagonists or inverse agonists; and (q) protein tyrosine phosphatase-1B (PTP-1B) inhibitors.

Examples of anti-obesity agents that can be employed in combination with a compound of Formula I are disclosed in "Patent focus on new anti-obesity agents," *Exp. Opin. Ther. Patents,* 10: 819–831 (2000); "Novel anti-obesity drugs," *Exp. Opin. Invest. Drugs,* 9: 1317–1326 (2000); and "Recent advances in feeding suppressing agents: potential therapeutic strategy for the treatment of obesity, *Exp. Pin. Ther. Patents,* 11: 1677–1692 (2001). The role of neuropeptide Y in obesity is discussed in *Exp. Opin. Invest. Drugs,* 9: 1327–1346 (2000). Cannabinoid receptor ligands are discussed in *Exp. Opin. Invest. Drugs,* 9: 1553–1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)-pyrazino[2',1':6,1]pyrido[3,4-b]indole-1, 4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in PCT International Application Publications WO 99/64002 (16 Dec. 1999) and WO 00/74679 (14 Dec. 2000), which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as methylene chloride in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

| Abbreviations Used in the Description of the Preparation of the Compounds of the Present Invention: | |
|---|---|
| BOC (boc) | t-butyloxycarbonyl |
| BOP | benzotriazol-1-yloxytris(dimethylamino)phosphonium hexafluorophosphate |
| Bu | butyl |
| calc. | calculated |
| CBZ (Cbz) | benzyloxycarbonyl |
| c-hex | cyclohexyl |
| c-pen | cyclopentyl |
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| EDC | 1-(3-dimethylaminopropyl)3-ethylcarbodiimide HCl |
| eq. | equivalent(s) |
| ES-MS | electron spray ion-mass spectroscopy |
| Et | ethyl |
| EtOAc | ethyl acetate |
| HATU | N-[(dimethylamino)-1H-1,2,3-triazolo[4,5-b] pyridin-1-ylmethylene]-N-methylmethanaminium hexafluorophosphate N-oxide |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-xR | melanocortin receptor (x being a number) |
| Me | methyl |
| MF | molecular formula |
| MS | mass spectrum |
| Ms | methanesulfonyl |
| OTf | trifluoromethanesulfonyl |
| Ph | phenyl |
| Phe | phenylalanine |
| Pr | propyl |
| prep. | prepared |
| PyBrop | bromo-tris-pyrrolidino-phosphonium hexafluorophosphate |
| r.t. | room temperature |
| TFA | trifluoroacetic acid |
| THF | tetrahydrofuran |
| TLC | thin-layer chromatography. |

Reaction Schemes A-L illustrate the methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a 4-substituted piperidine of 1 with a carboxylic acid derivative of formula 2 affords a title compound of structural formula I where $R^1$ is an N-tert-butoxycarbonyl group (N-BOC). The amide bond coupling reaction illustrated in reaction Scheme A is conducted in an appropriate inert solvent such as methylene chloride, dimethylformamide (DMF) or the like and may be performed with a variety of reagents suitable for amide coupling reactions such as 1-(3-dimethylaminopropyl)-3-ethylcarbodiimide hydrochloride (EDC) or benzotriazol-1-yloxytripyrrolidinephosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA) or N-methylmorpholine (NMM), or the addition of an additive such as 1-hydroxybenzotriazole (HOBt). Alternatively, 4-substituted piperidines of formula 1 may be treated with an active ester or acid chloride derived from carboxylic acid 2 which also affords compounds of structural formula I ($R^1$=BOC).

The amide bond coupling shown in reaction Scheme A is usually conducted at temperatures between 0° C. and room temperature, occasionally at elevated temperatures, and the coupling reaction is typically conducted for periods of 1 to 24 hours.

If it is desired to produce a compound of structural formula I wherein $R^1$ is a hydrogen, the N-BOC protected compounds of structural formula I are then deprotected under acidic conditions, for instance using trifluoroacetic acid in a solvent like methylene chloride at room temperature.

When it is desired to prepare compounds of structural formula I wherein $R^1$ is not a hydrogen, the compounds of general formula I ($R^1$=H) may be further modified using the methodology described below in reaction Scheme L.

Reaction Schemes B-I illustrate methods for the synthesis of the carboxylic acids of general formula 2 that are utilized in the amide bond coupling reaction shown in reaction Scheme A. Reaction Schemes J-K illustrate additional methods for the synthesis of 4-substituted piperidines of general formula 1 that are used in that same step. The compounds of structural formula 1 in which the $R^1$ substituent is a group other than a hydrogen atom are generally prepared from compounds of structural formula I wherein R=H using a variety of synthetic methods known in the literature of organic synthesis. Specific examples of such transformations are outlined in reaction Schemes and provided in the procedures for the Examples presented below.

Reaction Scheme B illustrates a preferred method for the synthesis of compounds of general formula 2 wherein r is 2 and s is 1 such that the resulting heterocycle is a 3-aryl-4-piperidine carboxylic acid derivative 10. The synthesis of 10 begins with a commercially available β-keto ester such as 3. Generally a protecting group interchange of an N-BOC group for the N-benzyl group is performed initially. Thus a β-keto ester of formula 3 is subjected to debenzylation by hydrogenolysis using a palladium-on-carbon catalyst in a solvent system such as 1:1 ethanol-water under a hydrogen atmosphere. The resulting piperidone 4 is then protected as its tert-butyl carbamate using BOC anhydride in the presence of a base and a suitable solvent. For example, this can be accomplished in a two phase mixture of chloroform and aqueous sodium bicarbonate as shown. Incorporation of the 3-aryl substituent is then performed in two steps. First, the β-keto ester group is converted to the corresponding vinyl triflate 6 using trifluoromethanesulfonic anhydride and an organic base like N,N-diisopropylethylamine in an aprotic solvent such as methylene chloride. The resulting vinyl triflate 6 is then subjected to a palladium-catalyzed cross-coupling reaction with an aryl boronic acid (7) using a palladium (II) catalyst such as [1,1'-bis(diphenylphosphino)-ferrocene]dichloropalladium(II). Preferred conditions for this reaction are the use of a toluene-ethanol-aqueous sodium carbonate solvent system at an elevated temperature, for instance 50–100° C., for a period of 2–24 hours. The resulting aryl-substituted tetrahydropyridine derivative 8 can be reduced to a piperidine such as 9 using a variety of known techniques and the method chosen will determine the stereochemical outcome of the product. For instance, hydrogenation of 8 with a palladium on carbon catalyst in a solvent such as ethanol affords cis-3,4-disubstituted piperidines of general formula 9. Alternatively, a dissolving metal reduction using a metal, such as magnesium in methanol, reduces the double bond of 8 and produces a mixture of both cis and trans 3,4-disubstituted piperidines of formula 9. The resulting mixture of cis and trans diastereoisomers may be separated chromatographically or it may be subsequently epimerized to afford the pure trans isomer of 9 by treating the mixture with a base like sodium methoxide in methanol. Finally, hydrolysis of either the cis or trans 3-aryl-4-piperidine carboxylic ester 9 affords either a cis or trans 3-aryl-4-piperidine carboxylic acid of general formula 10, corresponding to an acid of general formula 2 wherein r is 2 and s is 1. The cis or trans carboxylic acids of general formula 10 are produced as racemates and either may be resolved to afford enantiomerically pure compounds by methods known in organic synthesis. Preferred methods include resolution by crystallization of diastereoisomeric salts derived from acids 10 and a chiral amine base or the use of chiral stationary phase liquid chromatography columns.

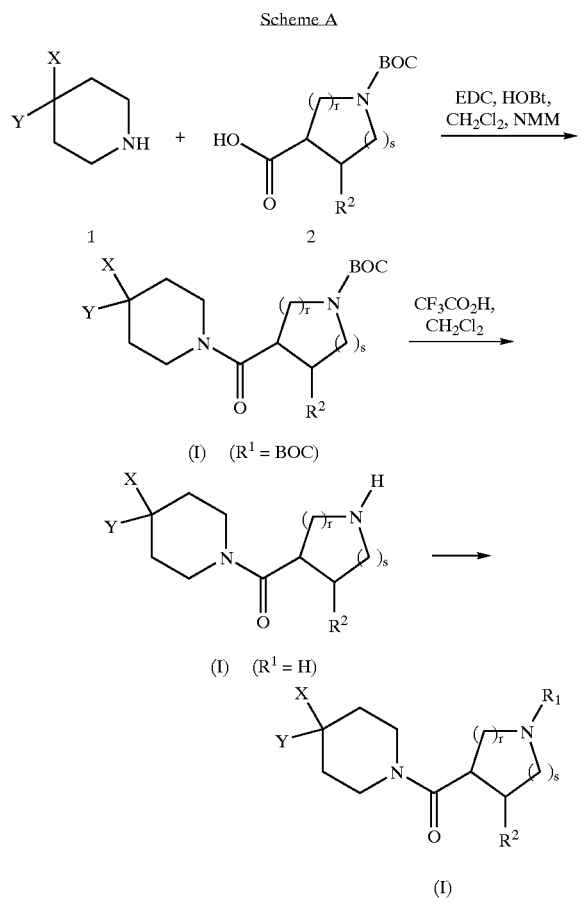

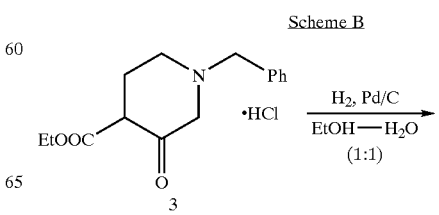

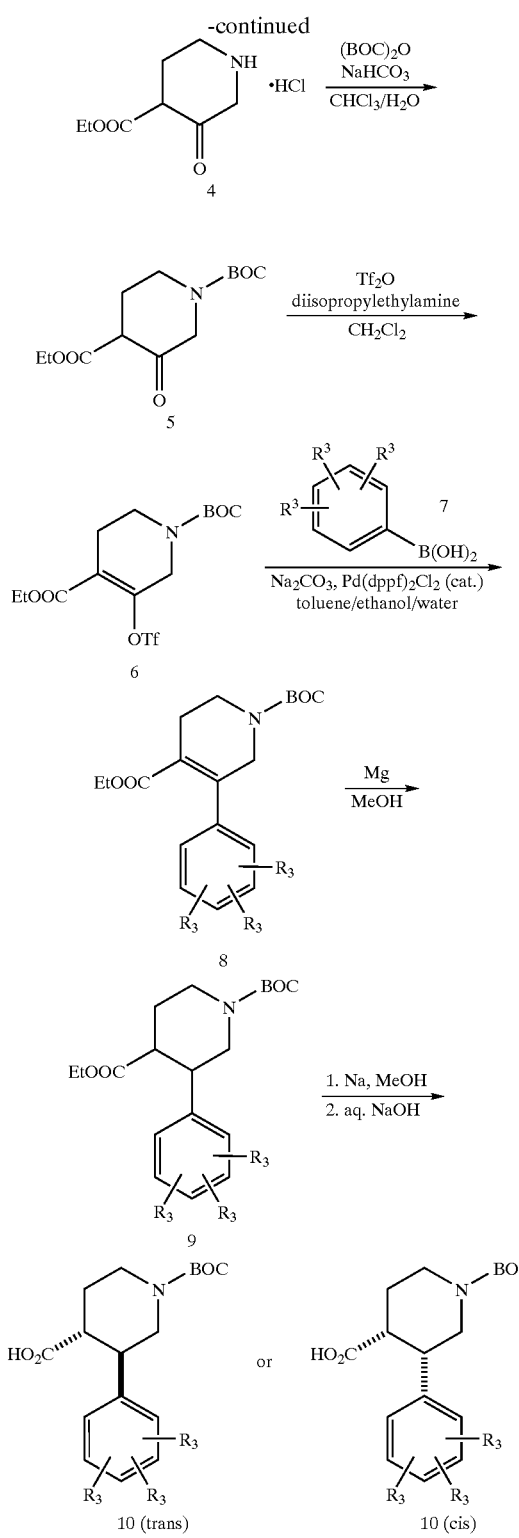
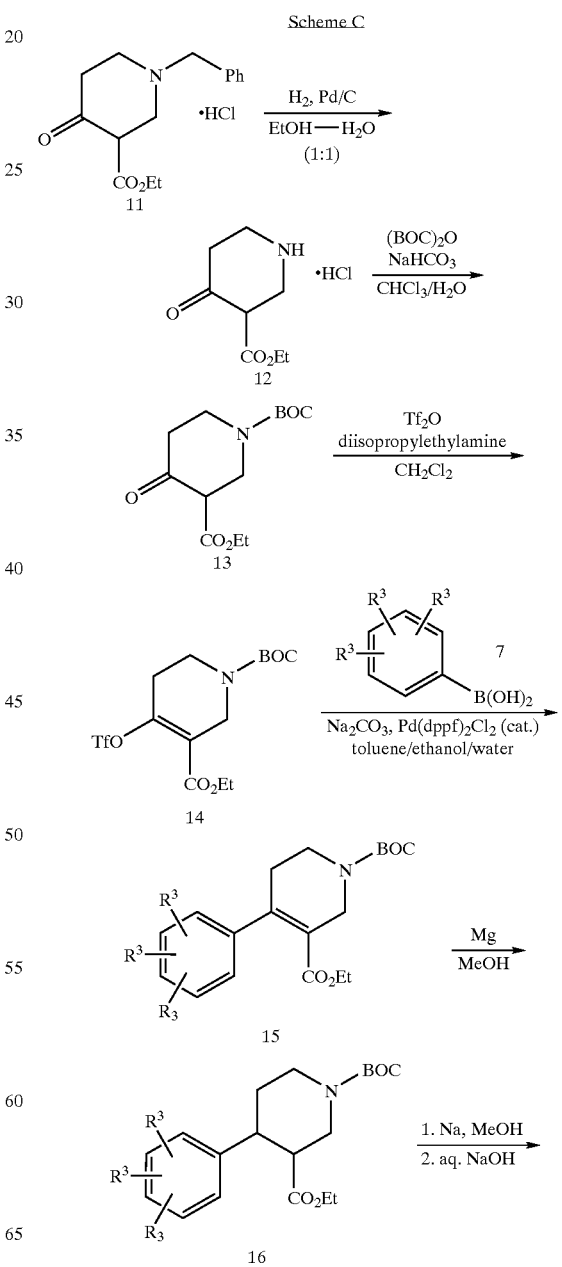

N-BOC-protected piperidine 13 is performed as shown and the resulting β-keto ester is subjected to the two-step arylation protocol previously described to yield 15. Reduction of the double bond of 15 using conditions appropriate for obtaining either cis or trans 17 is followed by ester hydrolysis which affords either a cis or trans 4-aryl-3-piperidine-carboxylic acid of general formula 17 which corresponds to an acid of general formula 2 wherein r is 1 and s is 2. The cis or trans carboxylic acids of general formula 17 are produced as racemates and either may be resolved to afford enantiomerically pure compounds by methods known in organic synthesis. Preferred methods include resolution by crystallization of diastereoisomeric salts derived from the acids 17 and a chiral amine base or by the use of chiral stationary phase liquid chromatography columns.

Reaction Scheme C illustrates a preferred method for the synthesis of compounds of general formula 2 wherein r is 1 and s is 2, such that the resulting heterocycle is a 4-aryl-3-piperidine-carboxylic acid derivative 17. The synthesis of 17 is similar to the one shown in reaction Scheme B, and may begin with either of the commercially available β-keto esters 11 or 12. Conversion of one of these starting materials to the

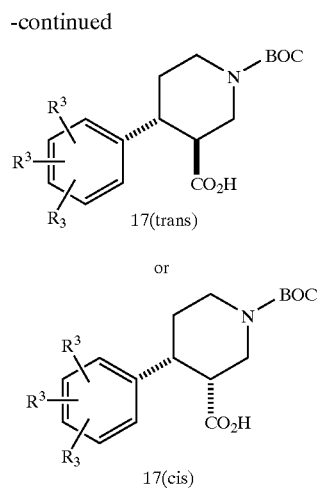

17(trans)

or

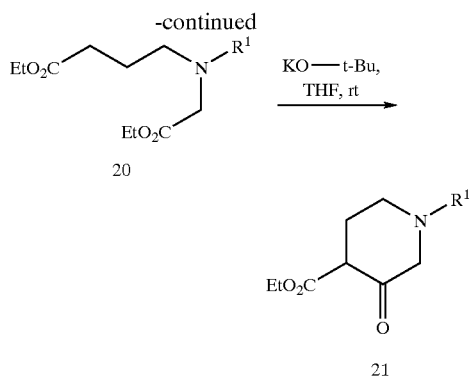

17(cis)

The synthesis of the N-BOC protected carboxylic acids of general formula 10 and 17 illustrated in reaction Schemes B and C are useful for the preparation of title compounds of structural formula I bearing a variety of $R^1$ substituents as noted above. For the synthesis of certain title compounds of structural formula I, for instance when it is desired that $R^1$ be a tert-butyl group, it is preferable to incorporate that $R^1$ substituent at an earlier stage of the synthesis. The synthesis of a 1-substituted-3-ketopiperidine-4-carboxylic ester (21) is shown in reaction Scheme D. A primary amine 18 bearing a desired $R^1$ substituent like a tert-butyl group is reacted with ethyl 4-bromobutyrate at elevated temperature in the absence of a solvent to afford the N-substituted ethyl 4-aminobutyrate 19. The amino ester 19 is then alkylated a second time with ethyl bromoacetate in a high boiling inert solvent such as toluene and in the presence of a base such as powdered potassium carbonate. The resulting aminodiesters of general formula 20 are then cyclized using an intramolecular Dieckmann reaction to afford piperidines such as 21. The Dieckmann reaction is performed using a strong base such as potassium tert-butoxide or the like, in an aprotic solvent such as THF at temperatures between room temperature and the boiling point of the solvent. The resulting 1-substituted-3-ketopiperidine-4-carboxylic ester 21 corresponds to a compound of general formula 5 shown in reaction Scheme B, where the BOC group is replaced with the desired $R^1$ substituent. The compounds of general formula 21 may then be converted to compounds of general formula 2 where the $R^1$ substituent replaces the BOC group using the reaction sequence illustrated in reaction Scheme B.

Scheme D

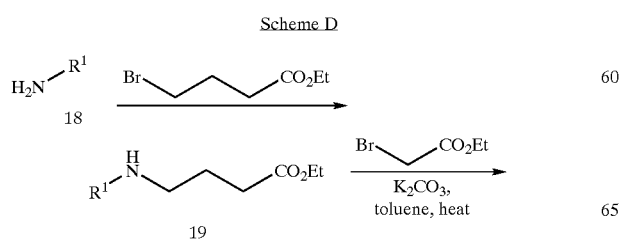

When it is desirable to synthesize a compound of general formula 17 wherein the BOC group is replaced with a substituent group $R^1$, a reaction sequence similar to the one illustrated in reaction Scheme C may be employed as shown in reaction Scheme E. An amine 18 bearing the desired $R^1$ substituent is first subjected to a Michael addition with excess ethyl acrylate in the presence of a solvent such as THF or ethanol. The resulting diester 22 is then converted to a 1-substituted-4-ketopiperidine-3-carboxylic ester 23 using an intramolecular Dieckmann reaction under conditions similar to those illustrated in reaction Scheme C. The substituted piperidine 23 corresponds to a compound of general formula 13 shown in reaction Scheme C, wherein the BOC group is replaced with the desired $R^1$ substituent. The compounds of general formula 23 may then be converted to compounds of general formula 2 where the $R^1$ substituent replaces the BOC group using the methodology illustrated in reaction Scheme C.

Scheme E

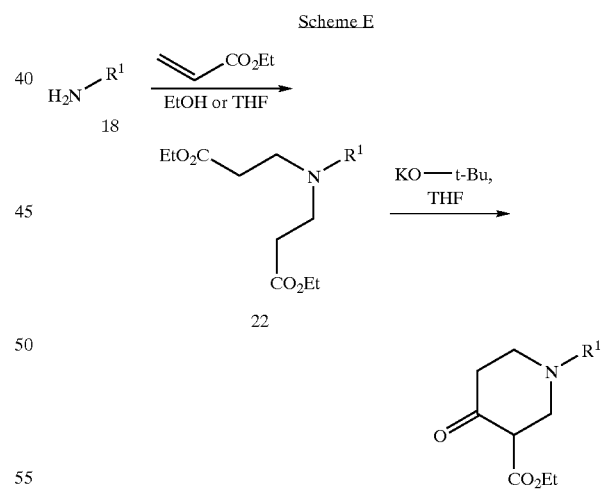

Reaction Scheme F illustrates a strategy for the synthesis of compounds of general formula 2 when the values of r and s are selected such that the resulting heterocycle is a 3-aryl-4-pyrrolidine carboxylic acid derivative (29). The preferred method for the synthesis of compounds of general formula 29 involves the azomethine ylid 3+2 cycloaddition reaction of an azomethine ylid precursor of general formula 25 and a substituted cinnamic ester 24. The azomethine cycloaddition reaction of 24 and 25 affords the 3,4-disubstituted pyrrolidine 26, and the stereochemical relationship of the substituents on the newly formed pyrrolidine ring is determined by the stereochemistry of the double bond in the cinnamate ester 24. Thus the trans ester 24 affords a trans 3,4-disubstituted pyrrolidine of formula 26 as shown. The corresponding cis cinnamate ester affords a cis 3,4-disubstituted pyrrolidine of general formula 26. Cis or trans 3-arylpyrrolidine-4-carboxylic esters of general formula 26 may be resolved to afford enantiomerically pure compounds using a method such as resolution by crystallization of the diastereoisomeric salts derived from 26 and a chiral carboxylic acid, or directly by the use of chiral stationary phase liquid chromatography columns. Reaction Scheme F illustrates the case where a trans cinnamic ester 24 is converted to a trans 3,4-disubstituted pyrrolidine 26 and its subsequent resolution affords the enantiomerically pure trans pyrrolidine esters 27 and 28. Finally, the esters of general formula 26 (or their pure enantiomers 27 and 28) are hydrolyzed to the corresponding amino acid hydrochlorides of general formula 29 as shown at the bottom of reaction Scheme F.

Amino acids of general formula 29 are zwitterionic. Therefore it is in some cases difficult to achieve efficient separation and purification of these compounds from aqueous reactions or workups. In these cases it is preferred to effect the hydrolysis using a reagent such potassium trimethylsilanolate in diethyl ether. Under these conditions the potassium salt of the carboxylic acid is produced which affords an easily isolated precipitate in ether. The resulting salt is then converted to the corresponding amino acid hydrochloride by treatment with excess hydrochloric acid in a suitable solvent such as ethyl acetate. Alternatively, esters such as 26 may be converted directly to the amino acid hydrochlorides 29 under acidic hydrolysis conditions. The hydrolysis of the ester 26 is achieved by prolonged reaction with concentrated hydrochloric acid at an elevated temperature. For example, this reaction may be conducted in 8 M hydrochloric acid at reflux overnight. The reaction mixture is then cooled and evaporated in vacuo to afford the amino acid hydrochloride 29. The amino acid hydrochlorides of general formula 29 correspond to an amino acid hydrochloride of general formula 2 wherein both r and s are 1 and may be employed directly in the amide bond coupling step illustrated in reaction Scheme A to produce the compounds of the present invention of structural formula I.

Scheme F

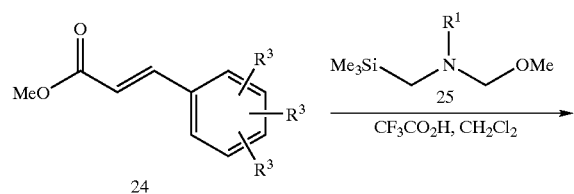

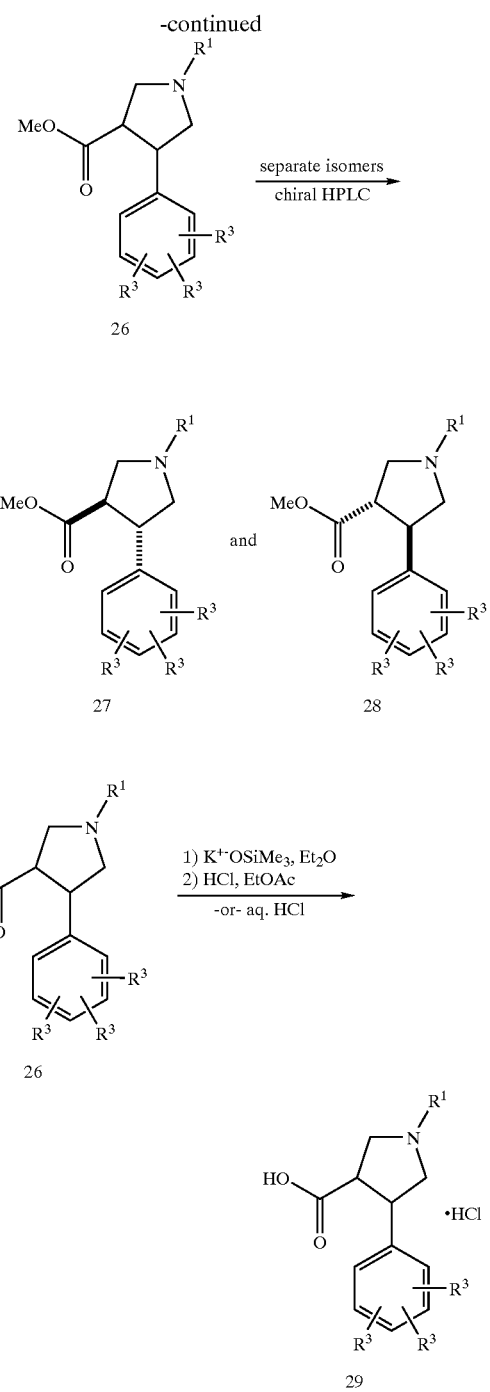

Another preferred method for the synthesis of enantiomerically pure 3-arylpyrrolidine-4-carboxylic acid derivatives is illustrated in reaction Scheme G. In this synthetic method, a substituted cinnamic acid of general formula 29 is first derivatized with a chiral auxilliary such as (S)-(−)-4-benzyl-2-oxazolidinone (30). The acylation of chiral auxiliary 30 with cinnamic acids of formula 29 is performed by initial activation of the acid to afford a mixed anhydride. Typically acids of general formula 29 are reacted with an acid chloride such as pivaloyl chloride in the presence of a base such as triethylamine and in a suitable aprotic solvent such as THF. The intermediate cinnamyl-pivaloyl anhydride is converted to the product 31 by reaction with the oxazolidinone 30 in the presence of lithium chloride, an amine base such as triethylamine and in a solvent such as THF, and the reaction is conducted at temperatures between −20° C. and room temperature for periods of 1–24 hours. Alternatively, the oxazolidinone 30 may be deprotonated with a strong base such as n-butyllithium in THF at low temperatures such as −78° C. and then reacted with a mixed anhydride obtained from acid 29 and an acid chloride like pivaloyl chloride as noted above. The cinnamyl oxazolidinone of general formula 31, which is produced by either of these methods, is then reacted with the azomethine ylid precursor 25 in a manner similar to that described in reaction Scheme F, and the products of the reaction are the substituted pyrrolidines of general formulas 33 and 34 as shown. The products 33 and 34 are diastereoisomers of each other and may therefore be separated by standard methods such as recrystallization or by liquid chromatography on a solid support such as silica gel. As discussed above, if the cis isomer of the cinnamic acid of general formula 29 is employed in the first step of reaction Scheme G, then a cis isomer of the substituted cinnamyl oxazolidinone 31 is produced. If such a cis cinnamyl oxazolidinone is then subjected to the azomethine ylid cycloaddition with an azomethine ylid precursor of formula 25, the products are the diastereoisomeric cis-disubstituted pyrrolidines related to 33 and 34.

Scheme G

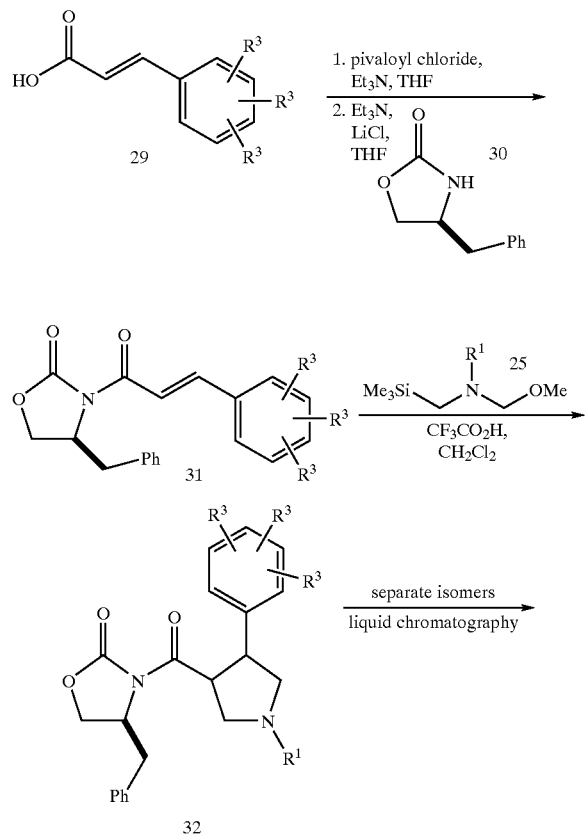

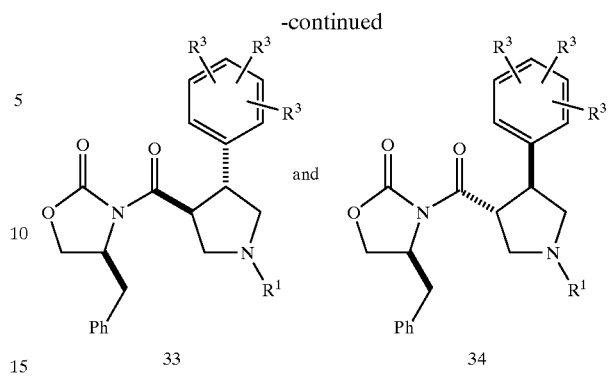

The azomethine ylid cycloaddition reactions shown in reaction Schemes F and G are generally conducted with the commercially available azomethine ylid precursor N-(methoxymethyl)-N-(trimethylsilylmethyl)-benzylamine (25, $R^1$=—$CH_2Ph$). When the $R^1$ substituent in the title compounds of structural formula I is chosen to be a group other than benzyl, it is generally preferable to remove the benzyl group from the substituted pyrrolidine compound at this point, and replace it with a more readily removed protecting group such as an N-BOC group. Reaction Scheme H illustrates this process with a generalized 3,4-disubstituted pyrrolidine of formula 32. The preferred method for removal of the N-benzyl group from compounds of general formula 32 will depend upon the identity of the $R^3$ substituents. If these substituents are unaffected by hydrogenation conditions, then the N-benzyl group may be removed by hydrogenolysis using a palladium on carbon catalyst in a solvent such as ethanol and in the presence of hydrogen gas or a hydrogen donor such as formic acid. Occasionally it may be preferred that one of the substituents $R^3$ be a halogen or another substituent defined above which would be reactive under hydrogenation conditions. In these cases, the compound of general formula 32 is reacted with 1-chloroethyl chloroformate in an inert solvent such as toluene at temperatures between room temperature and 110° C. (Olafson, R. A. et al. *J. Org. Chem.* 1984, 49, 2081). The toluene is then removed, and the residue is heated in methanol for a period of 15–60 minutes, and the product is the debenzylated pyrrolidine of general formula 35. The resulting pyrrolidine 35 is then protected as its tert-butyl carbamate (36) using BOC anhydride in the presence of a base and a suitable solvent. For example, this can be accomplished in a two phase mixture of chloroform and aqueous sodium bicarbonate as shown in reaction Scheme H.

The oxazolidinone chiral auxilliary is next hydrolyzed from the pyrrolidines of general formula 36 as shown at the bottom of reaction Scheme H. The hydrolysis reaction is accomplished using lithium hydroperoxide generated in situ from lithium hydroxide and 30% aqueous hydrogen peroxide. The reaction is typically conducted in a solvent system such as aqueous THF, and the reaction is performed at temperatures between 0° C. and room temperature for a period of 1–6 hours. The resulting carboxylic acids of general formula 37 correspond to carboxylic acids of general formula 2 where both r and s are 1. Using the methodology presented in reaction Scheme A, the compounds of general formula 37 may then be converted to the compounds of the present invention of structural formula I.

Scheme H

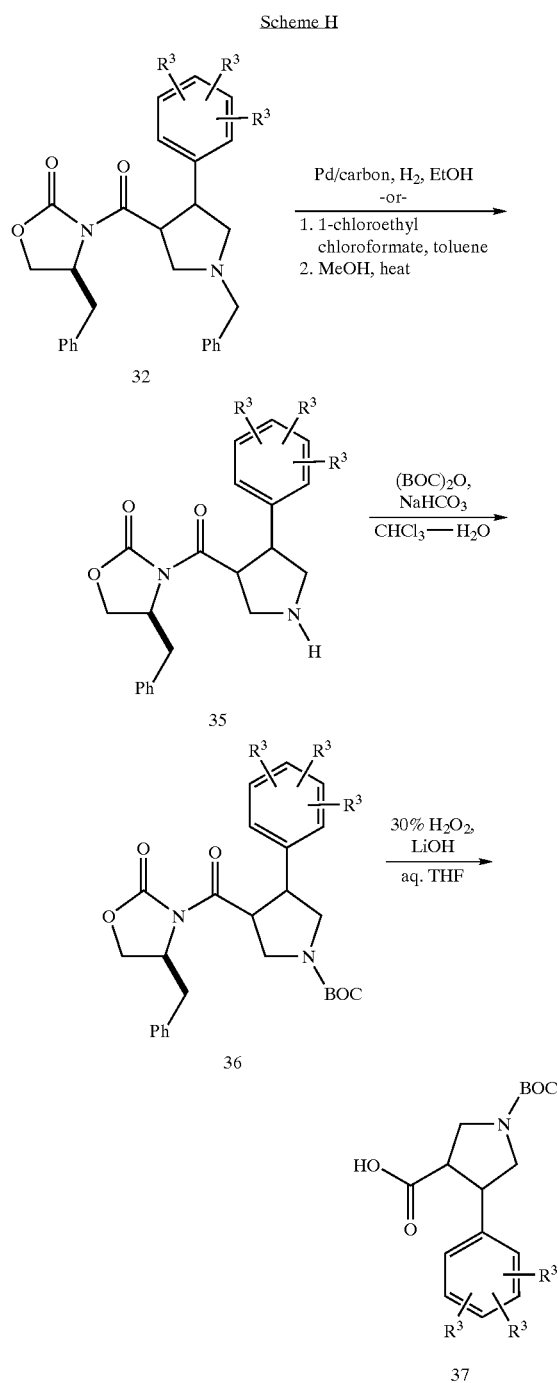

yltrimethylsilane at high temperature and in the absence of solvent affords the N-trimethylsilylmethyl-substituted amine of general formula 38. Subsequent reaction of 38 with aqueous formaldehyde in the presence of methanol and a base such as potassium carbonate then affords the generalized ylid precursor 25 which can be utilized in the cycloaddition reactions discussed above.

Scheme I

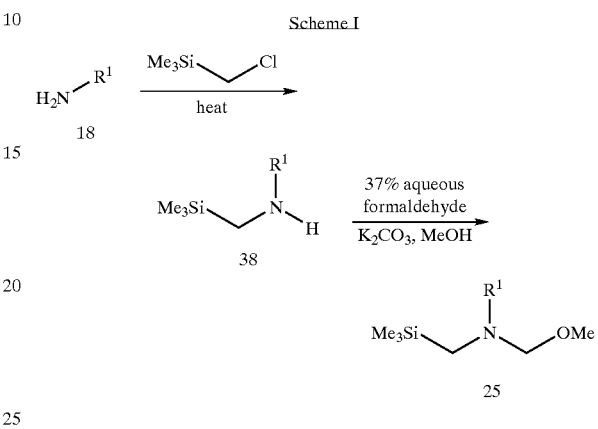

Reaction Schemes J and K illustrate additional methods for the synthesis of the 4-substituted piperidines of general formula 1 which are required in the amide bond coupling step illustrated in reaction Scheme A. As shown in Reaction Scheme J, treatment of an ethanol solution of carboxylic acid 39, wherein R is hydrogen, $C_1$–$C_6$ alkyl or $C_1$–$C_3$ polyfluoroalkyl, with a chlorinating agent such as thionyl chloride at a temperature of 65–78° C., preferably 78° C., for a period of 12–24 hours gives the corresponding ethyl ester derivative 40. Ester 40 can be further reacted with a strong reducing agent such lithium aluminum hydride, diisobutylaluminum hydride or equivalent hydride sources in an inert organic solvent such as tetrahydrofuran at 0–25° C. for a period of 2–12 hours to provide alcohol 41. Hydrogenation of the aromatic ring in 41 is effected by treatment with hydrogen at a pressure of 1500 pounds per square inch in an inert solvent such as acidic methanol at a temperature of 100° C. for a period of 15–24 hours. Suitable catalysts for this hydrogenation reaction include rhodium on alumina and the product is a cyclohexyl substituted derivative of general formula 42. Protection of the amine as the tert-butyl carbamate by treatment with di-tert-butyl dicarbonate and an amine base such as triethylamine, N,N-diisopropylethylamine or the like in an inert organic solvent such as methanol at room temperature for a period of 10–14 hours gives 43.

As noted previously in the discussion of reaction Scheme D, it may occasionally be preferable to incorporate the $R^1$ substituent into the substituted pyrrolidine of general formula 37 at an earlier stage of the synthesis, for instance when it is desired that $R^1$ be a tert-butyl group. In such cases, it is possible to utilize an azomethine ylid precursor (25) bearing the desired $R^1$ substituent in the cycloaddition reactions illustrated in reaction Schemes F and G. Reaction Scheme I illustrates the preparation of azomethine precursors of formula 25 starting with amines of general formula 18. Reaction of the amine of formula 18 with chloromethyltrimethylsilane

Scheme J

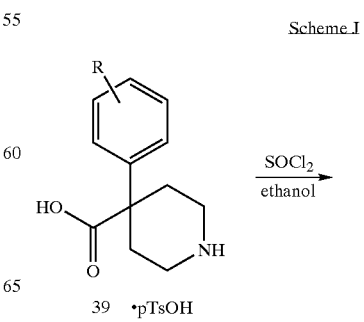

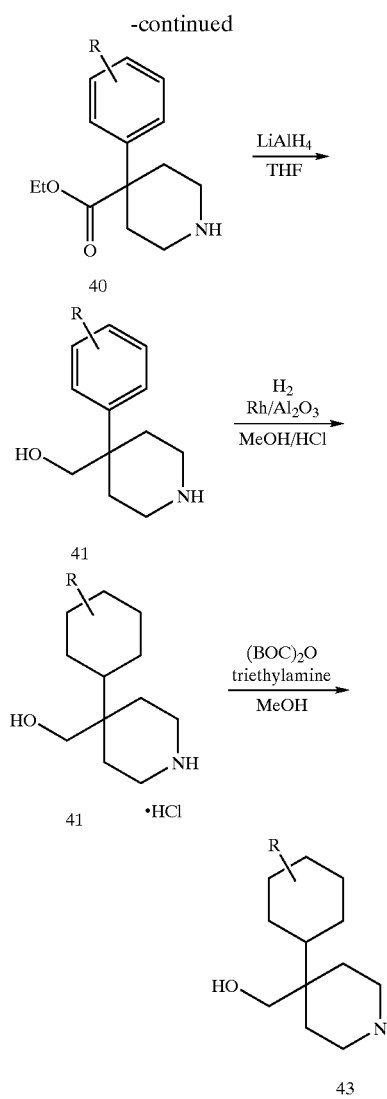

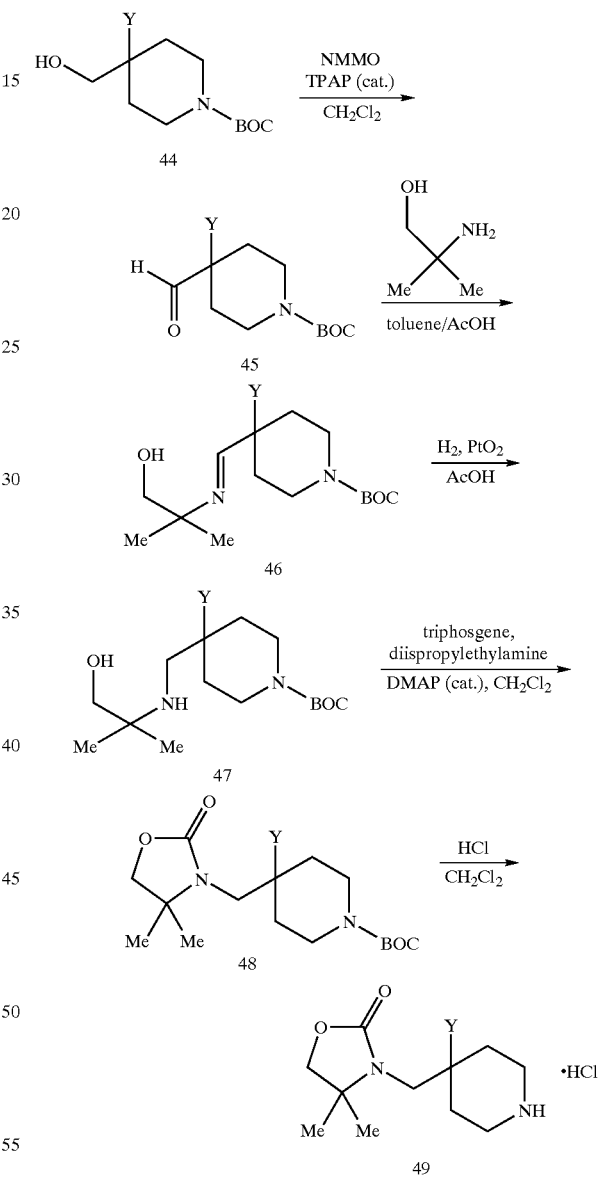

As shown in Reaction Scheme K, alcohols of general formula 44 can be converted to the corresponding aldehydes 45 by treatment with a mild oxidizing agent such as tetra-propylammonium perruthenate (TPAP) in catalytic amounts along with a re-oxidant such as 4-methylmorpholine N-oxide (NMMO) in an inert organic solvent such as methylene chloride at a temperature of 0–25° C. for a period of 2–6 hours. Aldehydes 45 may be condensed with an amine such as 2-amino-2-methyl-1-propanol by mixing the two agents in a solvent such as toluene, benzene or the like along with an acid catalyst such as acetic acid, p-toluenesulfonic acid or the like at refluxing temperature to allow for azeotropic removal of the water formed in the reaction which furnishes imine 46. Reduction of 46 to the amino alcohol 47 can be effected by treatment with hydrogen and an appropriate catalyst such as platinum oxide on carbon, palladium on carbon, palladium hydroxide on carbon or the like with or without an acid catalyst such as acetic acid in an inert organic solvent such as acetic acid, methanol, and ethanol at room temperature for a period of 8–24 hours. Compound 47 can be converted to the corresponding oxazolidinone 48 by treatment with an appropriate acylating agent such as triphosgene along with an amine base such as N,N-diisopropy-lethylmine, triethylamine or the like, and a catalyst such as 4-dimethylaminopyridine in an inert organic solvent such as methylene chloride at a temperature of 0–25° C. for a period of 24 hours. Finally, deprotection of the piperidine nitrogen by treatment with a protic acid such as hydrochloric acid, trifluoroacetic acid or the like in an inert organic solvent such as methylene chloride at or around room temperature for a period of 8–24 hours provides the desired amine 49.

Reaction Scheme L illustrates general methods for the elaboration of an $R^1$ substituent following assembly of a compound of structural formula I (wherein $R^1$=BOC) as described in reaction Scheme A. The N-BOC protected compound of structural formula I is first deprotected under acidic conditions for instance by treatment with hydrochloric acid in ethyl acetate or using trifluoroacetic acid in methylene chloride. The resulting heterocyclic compound of structural formula I ($R^1$=H) may then be subjected to one of several alkylation strategies known in organic chemistry. For instance, compounds (I) (R¹=H) may be utilized in a reductive amination reaction with a suitable carbonyl containing partner (50). The reductive amination is achieved by initial formation of an imine between the amine of formula I (R¹=H) and either an aldehyde or ketone of formula 50. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (I) (R¹=H) may be directly alkylated using an alkylating agent such as 51 in a polar aprotic solvent such as DMF. In this reaction, the substituent Z of compound 51 is a good leaving group such as a halide, mesylate or triflate and the product is the compound of structural formula I bearing the R¹ substituent.

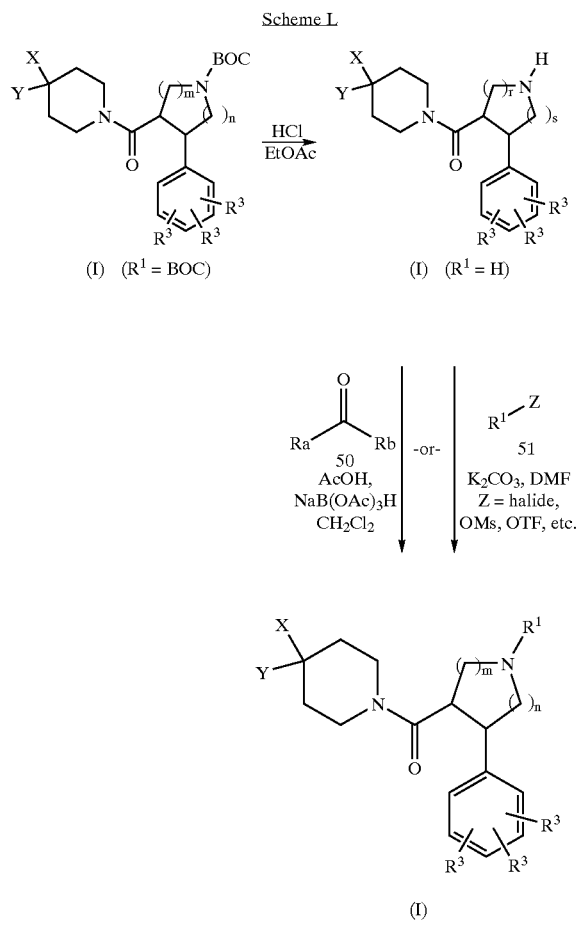

Preparation of 4-Substituted Piperidine Intermediates:

The preparation of other 4-substituted piperidine intermediates of general formula 1 for coupling with the carboxylic acids of general formula 2 as shown in Scheme A below is disclosed in PCT International Application WO 00/74679 (14 Dec. 2000), which is incorporated by reference herein in its entirety. The preparation of additional 4-substituted piperidine intermediates needed to derive the compounds of the present invention is provided below.

PIPERIDINE INTERMEDIATE:

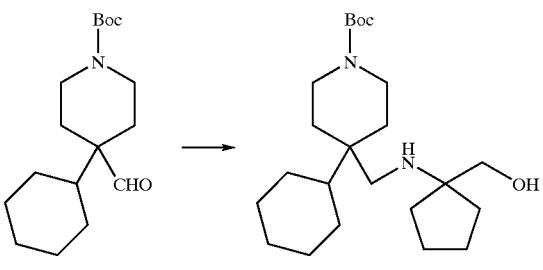

To a solution of 4-cyclohexyl 4-formyl-N-(tertbutyloxycarbonyl)-piperidine (2.56 g, 8.68 mmol) in toluene (100 ml) was added acetic acid (2 ml) and 1-amino-1-cyclopentanemethanol (1.0 g, 8.68 mmol). After refluxing by using a Dean-Stark apparatus for 11 hours, the reaction mixture was concentrated. The residue was dissolved in acetic acid (70 ml) and hydrogenated overnight in the presence of platinum oxide (500 mg) under a balloon atmosphere of hydrogen gas. The catalyst was filtered off and solvent was removed to give a colorless oil, which was dissolved in methanol and made basic by addition of NaOH (5N, 4 ml) and concentrated. The residue was partitioned between water and $CH_2Cl_2$, the two layers separated, and the aqueous layer extracted with $CH_2Cl_2$. The combined organic extracts were washed with brine, dried over $MgSO_4$ and concentrated to give the title compound as a colorless oil (2.1 g).

MS: calc.for $C_{23}H_{42}N_2O_3$: 394.3; Found: 395 (M+1), 417 (M+Na).

PIPERIDINE INTERMEDIATE 2:

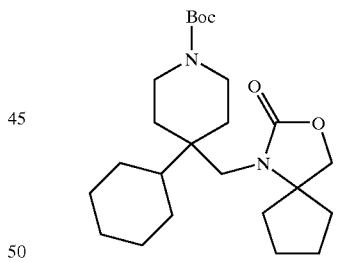

To a solution of Intermediate 1 (2.1 g, 5.33 mmol) in $CH_2Cl_2$ (70 ml) at 0° was added DMAP (0.65 g, 5.33 mmol), DIEA (3.76 ml, 21.3 mmol) followed by slow addition of phosgene (4.1 ml, 8.0 mmol). After stirring the reaction mixture for one hour at 0° C., the ice-water bath was removed and the reaction mixture was continued to stir at room temperature overnight. The mixture was diluted with $CH_2Cl_2$, washed with water and brine, dried over $MgSO_4$ and concentrated to give crude product, which was purified by column chromatography on silica gel (2% $EtOAc/CH_2Cl_2$ to 5% $EtOAc/CH_2Cl_2$) to give the title compound as a white solid (1.2 g).

MS: calc.for $C_{24}H_{40}N_2O_4$: 420.3; Found: (M+1), (M+Na).

PIPERIDINE INTERMEDIATE 3:

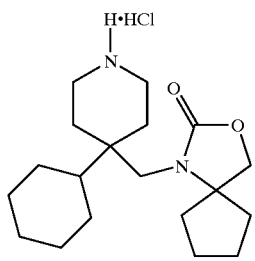

To the Intermediate 2 (1.2 g) was added hydrogen chloride (4.0 M in dioxane). The reaction mixture was stirred at room temperature for 30 minutes and the solvent was removed in vacuo to afford the title compound (1.2 g).

MS: calc.for $C_{19}H_{32}N_2O_2$: 320.3; Found: 321.1 (M+H).

PIPERIDINE INTERMEDIATE 4:

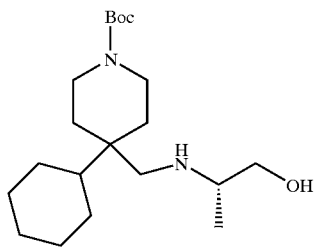

Intermediate 4 was prepared from (S)-(+)-2-amino-1-propanol in an analogous manner to the one described for the preparation of Intermediate 1.

MS: calc.for $C_{20}H_{38}N_2O_3$: 354; Found: 355 (M+H).

PIPERIDINE INTERMEDIATE 5:

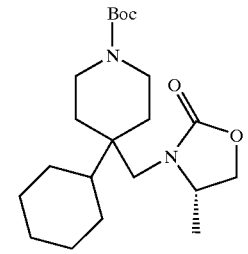

Intermediate 5 was prepared from Intermediate 4 in an analogous manner to the one described for the preparation of Intermediate 2.

MS: calc. for $C_{21}H_{36}N_2O_4$: 380.3; Found: 381 (M+H).

PIPERIDINE INTERMEDIATE 6:

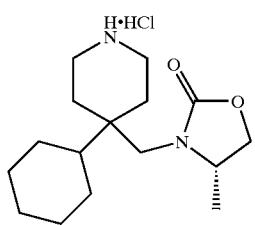

Intermediate 6 was prepared from Intermediate 5 in an analogous manner to the one described for the preparation of Intermediate 3.

MS: calc. for $C_{16}H_{28}N_2O_2$: 280.3; Found: 281 (M+H).

PIPERIDINE INTERMEDIATE 7:

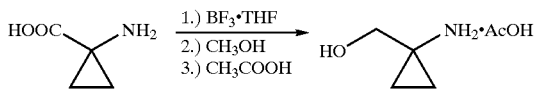

To a suspension of 1-aminocyclopropane-1-carboxylic acid (2.8 g, 27.7 mmol) in THF (20 ml) was added borane-tetrahydrofuran complex (100 ml, 100 mmol) slowly under nitrogen at room temperature. The reaction mixture was stirred at 70° C. overnight, then cooled to 0° C. After addition of methanol (12.2 ml, 300 mmol), the mixture was allowed to stir for 30 minutes. Then acetic acid (1.6 ml, 27.7 mmol) was added. The reaction mixture was concentrated to provide the title compound as a colorless oil (3.0 g).

PIPERIDINE INTERMEDIATE 8:

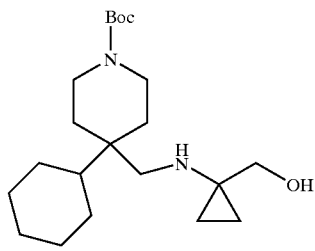

Intermediate 8 was prepared from Intermediate 7 in an analogous manner to the one described for the preparation of Intermediate 1.

MS: calc. for $C_{21}H_{38}N_2O_3$: 366.3; Found: 367 (M+H).

PIPERIDINE INTERMEDIATE 9:

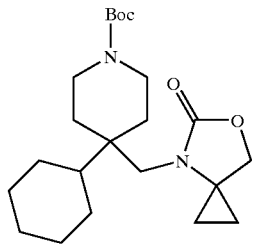

To a solution of Intermediate 8 (0.8 g, 2.18 mmol) in $CH_2Cl_2$ (40 ml) at 0° was added DMAP (0.266 g, 2.18 mmol), DIEA (1.52 ml, 8.74 mmol) and triphosgene (0.648 g, 2.18 mmol). After stirring the reaction mixture for one hour at 0° C., the ice-water bath was removed and the reaction mixture was allowed to stir at r.t. overnight. The mixture was diluted with $CH_2Cl_2$, washed with water and brine, dried over $MgSO_4$ and concentrated to give crude product, which was purified by column chromatography on silica gel (10% $CH_2Cl_2$/EtOAc) to give the title compound as a colorless oil (0.13 g).

ESI-MS: calc. for $C_{22}H_{36}N_2O_4$: 392; Found: 393 (M+1).

PIPERIDINE INTERMEDIATE 10:

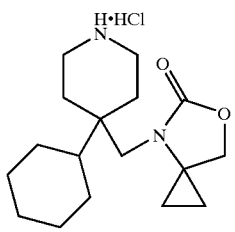

Intermediate 10 was prepared from Intermediate 9 in an analogous manner to the one described for the preparation of Intermediate 3.

MS: calc. for $C_{17}H_{28}N_2O_2$: 292.2; Found: 293 (M+H).

PIPERIDINE INTERMEDIATE 11:

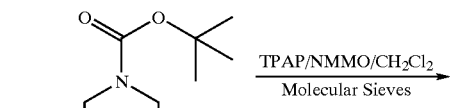

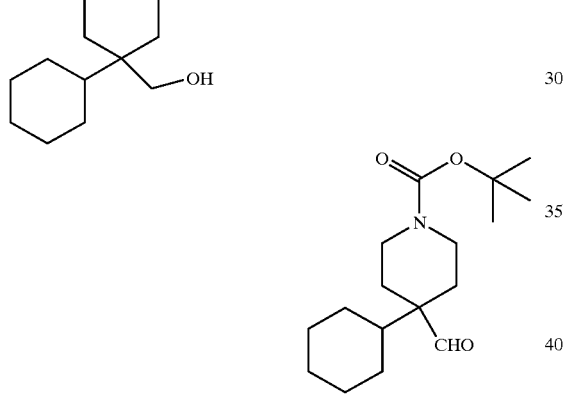

To a solution of the alcohol (9.41 g, 31.6 mmol) in $CH_2Cl_2$ (100 ml) at 0° C. containing molecular sieves (2 g) and 4-methylmorpholine N-oxide (NMMO) (4.449 g, 37.98 mmol) was added TPAP (1.12 g, 3.16 mmol). After stirring the reaction mixture at 0° C. for 0.5 h, the reaction mixture was warmed to room temperature and stirred further for 5 hrs. The reaction mixture was concentrated to half the volume, diluted with hexane (250 ml), filtered through a silica gel pad and concentrated to give pure title compound (9.4 g).

PIPERIDINE INTERMEDIATE 12:

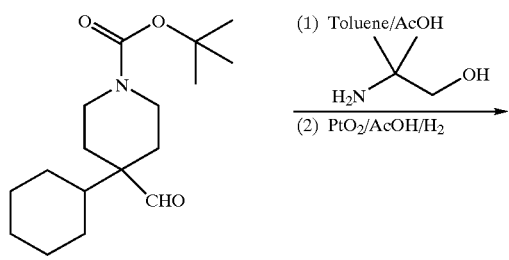

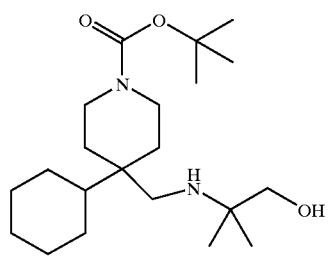

To a solution of the aldehyde (2 g, 6.7 mmol) in toluene (50 ml) was added acetic acid (500 µl). After stirring the reaction mixture at reflux temperature using Dean Stark apparatus for 8 hrs, the mixture was concentrated and dissolved in acetic acid (30 ml). To the mixture was added $PtO_2$ (500 mg) which was stirred under an atmosphere of $H_2$ overnight. The reaction mixture was flushed with nitrogen, filtered and concentrated to give the title compound (2 g).

PIPERIDINE INTERMEDIATE 13:

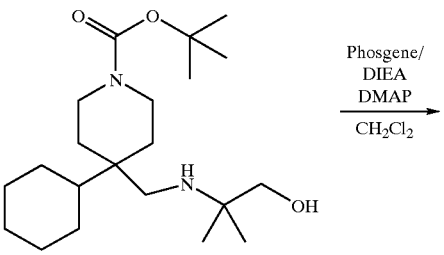

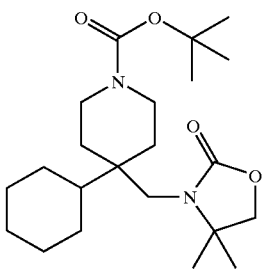

To a solution of the amino alcohol (4.96 g, 13.47 mmol) in $CH_2Cl_2$ at 0° C. containing DIEA (6.98 g, 53.9 mmol), DMAP (1.64 g, 13.47 mmol) was added slowly a toluene solution of phosgene (1.93M, 10.47 ml, 20.21 mmol). After stirring the reaction mixture for 1 hr at 0° C., the temperature was raised to room temperature and stirred further for 2 hrs. The reaction mixture was diluted with $CH_2Cl_2$, washed with water, brine, dried and concentrated. The residue was purified by column chromatography over silica gel (5% EtOAc/ $CH_2Cl_2$) to give pure product (3.95 g).

PIPERIDINE INTERMEDIATE 14:

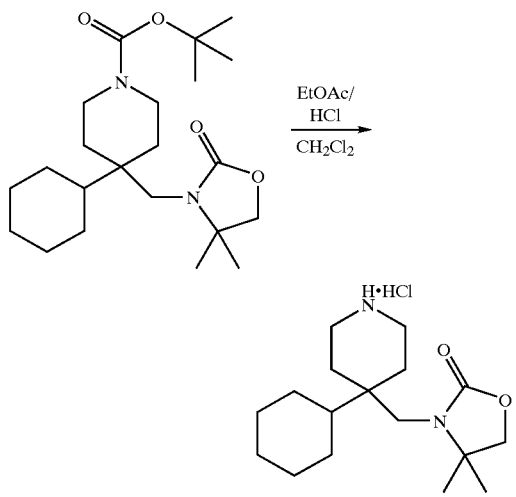

To a solution of Intermediate 13 (3.95 g) in CH$_2$Cl$_2$ was added 5 ml of a saturated HCl solution in EtOAc. After stirring the reaction mixture for 30 min at room temperature, the solvent was removed and the residue lyophilized from a benzene/methanol solution to afford the title compound (3.85 g).

Scheme M

PIPERIDINE INTERMEDIATE 15:

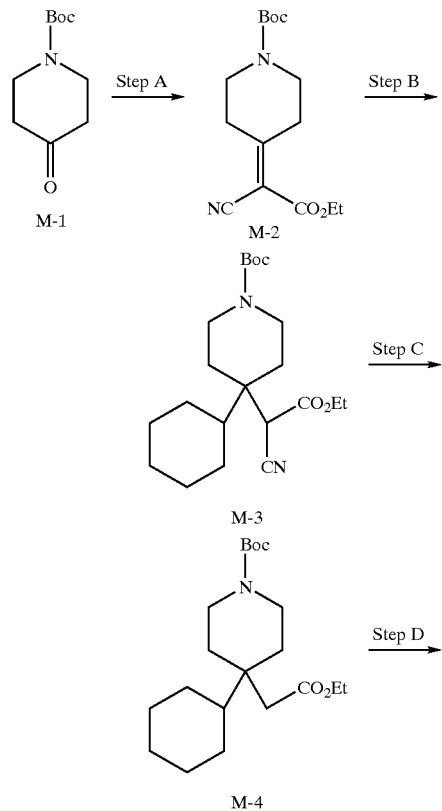

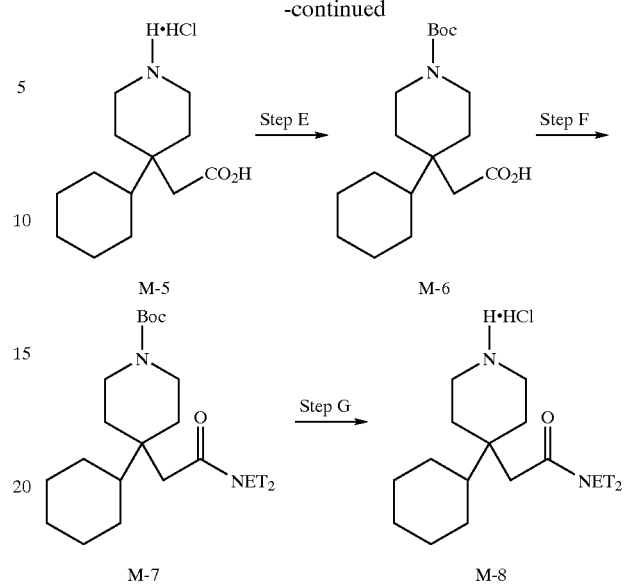

Step A

To a 500-mL round-bottom flask equipped with a Dean Stark trap and magnetic stirrer was added 1-Boc-4-piperidone (M-1) (20.0 g, 100 mmol), cyanoacetic acid ethyl ester (10.6 mL, 100 mmol), NH$_4$OAc (0.77 g, 10 mmol), HOAc (0.57 mL, 10 mmol), and benzene (200 mL). The mixture was stirred at reflux temperature overnight. After cooling to room temperature, the volatiles were removed under reduced pressure, and the residue was purified by flash column chromatography with 20% EtOAc in hexane as eluent to give M-2 as white solid (21.6 g).

ESI-MS: Calcd. for C$_{15}$H$_{22}$N$_2$O$_4$: 294; Found: 317 (M$^+$+Na).

Step B

To a suspension of CuCN (3.28 g, 36.3 mmol) in dry THF (100 mL) was added cyclohexylmagnesium chloride (36.6 mL, 73.2 mmol, 2.0 N in ether). The resulting suspension was stirred at -50° C. for 30 min and then warmed up to room temperature. After stirring for 1 h, a solution of compound M-1 (5.40 g, 18.3 mmol) in 50 mL of THF was cannulated into the mixture over 2 min. The mixture was stirred at -50° C. for 1 h and then kept at -25° C. overnight. The mixture was slowly warmed to -10° C. and quenched with saturated aqueous NH$_4$Cl (50 mL) and water (50 mL), extracted with EtOAc (2×250 mL). The combined organic extracts were washed three times with water, 1 N HCl, saturated aqueous NaHCO$_3$, dried over MgSO$_4$, filtered, and evaporated to give compound M-3 as a colorless oil (7.12 g).

ESI-MS: Calcd. for C$_{21}$H$_{34}$N$_2$O$_4$: 378; Found: 401 (M$^+$+Na).

Step C

A mixture of M-3 (6.91 g, 18.3 mmol), LiCl (1.09 g, 25.6 mmol), water (1.40 mL), and DMSO (100 mL) was stirred at 160° C. for 1 h. After cooling to room temperature, the mixture was poured into water (800 mL) and extracted with Et$_2$O (4×250 mL). The combined organic layers were washed with brine, dried over anhydrous Na$_2$SO$_4$, filtered, and concentrated. The residue was purified by flash column chromatography with 20% EtOAc in hexane as eluent to give compound M-4 as a colorless oil (2.83 g).

ESI-MS: Calcd. for $C_{18}H_{30}N_2O_2$: 306; Found: 329 ($M^+$+Na).

Step D

To a solution of 4.0 N HCl in dioxane (30 mL, 120 mmol) was added M-4 (2.60 g, 8.48 mmol). The mixture was stirred at room temperature for 1 h and the volatiles were removed under reduced pressure. The residue was dissolved in a concentrated HCl (100 mL). The mixture was stirred overnight at reflux temperature. After cooling to room temperature, the volatiles were removed under reduced pressure to give the compound M-5 as a yellow solid (2.42 g).

ESI-MS: Calcd. for $C_{13}H_{23}NO_2$: 225; Found: 226 ($M^+$+1)

Step E

To a solution of compound M-5 (1.91 g, 8.48 mmol) in dioxane (50 mL) and water (50 mL, containing 5.0 mL 5.0 N NaOH, 25 mmol) was added di-tert-butyl dicarbonate (2.22 g, 10.2 mmol). The mixture was stirred at room temperature for 4 h and the volatiles were removed under reduced pressure. The residue was quenched with a mixture of EtOAc (200 mL) and 1 N HCl (50 mL). The layers were separated and the aqueous layer was extracted three times with EtOAc. The combined organic layers were dried over anhydrous $Na_2SO_4$, filtered, and evaporated to give M-6 as a white solid (2.97 g).

ESI-MS: Calcd. for $C_{18}H_{31}NO_4$: 325; Found: 326 ($M^+$+1)

Step F

Compound M-6 (1.0 g, 3.07 mmol) was dissolved in 30 mL of methylene chloride, and then diethylamine (0.38 mL, 3.68 mmol), DMAP (0.037 g, 0.307 mmol), EDC (1.18 g, 6.14 mmol) were added. The resulting mixture was stirred at room temperature overnight, and then diluted with 20 mL of $CH_2Cl_2$ and washed with 20 mL of 1N HCl solution, 20 mL of saturated $NaHCO_3$ solution, 20 mL of $H_2O$, and 20 mL of saturated NaCl solution. The organic phase was dried over $MgSO_4$, filtered, and evaporated to give M-7 (1.16 g).

ESI-MS: Calcd. for $C_{22}H_{40}N_2O_3$: 380; Found: 381 ($M^+$+1)

Step G

To a solution of 4.0 N HCl in dioxane (30 mL, 120 mmol) was added M-7 (1.16 g, 3.07 mmol). The mixture was stirred at room temperature for 1 h and the volatiles were removed under reduced pressure to give M-8 (0.99 g).

ESI-MS: Calcd. for $C_{17}H_{32}N_2O$: 280; Found: 281 ($M^+$+1)

Scheme N

PIPERIDINE INTERMEDIATE 16:

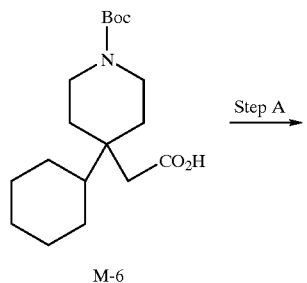

M-6

Step A

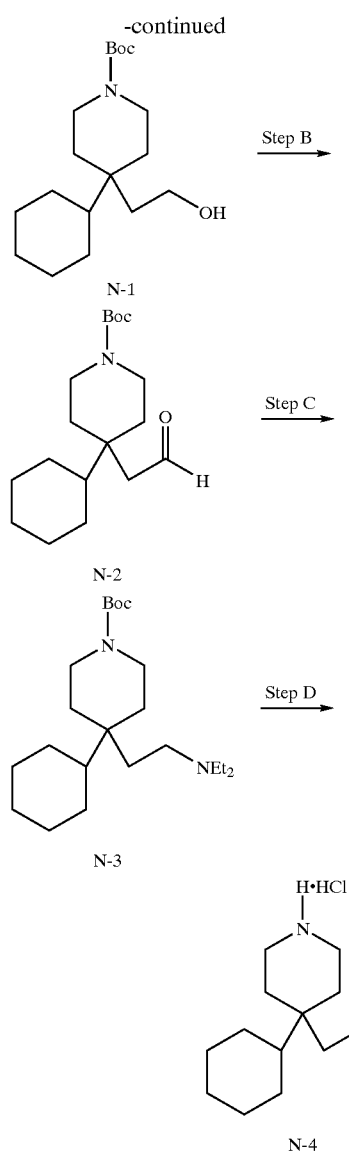

Step A

To a solution of M-6 (0.18 g, 0.554 mmol) in 8.0 mL of dry THF was added borane-dimethyl sulfide complex (1.10 mL, 2.0 N in THF, 2.20 mmol). The mixture was stirred overnight and then quenched with MeOH. The volatiles were removed under reduced pressure to give N-1 (0.11 g).

ESI-MS: Calcd. for $C_{18}H_{33}NO_3$: 311; Found: 334 ($M^+$+Na).

Step B

To a suspension of N-1 (0.11 g, 0.347 mmol), 4-methylmorpholine N-oxide (0.049 mg, 0.416 mmol), and molecular sieve in dry methylene chloride (5.0 mL) was added tetrapropylammonium perruthenate (0.012 g, 0.035 mmol). After stirring for 30 min, the mixture was filtered through a pad of silica gel and washed with ether. The organic solution was evaporated to give compound N-2 as an oil (0.11 g).

ESI-MS: Calcd. for $C_{18}H_{31}NO_3$: 309; Found: 332 ($M^+$+Na).

Step C

To a solution of N-2 (0.11 g, 0.35 mmol) in 3.0 mL of methylene chloride was added diethylamine (0.072 mL, 0.70 mmol) and molecular sieves. After stirring for about 5 min, Na(OAc)$_3$BH (0.22 mg, 1.05 mmol) was added and the mixture was stirred for 6 h at room temperature. After filtration of molecular sieves, the mixture was diluted with methylene chloride, washed twice with saturated aqueous NaHCO$_3$ solution, dried over anhydrous Na$_2$SO$_4$, filtered, and evaporated to give N-3 (0.080 g).

ESI-MS: Calcd. for $C_{22}H_{42}N_2O_2$: 366; Found: 367 (M$^+$+1).

Step D

To a solution of 4.0 N HCl in dioxane (10 mL, 40 mmol) was added compound N-3 (0.080 g, 0.218 mmol). The mixture was stirred at room temperature for 1 h and the volatiles were removed under reduced pressure to give N4 (0.075 g).

ESI-MS: Calcd. for $C_{17}H_{34}N_2$: 266; Found: 227 (M$^+$+1)

Scheme O

PIPERIDINE INTERMEDIATES 17–21:

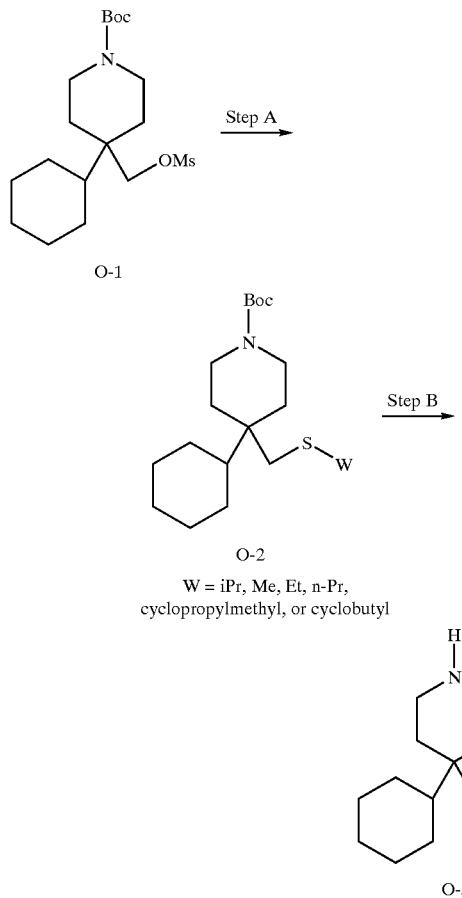

W = iPr, Me, Et, n-Pr, cyclopropylmethyl, or cyclobutyl

Step A

To a stirred solution of tert-butyl 4-cyclohexyl-4-{[(methylsulfonyl)oxy]methyl}piperidine-1-carboxylate (O-1) (3 g, 8.0 mmol) in DMF (30 mL) at room temperature was added sodium 2-methyl-2-propanethiolate (0.78 g, 8.0 mmol). The resultant suspension was stirred at 60° C. for 18 h and then poured into water (150 mL) and extracted with diethyl ether (3×100 mL). The combined organic extracts were washed with brine, dried over Na$_2$SO$_4$ and concentrated. Flash chromatography over silica (5% EtOAc in hexane) yielded O-2 (W=iPr) as a clear colorless oil (2.4 g).

Mass Spectrum (ESI): calcd for $C_{20}H_{37}NO_2S$: 355.25; Found: 378 (M$^+$+Na).

Step B

To a stirred solution of O-2 (W=iPr) (2.4 g, 6.7 mmol) in methylene chloride (10 mL) at room temperature was added HCl (5N in dioxane) (50 mL). The resultant solution was stirred at room temperature for 1 h. Volatiles were removed in vacuo to furnish O-3 (W=iPr) as a clear colorless gum (1.9 g).

Mass Spectrum (ESI): calcd for $C_{15}H_{29}NS$: 255.20; Found: 256 (M$^+$+1).

The piperidine intermediates O-3 (W=Me, Et, n-Pr, cyclopropylmethyl, and cyclobutyl) were prepared in an analogous manner to the one described for the preparation of 4-cyclohexyl-4-[(isopropylthio)methyl]piperidinium chloride (O-3, W=iPr).

O-3 (W=Et): Mass Spectrum (ESI): calcd for $C_{14}H_{27}NS$: 241.19; Found: 242 (M$^+$+1).

O-3 (W=Me): Mass Spectrum (ESI): calcd for $C_{13}H_{25}NS$: 227.17; Found: 228 (M$^+$+1).

O-3 (W=n-Pr): Mass Spectrum (ESI): calcd for $C_{15}H_{29}NS$: 255.20; Found: 256 (M$^+$+1).

O-3 (W=cyclopropylmethyl): Mass Spectrum (ESI): calcd for $C_{16}H_{29}NS$: 267.20; Found: 268 (M$^+$+1).

O-3 (W=cyclobutylthio): Mass Spectrum (ESI): calcd for $C_{16}H_{29}NS$: 267.20; Found: 268 (M$^+$+1).

Scheme P

PIPERIDINE INTERMEDIATES 22:

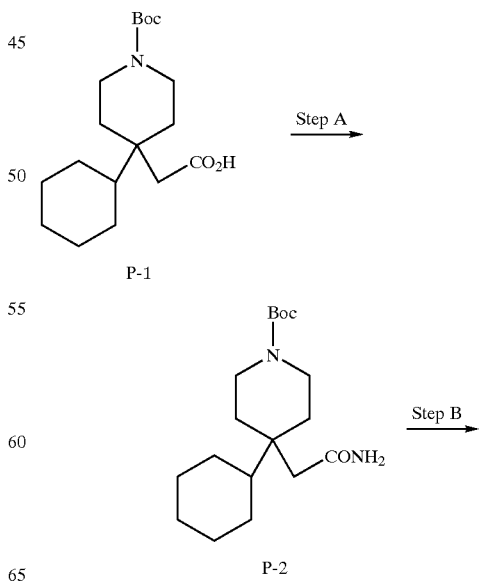

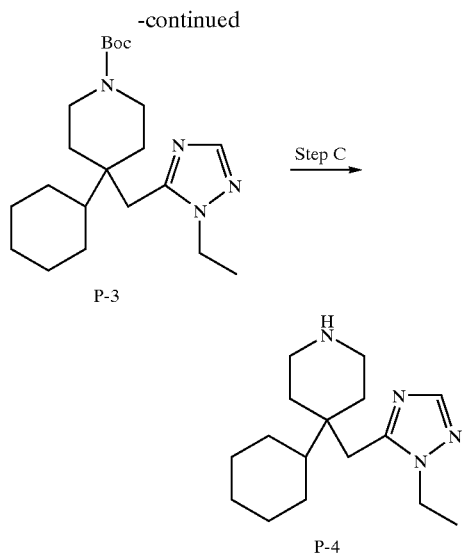

P-3

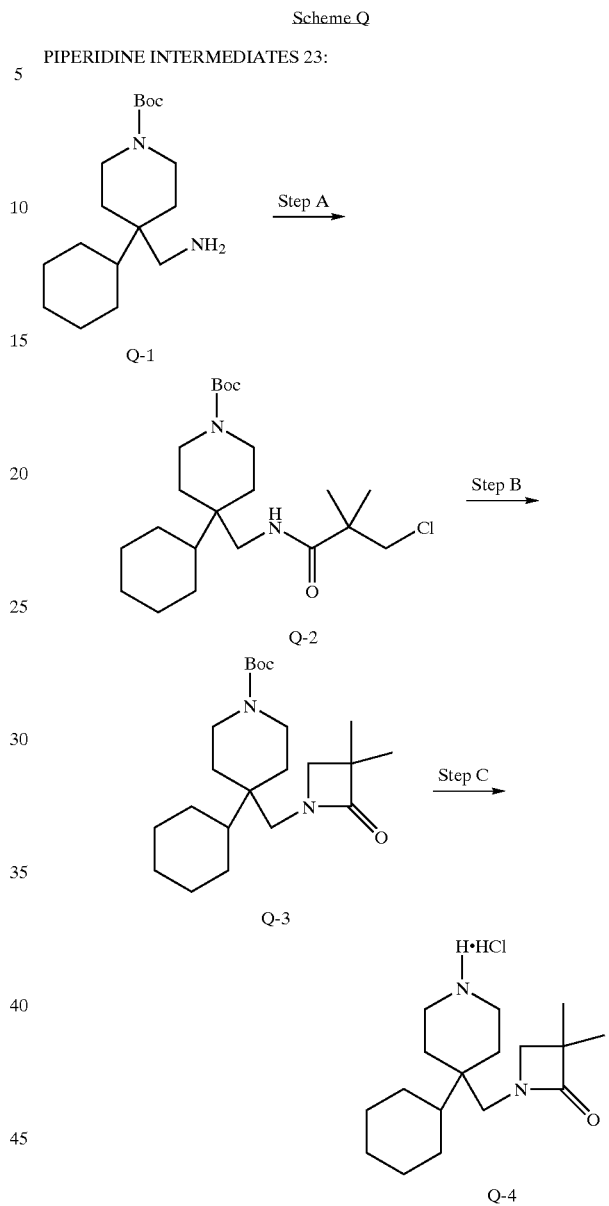

Scheme Q

PIPERIDINE INTERMEDIATES 23:

Step A

To a solution of P-1 (0.745 g, 2.072 mmol) in methylene chloride (40 mL) at 0° C. was added DMF (1 mL) followed by the dropwise addition of oxalyl chloride (1.14 mL of 2M solution in methylene chloride, 2.28 mmol). The reaction was warmed to room temperature over one h, then re-cooled to 0° C. before transferring to a rapidly stirring saturated aqueous ammonium hydroxide solution (15 mL). The resulting mixture was then poured into methylene chloride (40 mL) and diluted with 1N NaOH (40 mL). The layers were separated and the aqueous phase was extracted three times with methylene chloride. The combined organics were then washed with water and brine, dried (sodium sulfate) and the volatiles removed in vacuo. Flash chromatography over silica (25% acetone/methylene chloride) yielded P-2 as a white foam (0.615 g).

Mass Spectrum (ESI): calcd for $C_{21}H_{30}N_2O_3$: 358.23; Found 359 (M$^+$+1).

Step B

A solution of P-2 (0.150 g, 0.84 mmol) in N,N-dimethylformamide dimethyl acetal (1 mL) was refluxed at 120° C. for 2 h, then cooled to room temperature. The reaction was then concentrated and the residue was dissolved in acetic acid (1 mL). Ethyl hydrazine was then added and the reaction was heated at 95° C. for 3.5 h. The volatiles were then removed in vacuo and the reaction was partitioned between sodium bicarbonate and ethyl acetate. The organics were collected, washed with water and brine, dried (sodium sulfate), and the volatiles removed in vacuo. Purification by flash chromatography (0–15% acetone in methylene chloride) yielded P-3 as a pale yellow oil (79 mg).

Mass Spectrum (ESI): calcd for $C_{24}H_{34}N_4O_2$: 410.27; Found 411 (M$^+$+1).

Step C

To a solution of P-3 (79 mg) in methylene chloride was added 30% HBr in acetic acid (5 mL) and the reaction was stirred for two hours. The volatiles were removed, and the reaction was partitioned between 1N NaOH and methylene chloride. The organics were dried (sodium sulfate) and evaporated to afford P-4 as an oil (59 mg). Mass Spectrum (ESI): calcd for $C_{16}H_{28}N_4$: 276.23; Found 277 (M$^+$+1).

Step A

To a stirred solution of Q-1 (1.33 g, 4.5 mmol) in methylene chloride (12 mL) was added DMAP (0.14 g, 1.1 mmol) and 3-chloropivaloyl chloride (0.87 g, 5.6 mmol). The mixture was stirred 1 h, diluted with methylene chloride, washed with 1N HCl, the organic layer dried over MgSO$_4$ and the solvent removed in vacuo to provide 2.1 g of Q-2 as an oil. ESI-MS calc. for $C_{22}H_{39}ClN_2O_3$: 414; Found 415 (M+H).

Step B

To a stirred solution of Q-1 (2.25 g, 5.42 mmol) in DMF (15 mL) was added NaH (0.52 g, 21.7 mmol) and heated to 70° C. for 16 h. The mixture was quenched with MeOH and then water. The mixture was concentrated, diluted with EtOAc, washed with 2N HCl, brine, dried over MgSO$_4$ and evaporated. The product was purified by preparative HPLC (C18, 20×100 mm, 50–100% acetonitrile) to provide 850 mg of Q-3 as a yellow solid. ESI-MS calc. for $C_{22}H_{38}N_2O_3$: 378; Found 379 (M+H).

Step C

Compound Q-3 (1.05 g, 1.92 mmol) was treated with HCl-EtOAc solution at room temperature for 30 min. The mixture was evaporated to provide 690 of Q-4 as a solid. ESI-MS calc. for $C_{17}H_{30}N_2O$: 278; Found 279 (M+H).

Scheme R

PIPERIDINE INTERMEDIATES 24:

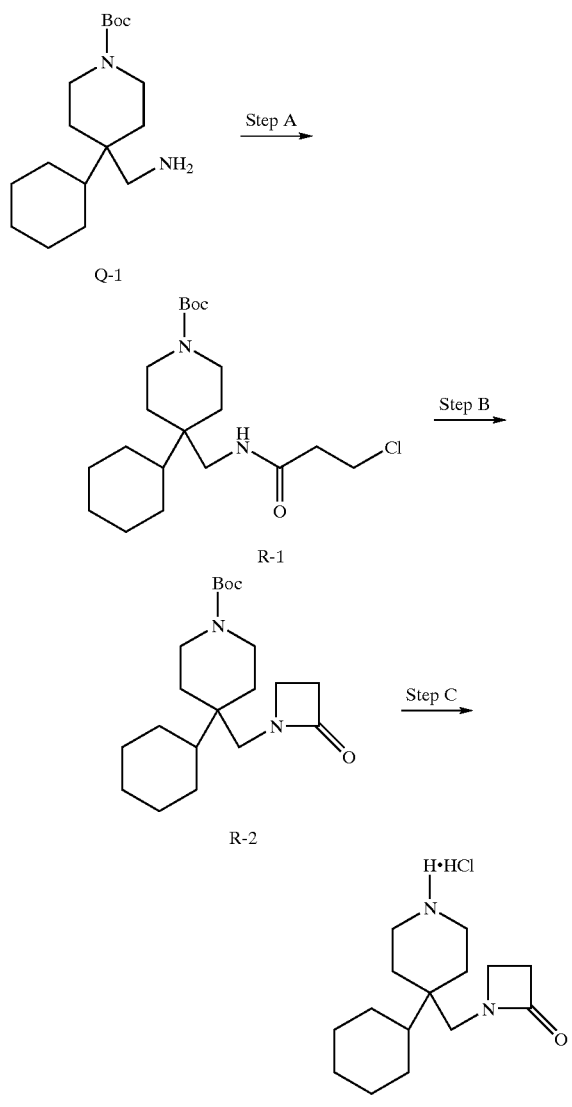

Step A

Compound R-1 was synthesized in a manner similar as Q-2, but using 3-chloropropionyl chloride. ESI-MS calc. for $C_{20}H_{35}ClN_2O_3$: 386; Found 387 (M+H).

Step B

Compound R-2 was synthesized from R-1 in a manner similar as Q-3. ESI-MS calc. for $C_{20}H_{34}N_2O_3$: 350; Found 351 (M+H).

Step C

Compound R-3 was synthesized from R-2 in a manner similar as Q-4. ESI-MS calc. for $C_{15}H_{26}N_2O$: 250; Found 251 (M+H).

Scheme S

PIPERIDINE INTERMEDIATES 25:

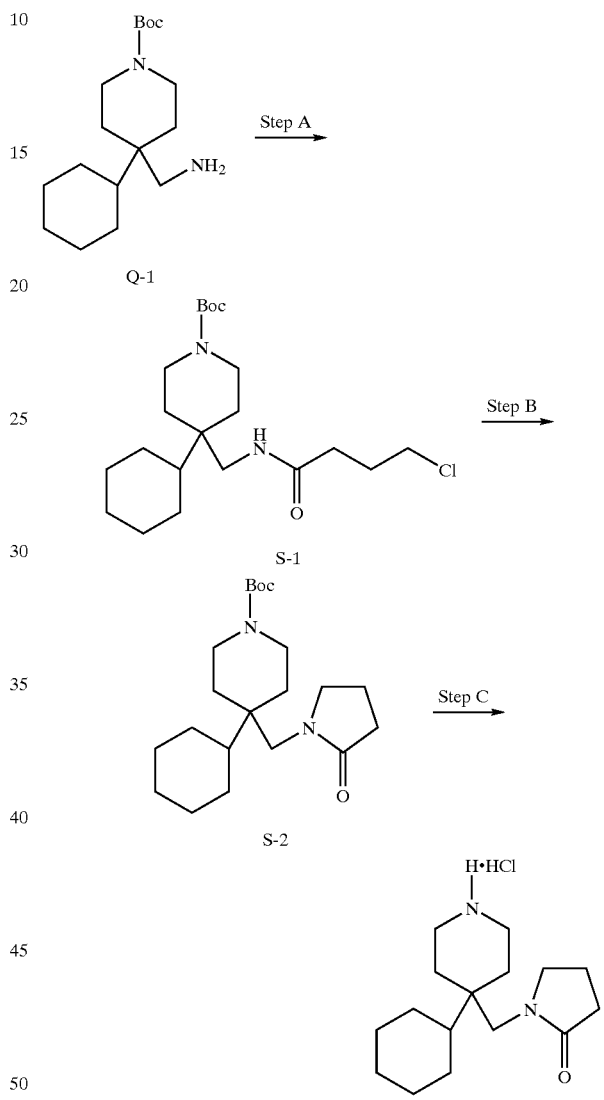

Step A

Compound S-1 was synthesized in a manner similar as Q-2, but using 4-chlorobutyryl chloride. ESI-MS calc. for $C_{21}H_{37}ClN_2O_3$: 400; Found 401 (M+H).

Step B

Compound S-2 was synthesized from S-2 in a manner similar to Q-3. ESI-MS calc. for $C_{21}H_{36}N_2O_3$: 364; Found 365 (M+H).

Step C

Compound S-3 was synthesized from S-2 in a manner similar to Q-4. ESI-MS calc. for $C_{16}H_{28}N_2O$: 264; Found 265 (M+H).

Scheme T

PIPERIDINE INTERMEDIATES 26:

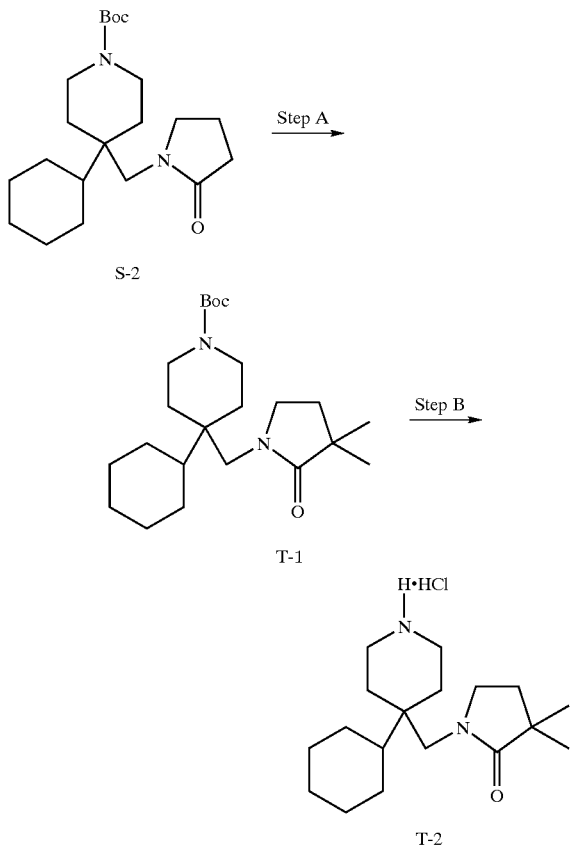

Step A

To a stirred solution of S-2 (2.3 g, 6.3 mmol) in THF (20 mL) cooled to −78° C. was added lithium diisopropylamide (LDA) (2M solution in THF) (3 eq) slowly via syringe over 20 min and stirring was continued for 1 h. Iodomethane was added and the mixture was stirred for 1 h. The reaction mixture was warmed to room temperature and stirring was continued an additional 30 min. Subsequently, the reaction mixture was cooled again to −45° C. and another 1.5 eq. of LDA added, the mixture was stirred 15 min, then an additional 1 eq. of iodomethane was introduced to the reaction mixture and the stirring continued 1 h. The reaction was quenched with water, concentrated and partitioned between EtOAc/2N HCl, washed with brine, dried over $MgSO_4$, filtered and concentrated. The residue was chromatographed (silica, 1:4 EtOAc/hexane) to provide 720 mg of T-1 as a white solid. ESI-MS calc. for $C_{23}H_{40}N_2O_3$: 392; Found 393 (M+H).

Step B

Compound T-2 was prepared from T-1 in a manner similar to Q-4. ESI-MS calc. for $C_{18}H_{32}N_2O$: 292; Found 293 (M+H).

The following Examples are provided to illustrate the invention and are not to be construed as limiting the scope of the invention in any manner.

EXAMPLE 1

(±)-trans4-({4-Cyclohexyl-4-[(4,4-dimethyl-2-oxo-1,3-oxazolidin-3-yl)methyl]piperidin-1-yl}carbonyl)-3-(4-fluorophenyl)-1-methylpiperidinium trifluoroacetate Step A; Preparation of tert-butyl (±)-trans-4-({4-cyclohexyl-4-[(4,4-dimethyl-2-oxo-1,3-oxazolidin-3-yl)methyl]piperidin-1-yl}carbonyl)-3-(4-fluorophenyl)piperidine-1-carboxylate 1-(3-Dimethylaminopropyl)-3-ethylcarbodiimide hydrochloride (47.7 mg, 0.249 mmol) was added to a stirred mixture of 4-cyclohexyl-4-[(4,4-dimethyl-2-oxo-1,3-oxazolidin-3-yl)methyl]piperidinium chloride (54.9 mg, 0.166 mmol), (±)-trans-1-(tert-butoxycarbonyl)-3-(4-fluorophenyl)-piperidine-4-carboxyl acid (70.7 mg, 0.216 mmol), 1-hydroxy-benzotriazole (33.6 mg, 0.249 mmol) and N-methylmorpholine (54.8 μL, 0.498 mmol) in methylene chloride (2.1 mL) at ambient temperature. After approximately 18 h, the reaction mixture was poured into saturated aqueous sodium bicarbonate and extracted three times with methylene chloride. The combined organic extracts were washed with brine, dried ($Na_2SO_4$) and concentrated in vacuo. The crude residue was used without further purification in the subsequent reaction.

Step B: Preparation of (±)-trans-4-({4-cyclohexyl-4-[(4,4-dimethyl-2-oxo-1,3-oxazolidin-3-yl)methyl]piperidin-1-yl}carbonyl)-3-(4-fluorophenyl)piperidinium trifluoroacetate A saturated solution of hydrogen chloride in ethyl acetate (2.0 mL) was added to a solution of crude product from step A in methylene chloride (1.0 mL) at room temperature. After 18 h, the volatiles were evaporated in vacuo, and the crude residue purified by preparative reversed phase high pressure liquid chromatography on a YMC Pack Pro C18 column (gradient elution: 0–100% acetonitrile/water as eluent, 0.1% TFA as modifier) to give the title compound as an off-white solid [MS: m/z 500 (MH$^+$)].

Step C: Preparation of (±)-trans-4-({4-cyclohexyl-4-[(4,4-dimethyl-2-oxo-1,3-oxazolidin-3-yl)methyl]piperidin-1-yl}carbonyl)-3-(4-fluorophenyl)-1-methylpiperidinium trifluoroacetate Sodium cyanoborohydride (12.6 mg, 0.200 mmol) was added to a vigorously stirred suspension of the product of step B (20.0 mg, 0.040 mmol), paraformaldehyde (20.0 mg), 4 Å sieves (20.0 mg) and acetic acid (45.8 μL, 0.800 mmol) in tetrahydrofuran/methanol (1:3, 400 μL) at ambient temperature. After 18 h, the reaction mixture was poured into saturated aqueous sodium bicarbonate and extracted three times with methylene chloride. The combined organic extracts were washed with brine, dried (Na$_2$SO$_4$) and concentrated in vacuo. Purification of the crude residue by preparative reversed phase high pressure liquid chromatography on YMC Pack Pro C18 column (gradient elution; 0–100% acetonitrile/water as eluent, 0.1% TFA as modifier) provided the title compound (12 mg) as an off-white solid (12.0 mg); MS: m/z 514 (MH$^+$).

Following a procedure similar to that described above for Example 1, the following compounds can be prepared:

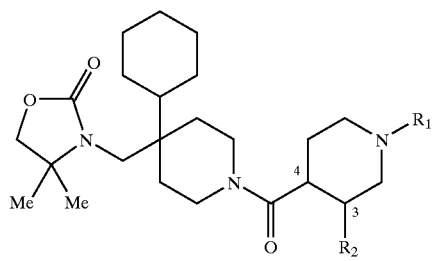

| Ex. # | Relative stereo. (3,4) | R$^1$ | R$^2$ | Parent Ion m/z |
|---|---|---|---|---|
| 2 | trans (RS,RS) | —H | 4-fluorophenyl | 500 |
| 3 | trans (S,S) | —H | 4-fluorophenyl | 500 |
| 4 | trans (R,R) | —H | 4-fluorophenyl | 500 |
| 5 | trans (RS,RS) | —CH$_2$C(O)Ot-Bu | 4-fluorophenyl | 614 |
| 6 | trans (RS,RS) | —CH$_2$C(O)OH | 4-fluorophenyl | 558 |
| 7 | trans (R,R) | isopropyl | 4-fluorophenyl | 542 |
| 8 | trans (R,R) | methyl | 4-fluorophenyl | 514 |
| 9 | trans (R,R) | n-propyl | 4-fluorophenyl | 542 |
| 10 | trans (R,R) | ethyl | 4-fluorophenyl | 528 |
| 11 | trans (R,R) | CH(CH$_3$)CH$_2$OMe | 4-fluorophenyl | 572 |
| 12 | trans (RS,RS) | —H | 4-chlorophenyl | 516 |
| 13 | trans (RS,RS) | —H | 4-methoxyphenyl | 512 |
| 14 | trans (S,S) | methyl | 4-chlorophenyl | 530 |
| 15 | trans (R,R) | methyl | 4-chlorophenyl | 530 |
| 16 | trans (RS,RS) | —H | 4-methylphenyl | 496 |
| 17 | trans (RS,RS) | —H | 4-(4'-chlorophenyl)phenyl | 592 |
| 18 | trans (RS,RS) | isopropyl | 4-chlorophenyl | 558 |
| 19 | trans (R,R) | isopropyl | 4-chlorophenyl | 559 |
| 20 | trans (S,S) | isopropyl | 4-chlorophenyl | 559 |
| 21 | trans (RS,RS) | cyclobutyl | 4-chlorophenyl | 570 |
| 22 | trans (RS,RS) | n-propyl | 4-chlorophenyl | 558 |
| 23 | trans (RS,RS) | ethyl | 4-chlorophenyl | 544 |
| 24 | trans (R,R) | —C(=NH)NH$_2$ | 4-fluorophenyl | 543 |
| 25 | trans (R,R) | —C(=NH)NH$_2$ | 4-chlorophenyl | 559 |
| 26 | trans (R,R) | —CH$_2$CH$_2$NH$_2$ | 4-chlorophenyl | 560 |
| 27 | trans (R,R) | —CH$_2$CH$_2$NH$_2$ | 4-fluorophenyl | 544 |
| 28 | trans (RS,RS) | —H | 4-chloro-3-fluorophenyl | 534 |
| 29 | trans (RS,RS) | isopropyl | 4-chloro-3-fluorophenyl | 576 |
| 30 | trans (R,R) | —C(=NH)CH$_3$ | 4-fluorophenyl | 541 |
| 31 | trans (RS,RS) | —H | 3-chloro-4-fluorophenyl | 535 |
| 32 | trans (RS,RS) | isopropyl | 3-chloro-4-fluorophenyl | 577 |
| 33 | trans (RS,RS) | ethyl | 3-chloro-4-fluorophenyl | |
| 34 | trans (RS,RS) | —H | 2,4-dichlorophenyl | 551 |
| 35 | trans (RS,RS) | isopropyl | 2,4-dichlorophenyl | 593 |
| 36 | trans (RS,RS) | —H | 3,4-dichlorophenyl | 551 |
| 37 | trans (RS,RS) | isopropyl | 3,4-dichlorophenyl | 593 |
| 38 | trans (RS,RS) | —H | 2,4-difluorophenyl | 519 |
| 39 | trans (RS,RS) | isopropyl | 2,4-difluorophenyl | 561 |
| 40 | trans (RS,RS) | ethyl | 2,4-difluorophenyl | 546 |
| 41 | trans (RS,RS) | —H | 3,4-difluorophenyl | 519 |
| 42 | trans (RS,RS) | isopropyl | 3,4-difluorophenyl | 560 |
| 43 | trans (RS,RS) | ethyl | 3,4-difluorophenyl | 546 |

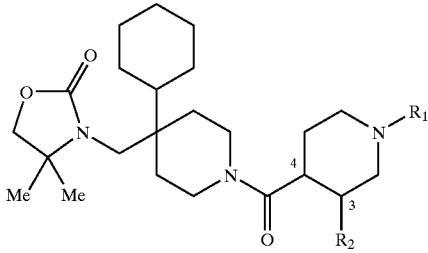

| Ex. # | Relative stereo. (3,4) | R$^1$ | R$^2$ | Parent Ion m/z |
|---|---|---|---|---|
| 44 | trans (RS,RS) | —H | 4-chloro-2-fluorophenyl | 535 |
| 45 | trans (RS,RS) | isopropyl | 4-chloro-2-fluorophenyl | 577 |
| 46 | trans (RS,RS) | ethyl | 4-chloro-2-fluorophenyl | 562 |
| 47 | trans (R,R) | —CH$_2$CF$_3$ | 4-chlorophenyl | 582 |
| 48 | trans (R,R) | —CH(CH$_3$)CH$_2$CH$_3$ | 4-fluorophenyl | 556 |
| 49 | trans (RS,RS) | —CH$_2$CH$_2$N(CH$_3$)$_2$ | 4-chlorophenyl | 587 |

EXAMPLE 50

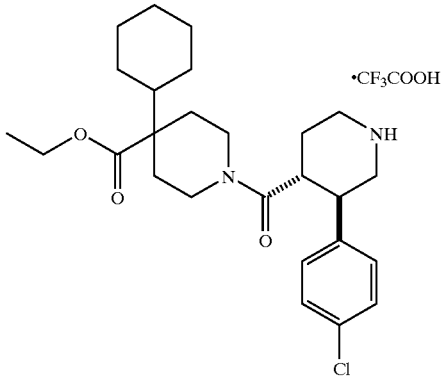

(±)-trans-3-(4-Chlorophenyl)4{-[4-cyclohexyl-4-(ethoxycarbonyl)piperidin-1yl]carbonyl}-1-isopropylpiperidinium trifluoroacetate Step A: Preparation of 4-(ethoxycarbonyl)-3-oxopiperidinium chloride A mixture of ethyl 1-benzyl-3-oxopiderine-4-carboxylate hydrochloride (20.0 g, 67.0 mmol) and 10% Pd/C (2.00 g; Degussa Type E101) in ethanol/water (1:1; 300 mL) was hydrogenated at 50 psi for 4 h. The resulting mixture was filtered through celite® and the filtrate evaporated in vacuo to give the title compound as a brown solid (67.0 mmol).

Step B: Preparation of 1-tert-butyl 4-ethyl 3-oxopiperidine-1,4-dicarboxylate

Di-tert-butyl-dicarbonate (17.5 g, 80.4 mmol) was added in one portion to a stirred mixture of the crude product of step A (67.0 mmol), sodium bicarbonate (6.20 g, 73.7 mmol) and sodium chloride (11.7 g, 201 mmol) in water/chloroform (1:2; 300 mL) and the resulting mixture heated at 60° C. for 3 h. After cooling to room temperature, the organic phase was separated and the aqueous phase extracted three times with chloroform. The combined organic extracts were washed with brine, dried (MgSO$_4$) and concentrated in vacuo. The crude residue (27.1 g) was used without further purification in the subsequent reaction.

Step C: Preparation of 1-tert-butyl 4-ethyl 5-{[(trifluoromethyl)-sulfonyl]oxy}-3,6-dihydropyridine-1,4(2H)-dicarboxylate Trifluoromethanesulfonic anhydride (12.4 mL, 73.7 mmol) was added over approximately 0.1 h, via syringe, to a stirred solution of the product of step B (27.1 g, 67.0 mmol) and N,N-diisopropylethylamine (14.0 mL, 80.4 mmol) in methylene chloride (250 mL) at −78° C. After allowing to warm to ambient temperature overnight, the reaction mixture was quenched with saturated aqueous sodium bicarbonate, poured into water and extracted three times with methylene chloride. The combined organic extracts were washed with brine, dried (MgSO$_4$) and concentrated in vacuo. Purification of the residue by flash chromatography on silica gel (gradient elution; 0–20% ethyl acetate/hexanes as eluent) afforded the title compound as an amber colored oil (17.6 g).

Step D: Preparation of 1-tert-butyl 3-ethyl 4-(4-chlorophenyl)-5,6-dihydropyridine-1,3(2H)-dicarboxylate A vigorously stirred suspension of the product of step C (1.00 g, 2.48 mmol), 4-chlorophenylboronic acid (0.427 g, 2.73 mmol) and [1,1'-bis(diphenylphosphino)-ferrocene]dichloropalladium(II) (0.102 g, 0.124 mmol) in toluene/ethanol (3:2; 24.0 mL) was degassed via three vacuum/nitrogen ingress cycles and then heated to approximately 80° C. Aqueous 2 M sodium carbonate (3.10 mL, 6.20 mmol) was added dropwise via syringe and the resulting mixture maintained at reflux overnight. After cooling to ambient temperature, the reaction mixture was diluted with ethyl acetate and filtered through celite®. The filtrate was poured into water and extracted three times with ethyl acetate. The combined organic extracts were washed with brine, dried (MgSO$_4$) and concentrated in vacuo. Purification of the residue by medium pressure liquid chromatography on silica gel (gradient elution; 0–15% ethyl acetate/hexanes as eluent) furnished the title compound as a colorless oil (0.828 g).

Step E: Preparation of (±)-1-tert-butyl 3-ethyl 4-(4-chlorophenyl)piperidine-1,3-dicarboxylate Magnesium metal (1.23 g, 51.0 mmol) was added in three portions over approximately 0.3 h to a stirred solution of the product of step D (1.85 g, 5.1 mmol) in methanol (40 mL) at ambient temperature. After stirring overnight, the reaction mixture was poured into 1 N hydrochloric acid (100 mL) and extracted three times with ethyl acetate. The combined organic extracts were washed with saturated sodium bicarbonate, brine, dried (MgSO$_4$) and concentrated in vacuo. Purification of the residue by medium pressure liquid chromatography on silica gel (gradient elution; 0–25% ethyl acetate/hexanes as eluent) provided the title compound (mixture of cis/trans diastereoisomers) as a colorless oil (1.5 g).

Step F: Preparation of (±)-trans-1-(tert-butoxycarbonyl)-3-(4-chlorophenyl)piperidine-4-carboxylic acid Excess sodium metal was added to a stirred solution of the product of step E (1.5 g, 4.1 mmol) in methanol (20 mL) at ambient temperature, and the resulting solution heated to 75° C. After approximately 1 h, 5 M sodium hydroxide (5.0 mL) was added and the reaction mixture heated to 100° C. for an additional hour. After cooling to room temperature, the reaction mixture was acidified to pH 5 with 2 N hydrochloric acid and extracted three times with methylene chloride. The combined organic extracts were washed with brine, dried (MgSO$_4$) and concentrated in vacuo, to give the title compound as a colorless solid (1.3 g). The crude product was used without further purification in the subsequent reaction.

Step G: Preparation of (±)-trans-3-(4-chlorophenyl)-4-{[4-cyclohexyl-4-(ethoxycarbonyl)piperidin-1-yl]carbonyl}piperidinium trifluoroacetate 1-(3-Dimethylaminopropyl)-3-ethylcarbodiimide hydrochloride (0.034 g, 0.177 mmol) was added to a stirred mixture of the crude product of step F (0.040 g, 0.118 mmol), 4-cyclohexyl-4-(ethoxycarbonyl)piperidinium chloride (0.049 g, 0.177 mmol), 1-hydroxybenzotriazole (0.024 g, 0.177 mmol) and N-methylmorpholine (0.020 mL, 0.177 mmol) in methylene chloride (0.5 mL) at ambient temperature. After approximately 18 h, the reaction mixture was poured into water/saturated sodium bicarbonate (1:1) and extracted three times with methylene chloride. The combined organic extracts were washed with brine, dried (Na$_2$SO$_4$) and concentrated in vacuo. A saturated solution of hydrochloric acid in ethyl acetate (1.0 mL) was added to a solution of the crude amide in methylene chloride (1.0 mL) at room temperature. After 18 h, the volatiles were evaporated in vacuo, and the crude residue purified by preparative reversed phase high pressure liquid chromatography on YMC Pack Pro C18 phase (gradient elution; 0–100% acetonitrile/water as eluent, 0.1% TFA as modifier) to give the title compound (0.034 g) as an off-white solid [MS: m/z 461 (MH$^+$)].

Step H: Preparation of (±)-trans-3-(4-chlorophenyl)-4-{[4-cyclohexyl-4-(ethoxycarbonyl)piperidin-1-yl]carbonyl}-1-isopropylpiperidinium trifluoroacetate Sodium triacetoxyborohydride (34.5 mg, 0.163 mmol) was added to a stirred solution of the product of step G (25.0 mg, 54.2 mmol), acetone (23.9 mL, 0.325 mmol) and acetic acid (9.3 mL, 0.163 mmol) in methylene chloride (0.5 mL) at ambient temperature. After 18 h, the reaction mixture was poured into saturated aqueous sodium bicarbonate and extracted three times with methylene chloride. The combined organic extracts were washed with brine, dried (Na$_2$SO$_4$) and concentrated in vacuo. Purification of the residue by preparative reversed phase high pressure liquid chromatography on YMC Pack Pro C18 phase (gradient elution; 0–100% acetronirile/water as eluent, 0.1% TFA as modifier) afforded the title compound as an off-white solid [MS: m/z 503 (MH$^+$)].

Following a procedure sirnilar to that described above for Example 50, the following compounds can be prepared:

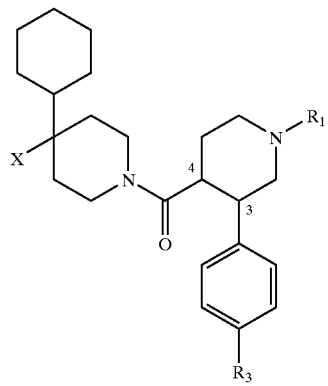
| Ex. # | Relative stereo. (3,4) | R¹ | R³ | X | Parent Ion m/z |
|---|---|---|---|---|---|
| 51 | trans (RS,RS) | —H | —F | Me-C(Me)(Me)-NH-C(=O)-Me | 472 |
| 52 | trans (R,R) | —H | —F | Me-C(Me)(Me)-NH-C(=O)-Me | 472 |
| 53 | trans (RS,RS) | —H | —Cl | Me-C(Me)(Me)-NH-C(=O)-Me | 488 |
| 54 | trans (RS,RS) | —H | —F | Me-CH2-O-C(=O)-Me | 445 |
| 55 | trans (S,S) | —H | —F | Me-CH2-O-C(=O)-Me | 445 |
| 56 | trans (R,R) | —H | —F | Me-CH2-O-C(=O)-Me | 445 |
| 57 | trans (RS,RS) | —H | —F | Me-CH(Me)-S-Et | 461 |
| 58 | trans (RS,RS) | —H | —F | Me-CH(Me)-S(=O)2-Et | 493 |
| 59 | trans (RS,RS) | —H | —F | 1-ethyl-1,2,4-triazole | 454 |
| 60 | trans (R,R) | —H | —F | 1-ethyl-1,2,4-triazole | 454 |

-continued

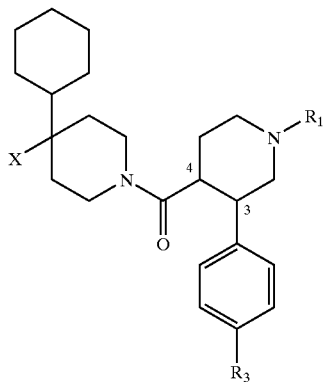

| Ex. # | Relative stereo. (3,4) | R¹ | R³ | X | Parent Ion m/z |
|---|---|---|---|---|---|
| 61 | trans (RS,RS) | —H | —Cl | 1-ethyl-1,2,4-triazole | 470 |
| 62 | trans (R,R) | —H | —F | (4S)-4-methyl-3-ethyl-oxazolidin-2-one | 486 |
| 63 | trans (RS,RS) | —H | —Cl | N-(isopropyl)-N-ethyl methanesulfonamide | 538 |
| 64 | trans (RS,RS) | methyl | —Cl | N-(isopropyl)-N-ethyl methanesulfonamide | |
| 65 | trans (RS,RS) | —H | —H | ethyl acetate | 427 |
| 66 | trans (R,R) | isopropyl | —F | ethyl acetate | 487 |
| 67 | trans (RS,RS) | isopropyl | —Cl | N-(tert-butyl)acetamide | 530 |
| 68 | trans (R,R) | isopropyl | —F | N-(tert-butyl)acetamide | 514 |
| 69 | trans (R,R) | isopropyl | —F | 1-ethyl-1,2,4-triazole | 496 |

-continued
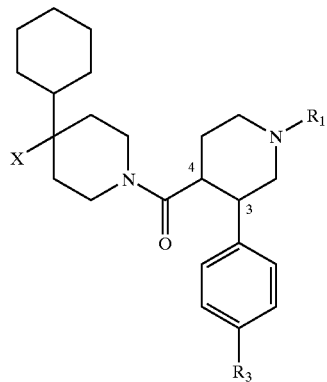
| Ex. # | Relative stereo. (3,4) | R¹ | R³ | X | Parent Ion m/z |
|---|---|---|---|---|---|
| 70 | trans (S,S) | —H | —F | Me—CH₂—O—C(=O)—CH₂— | 471 |
| 71 | trans (RS,RS) | —H | —Cl | Me—CH₂—O—C(=O)—CH₂— | 461 |
| 72 | trans (RS,RS) | —H | —CF₃ | Me—CH₂—O—C(=O)—CH₂— | 495 |
| 73 | trans (RS,RS) | —H | —CF₃ | Me₃C—NH—C(=O)—CH₂— | 522 |
| 74 | trans (RS,RS) | —H | —CF₃ | 1-ethyl-1,2,4-triazol-3-yl | 504 |
| 75 | trans (R,R) | —H | —F | pyrrolidinyl-C(=O)—CH₂— | 470 |
| 76 | trans (RS,RS) | —H | —Cl | pyrrolidinyl-C(=O)—CH₂— | 486 |
| 77 | trans (R,R) | 2-pyrimidinyl | —F | pyrrolidinyl-C(=O)—CH₂— | 548 |
| 78 | trans (R,R) | —H | —F | morpholinyl-C(=O)—CH₂— | 486 |

-continued
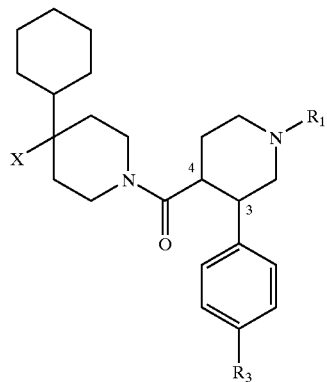
| Ex. # | Relative stereo. (3,4) | R¹ | R³ | X | Parent Ion m/z |
|---|---|---|---|---|---|
| 79 | trans (RS,RS) | —H | —Cl | acetyl morpholine | 502 |
| 80 | trans (R,R) | —H | —F | 4-methylpiperazinyl acetyl | 499 |
| 81 | trans (RS,RS) | —H | —Cl | 4-methylpiperazinyl acetyl | 515 |
| 82 | trans (R,R) | —H | —F | N-(pyridin-4-yl)acetamide | 493 |
| 83 | trans (R,R) | —H | —F | N-benzylacetamide | 507 |
| 84 | trans (R,R) | —H | —F | N-(1-hydroxy-2-methylpropan-2-yl)acetamide | 488 |
| 85 | trans (RS,RS) | —H | —F | 2-(ethylthio)pyrimidine | 497 |
| 86 | trans (RS,RS) | —H | —F | 2-ethoxypyrimidine | 481 |

EXAMPLE 87

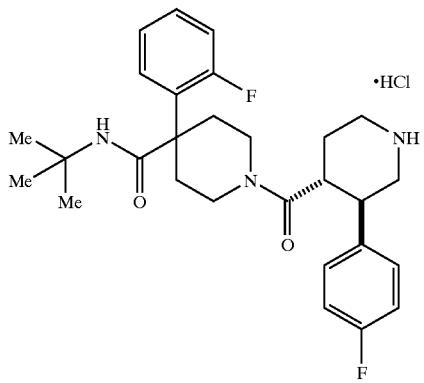

(3R,4R)-4-{[4-[(Tert-butylamino)carbonyl]-4-(2-fluorophenyl)piperidin-1-yl]carbonyl}-3-(4-fluorophenyl)piperidinium chloride Step A: Preparation of 4-(2-fluorophenyl)-1-methylpiperidine-4-carbonitrile N-Methyl-bis-(2'-chloroethyl)amine hydrochloride (8.36 g; 43.1 mmol) was suspended in 60 mL of methylene chloride followed by the addition of 1 eq. of triethylamine (6.0 mL). After 45 min, the mixture was filtered on a medium-pore fritted Buchner funnel to remove the triethylammonium chloride salt. The filtrate was concentrated in vacuo resulting in the precipitation of additional salt. The filtration was repeated 2 more times to provide pure N-methyl-bis-(2'-chloroethyl)amine. The amine was combined with (2-fluorophenyl)acetonitrile (8.01 g; 43.1 mmol) and tetra-n-butylammonium sulfate (1.46 g; 4.31 mmol) followed by the addition of toluene (15 mL). To this solution was added 12.5 N sodium hydroxide dropwise over 10 min. The reaction mixture was heated to 75° C. until the starting material had been consumed, poured into $H_2O$ (100 mL) and extracted three times with 200 mL methylene chloride. The combined organic extracts were washed with brine, dried ($Na_2SO_4$), filtered and concentrated in vacuo. The crude residue was purified on silica gel by first elution with 50:50 ethyl acetate/hexanes followed by 95:5 methylene chloride/methanol (containing 10% v/v ammonium hydroxide) to provide the titled compound Step B: Preparation of 4-carboxy-4-(2-fluorophenyl)-1-methyl-piperidinium chloride The product of Step A (4.5 g; 20.6 mmol) was heated to 135° C. in concentrated hydrochloric acid (25 mL). The volatiles were removed in vacuo which provided the crude product. The residue was suspended in toluene (20 mL) and heated under reduced pressure to remove the toluene. This process was repeated three times which furnished the title compound as a powder.

Step C: Preparation of N-(tert-butyl)-4-(2-fluorophenyl)-1-methyl-piperidine-4-carboxamide To a suspension of the product of the previous step (1.0 g; 3.63 mmol) in methylene chloride (15 mL) was added 4 drops of N,N-dimethylformamide and the mixture was cooled to 0° C. A solution of oxalyl chloride (2.0 M in methylene chloride; 1.25 eq; 2.27 mL) was added dropwise over 10 min. After an additional 30 min at 0° C., the reaction mixture was allowed to warm to ambient temperature for 2 h at which time tert-butyl amine (5 eq.; 1.92 mL) was added dropwise. The resultant mixture was maintained at room temperature for 18 h and then quenched with a saturated solution of sodium bicarbonate. The aqueous layer was extracted three times with methylene chloride. The combined extracts were washed with brine, dried ($Na_2SO_4$), filtered and concentrated in vacuo. The crude residue was purified on silica gel and eluted with 95:5 methylene chloride/methanol (containing 10% v/v ammonium hydroxide) which provided 550 mg of the title compound.

Step D: Preparation of N-(tert-butyl)-4-(2-fluorophenyl)piperidine-4-carboxamide To a solution of the product of step C (550 mg; 1.88 mmol) in toluene (10 mL) was added 1-chloroethyl chloroformate (15 mmol; 1.62 mL) and the reaction was heated to reflux for 36 h. The volatiles were removed in vacuo, the crude carbamate was then dissolved in methanol (10 mL) and the resultant solution was heated to reflux for 2 h. The volatiles were removed in vacuo, the crude amine was dissolved in methylene chloride (100 mL) and the solution was washed with a saturated solution of sodium bicarbonate, brine and the compound dried ($Na_2SO_4$). The drying agent was removed by filtration and the volatiles were removed in vacuo to furnish the crude product which was purified on silica gel using a gradient elution (95:5 then 90:10 methylene chloride/methanol (containing 10% v/v ammonium hydroxide) to afford the title compound.

Step E: Preparation of (3R,4R)-4-{[4-[(tert-butylamino)carbonyl]-4-(2-fluorophenyl)piperidin-1-yl]carbonyl}-3-(4-fluorophenyl)-piperidinium chloride The product of step D (70 mg) was combined with (3R,4R)-1-(tert-butoxycarbonyl)-3-(4-fluorophenyl)piperidine-4-carboxylic acid (0.1971 mmol; 55 mg), 1-(3-dimethylaminopropyl)-3-ethylcarbodiimide hydrochloride (57 mg) and 1-hydroxybenzotriazole (40 mg) to which methylene chloride (2.5 mL) was added. The reaction mixture was maintained at ambient temperature for 24 h. The reaction mixture was diluted with methylene chloride (100 mL), washed with a saturated solution of sodium bicarbonate, brine and dried ($Na_2SO_4$). The drying agent was removed by filtration and the volatiles were removed in vacuo to furnish the crude N-BOC protected product which was purified on silica gel (eluted with 50:50 to 75:25 ethyl acetate:hexane). The N-BOC protected product was dissolved in ethyl acetate (2 mL) and a saturated solution of hydrogen chloride in ethyl acetate (2 mL) was added. The reaction mixture was maintained at ambient temperature for 90 min. The volatiles were removed in vacuo, the crude product was triturated twice with diethyl ether, and the purified product was dried in vacuo to provide 55 mg of the title compound [MS: m/z 484 ($MH^+$)].

Following a procedure similar to that described above for Example 87, the following compounds were prepared:

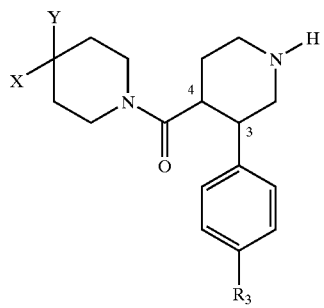

| Ex. # | Relative stereo. (3,4) | R³ | X | Y | Parent Ion m/z |
|---|---|---|---|---|---|
| 88 | trans (RS,RS) | —F | phenyl | phenyl | 443 |
| 89 | trans (RS,RS) | —F | phenyl | —H | 367 |
| 90 | trans (RS,RS) | —F | benzyl | —H | 381 |
| 91 | trans (S,S) | —F | methyl acetate | benzyl | 439 |
| 92 | trans (S,S) | —F | methyl acetate | —CH₂CH=CH₂ | 389 |
| 93 | trans (S,S) | —F | methyl acetate | methyl | 363 |
| 94 | trans (S,S) | —F | methyl acetate | —H | 349 |
| 95 | trans (S,S) | —F | t-butyl acetamide | phenyl | 466 |
| 96 | trans (RS,RS) | —Cl | t-butyl acetamide | 2-fluorophenyl | 500 |
| 97 | trans (R,R) | —F | morpholinyl acetyl | 2-fluorophenyl | 498 |
| 98 | trans (RS,RS) | —Cl | morpholinyl acetyl | 2-fluorophenyl | 514 |
| 99 | trans (R,R) | —F | t-butyl acetamide | 4-iodophenyl | 592 |

-continued

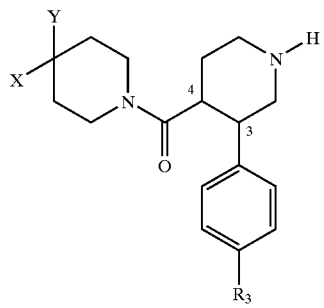

| Ex. # | Relative stereo. (3,4) | R³ | X | Y | Parent Ion m/z |
|---|---|---|---|---|---|
| 100 | trans (RS,RS) | —Cl | Me₃C-NH-C(O)-CH₂- | 4-iodophenyl | 608 |
| 101 | trans (R,R) | —F | Me₃C-NH-C(O)-CH₂- | 4-(CF₃)phenyl | 534 |
| 102 | trans (RS,RS) | —Cl | Me₃C-NH-C(O)-CH₂- | 4-(CF₃)phenyl | 550 |
| 103 | trans (R,R) | —F | Me₃C-NH-C(O)-CH₂- | 4-chlorophenyl | 500 |
| 104 | trans (RS,RS) | —Cl | Me₃C-NH-C(O)-CH₂- | 4-chlorophenyl | 516 |
| 105 | trans (R,R) | —F | Me₃C-NH-C(O)-CH₂- | 3,4-difluorophenyl | 502 |
| 106 | trans (RS,RS) | —Cl | Me₃C-NH-C(O)-CH₂- | 3,4-difluorophenyl | 518 |
| 107 | trans (R,R) | —F | Me₃C-NH-C(O)-CH₂- | 3-chlorophenyl | 500 |
| 108 | trans (RS,RS) | —F | Me₃C-C(O)-NH-Et | 2,4-dichlorophenyl | 548 |

-continued

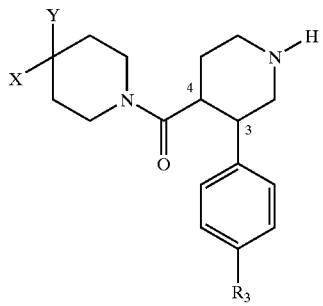

| Ex. # | Relative stereo. (3,4) | R³ | X | Y | Parent Ion m/z |
|---|---|---|---|---|---|
| 109 | trans (RS,RS) | —F | Me-C(Me)(Me)-C(=O)-NH- | 3-methoxyphenyl | 510 |

EXAMPLE 110

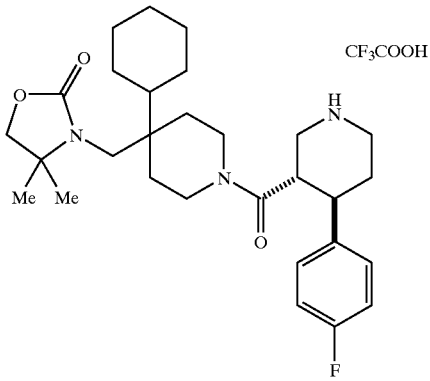

(3S,4R)-3-({4-Cyclohexyl-4-[(4,4-dimethyl-2-oxo-1,3-oxazolidin-3-yl)methyl]piperidin-1-yl}carbonyl)-4-(4-fluorophenyl)piperidinium trifluoroacetate Step A: Preparation of 3-(ethoxycarbonyl)-4-oxopiperidinium chloride A mixture of ethyl 1-benzyl-4-oxopiderine-3-carboxylate hydrochloride (25.0 g, 84.0 mmol) and 10% Pd/C (2.5 g Degussa Type E101) in ethanol/water (1:1; 300 mL) was hydrogenated at 50 psi for 4 h. The resulting mixture was filtered through celite® and the filtrate evaporated in vacuo to give the title compound as a brown solid (84 mmol).

Step B: Preparation of 1-tert-butyl 3-ethyl 4-oxopiperidine-1,3-dicarboxylate

Di-tert-butyldicarbonate (21.2 g, 97.0 mmol) was added in one portion to a stirred mixture of the crude product of step A (84.0 mmol), sodium bicarbonate (7.7 g, 92.0 mmol) and sodium chloride (14.7 g, 252 mmol) in water/chloroform (1:2; 300 mL) and the resulting mixture heated at 60° C. for 3 h. After cooling to room temperature, the organic phase was separated and the aqueous phase extracted three times with chloroform. The combined organic extracts were washed with brine, dried (MgSO₄) and concentrated in vacuo. The residue (33.8 g) was used without further purification in the subsequent reaction.

Step C: Preparation of 1-tert-butyl 3-ethyl 4-{[(trifluoromethyl)-sulfonyl]oxy}-5,6-dihydropyridine-1,3(2H)-dicarboxylate Trifluoromethanesulfonic anhydride (15.5 mL, 92.0 mmol) was added over approximately 0.1 h, via syringe, to a stirred solution of the product of step B (33.8 g, 84.0 mmol) and N,N-diisopropylethylamine (17.6 mL, 101.0 mmol) in methylene chloride (300 mL) at −78° C. After allowing to warm to ambient temperature overnight, the reaction mixture was quenched with saturated aqueous sodium bicarbonate, poured into water and extracted three times with methylene chloride. The combined organic extracts were washed with brine, dried (MgSO₄) and concentrated in vacuo. Purification of the residue by flash chromatography on silica gel (gradient elution; 0–20% ethyl acetate/hexanes as eluent) gave the title compound as an amber colored oil (23.0 g).

Step D: Preparation of 1-tert-butyl 3-ethyl 4-(4-fluorophenyl)-5,6-dihydropyridine-1,3(2H)-dicarboxylate A vigorously stirred suspension of the product of step C (1.00 g, 2.48 mmol), 4-fluorophenylboronic acid (0.382 g, 2.73 mmol) and [1,1'-bis(diphenylphosphino)-ferrocene] dichloropalladium(II) (0.102 g, 0.124 mmol) in toluene/ethanol (3:2; 24.0 mL) was degassed via three vacuum/nitrogen ingress cycles and then heated to approximately 80° C. Aqueous 2 M sodium carbonate (3.10 mL, 6.20 mmol) was added dropwise via syringe and the resulting mixture maintained at reflux overnight. After cooling to ambient temperature, the reaction mixture was diluted with ethyl acetate and filtered through celite®. The filtrate was poured into water and extracted three times with ethyl acetate. The combined organic extracts were washed with brine, dried (MgSO₄) and concentrated in vacuo. Purification of the residue by medium pressure liquid chromatography on silica gel (gradient elution; 0–15% ethyl acetate/hexanes as eluent) afforded the title compound as a colorless oil (0.762 g).

Step E: Preparation of 1-tert-butyl 3-ethyl 4-(4-fluorophenyl)piperidine-1,3-dicarboxylate Magnesium metal (0.525 g, 21.8 mmol) was added in three portions over approximately 0.3 h to a stirred solution of the product of step D (0.762 g, 2.18 mmol) in methanol at ambient temperature. After stirring overnight, the reaction mixture was poured into 1 N hydrochloric acid (100 mL) and extracted three times with ethyl acetate. The combined organic extracts were washed with saturated sodium bicarbonate, brine, dried (MgSO$_4$) and concentrated in vacuo. Purification of the residue by medium pressure liquid chromatography on silica gel (gradient elution; 0–25% ethyl acetate/hexanes as eluent) furnished the title compound (3:1 mixture of cis/trans diastereoisomers) as a colorless oil (0.651 g).

Step F: Preparation of (±)-trans-1-(tert-butoxycarbonyl)-4-(4-fluorophenyl)piperidine-3-carboxylic acid Excess sodium metal was added to a stirred solution of the product of step E (0.651 g, 1.85 mmol) in methanol (5.0 mL) at ambient temperature, and the resulting solution was heated to 75° C. After approximately 1 h, 5 M sodium hydroxide (3.0 mL) was added and the reaction mixture heated to 100° C. for an additional 1 h. After cooling to room temperature, the reaction mixture was acidified to pH 5 with 2 N hydrochloric acid and extracted three times with methylene chloride. The combined organic extracts were washed with brine, dried (MgSO$_4$) and concentrated in vacuo. The crude product was used without further purification in the subsequent reaction.

Step G: Preparation of (±)-trans-3-({4-cyclohexyl-4-[(4,4-dimethyl-2-oxo-1,3-oxazolidin-3-yl)methyl]piperidin-1-yl}carbonyl)-4-(4fluorophenyl)piperidinium trifluoroacetate 1-(3-Dimethylaminopropyl)-3-ethylcarbodiimide hydrochloride (0.0174 g, 0.091 mmol) was added to a stirred mixture of the crude product of step F (0.0294 g, 0.091 mmol), 4-cyclohexyl-4-[(4,4-dimethyl-2-oxo-1,3-oxazolidin-3-yl)methyl]piperidinium chloride (0.025 g, 0.076 mmol), 1-hydroxybenzotriazole (0.0123 g, 0.091 mmol) and N-methylmorpholine (0.010 mL, 0.091 mmol) in methylene chloride (0.500 mL) at ambient temperature. After approximately 18 h, the reaction mixture was poured into water/saturated sodium bicarbonate (1:1) and extracted three times with methylene chloride. The combined organic extracts were washed with brine, dried (Na$_2$SO$_4$) and concentrated in vacuo. A saturated solution of hydrogen chloride in ethyl acetate (1.0 mL) was added to a solution of the crude amide in methylene chloride (1.0 mL) at room temperature. After 18 h, the volatiles were evaporated in vacuo, and the crude residue purified by preparative reversed phase high pressure liquid chromatography on YMC Pack Pro C18 phase (gradient elution; 0–100% acetonitrile/water as eluent, 0.1% TFA as modifier) to give the title compound (0.031 g) as an off-white solid [MS: m/z 500 (MH$^+$)].

Following a procedure similar to that described above for Example 110, the following compounds can be prepared:

| Ex. # | Relative stereo. (3,4) | R$^1$ | R$^2$ | Parent Ion m/z |
|---|---|---|---|---|
| 111 | trans (RS,RS) | —H | 3-chlorophenyl | 516 |
| 112 | trans (RS,RS) | —H | 4-methoxyphenyl | 512 |
| 113 | trans (RS,RS) | —H | 4-chlorophenyl | 516 |
| 114 | trans (R,R) | methyl | 4-fluorophenyl | |
| 115 | trans (R,R) | methyl | 3-chlorophenyl | |
| 116 | trans (R,R) | methyl | 4-methoxyphenyl | |
| 117 | trans (R,R) | methyl | 4-chlorophenyl | |
| 118 | trans (R,R) | isopropyl | 4-fluorophenyl | |
| 119 | trans (R,R) | isopropyl | 4-chlorophenyl | |
| 120 | trans (R,R) | isopropyl | 2,4-difluorophenyl | |

EXAMPLE 121

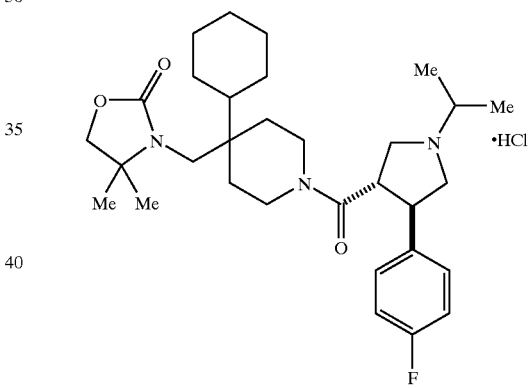

(3S, 4R)-3-({4-Cyclohexyl-4-[(4,4-dimethyl-2-oxo-1,3-oxazolidin-3-yl)methyl]piperidin-1-yl}carbonyl)-4-(4-fluorophenyl)-1-isopropylpyrrolidinium chloride

Step A: Preparation of (4S)-4-benzyl-3-[(2E)-3-(4-fluorophenyl)prop-2-enoyl]-1,3-oxazolidin-2-one A flame-dried 1 L 3-necked flask equipped with a mechanical stirrer was charged with (2E)-3-(4-fluorophenyl)prop-2-enoic acid (20.769 g; 0.125 mol) and tetrahydrofuran (275 mL). The reaction was cooled to −20° C. followed by the sequential addition of triethylamine (16.443 g; 0.163 mol) and trimethylacetyl chloride (16.580 g; 0.138 mol). After 30 min, the reaction was warmed to ambient temperature where it remained for an additional 90 min. A separate 2 L 3-necked flask, equipped with a mechanical stirrer, and a filter funnel, was charged with (S)-4-benzyloxazolidinone (20.20 g; 0.114 mol), anhydrous powdered lithium chloride (5.316 g; 0.125 mol), tetrahydrofuran (500 mL) and triethylamine (14.996 g; 0.148 mol) and cooled to −20° C. The mixed anhydride was rapidly added to the oxazolidinone solution through the filter funnel using a slight vacuum. After 30 min, the reaction was allowed to warm to ambient temperature for 5 h. The reaction was filtered through a fritted-funnel and concentrated in vacuo. The crude residue was diluted with ethyl acetate, washed with 1 N hydrochloric acid, saturated sodium bicarbonate, brine, dried ($MgSO_4$), filtered and concentrated in vacuo. The crude product was purified on a silica gel chromatography column eluted with methylene chloride. Evaporation of the purified fractions and drying in vacuo afforded 26.36 g of the title compound.

Step B: Preparation of (4S)-4-benzyl-3-{[(3R,4R)-1-benzyl-4-(4fluorophenyl)pyrrolidin-3-yl]carbonyl}-1,3-oxazolidin-2-one To a cooled (0° C.) solution of the product of step A (12.667 g; 38.9 mmol) in methylene chloride (110 mL) was added N-(methoxymethyl)-N-(trimethylsilylmethyl)benzylamine (13.866 g; 58.4 mmol) followed by a catalytic amount of trifluoroacetic acid (0.15 mL). After 10 min at 0° C., the reaction was allowed to warm to ambient temperature for 8 h. The reaction mixture was diluted with methylene chloride and washed with saturated saturated sodium bicarbonate, brine, dried ($MgSO_4$), filtered and concentrated in vacuo. The crude residue was purified on a silica gel chromatography column eluted with methylene chloride to afford 7.42 g of the less polar diastereoisomer and 7.79 g of the more polar diastereoisomer.

Step C: Preparation of tert-butyl (3R,4R)-3-{[(4S)-4-benzyl-2-oxo-1,3-oxazolidin-3-yl]carbonyl}-4-(4-fluorophenyl)pyrrolidine-1-carboxylate To a suspension of the product of step B (2.0 g; 4.4 mmol) in toluene (20 mL) was added 4 eq of 1-chloroethyl chloroformate (17.5 mmol; 1.33 mL). The reaction was heated to 100° C. for 6 h at which time starting material still remained. Thus, an additional 2 eq. of 1-chloroethyl chloroformate (8.8 mmol; 0.66 mL) was added and heating was resumed for another 20 h. The volatiles were removed in vacuo and the crude carbamate was dissolved in methanol (20 mL). The reaction mixture was heated to 70° C. for 2 h. The volatiles were removed in vacuo and the crude amine was dissolved in methylene chloride (400 mL) followed by washing the organic solution with saturated sodium bicarbonate and brine. The organic phase was dried ($Na_2SO_4$), filtered and concentrated in vacuo to provide the crude amine which was purified on silica gel using a gradient elution (50% ethyl acetate/hexane to elute the starting material followed by 9:1 methylene chloride/methanol (containing 10% v/v ammonium hydroxide). This provided 720 mg of the desired amine. The amine (720 mg; 1.96 mmol) was dissolved in methylene chloride (5 mL) and saturated sodium bicarbonate (5 mL) was added followed by di-tert-butyldicarbonate (533 mg; 2.45 mmol). After 1 h, the mixture was diluted with methylene chloride (100 mL) followed by washing the organic solution with saturated sodium bicarbonate and brine. The organic phase was dried ($Na_2SO_4$), filtered and concentrated in vacuo. The crude product was purified on silica gel (30% ethyl acetate/hexane) which furnished 840 mg of the title compound.

Step D: Preparation of (3R,4R)-1-(tert-butoxycarbonyl)-4-(4-fluorophenyl)pyrrolidine-3-carboxylic acid To a cooled (0° C.) solution of the product of step C (835 mg; 1.78 mmol) lithium hydroxide (85 mg; 3.56 mmol) in 15 mL of a 4:1 mixture of tetrahydrofuran-water with a 30% aqueous solution of hydrogen peroxide. After 5 min, the solution was warmed to ambient temperature and stirred for 5 h. The reaction mixture was poured into a 10% aqueous solution of sodium sulfite and then acidified to pH 3 with 1 N hydrochloric acid. The aqueous solution was extracted three times with ethyl acetate. The organic phase was washed with brine, dried ($MgSO_4$), filtered, concentrated in vacuo and the crude acid was purified on silica gel (30% ethyl acetate/hexane with 1% acetic acid) which furnished 520 mg of the title compound.

Step E: Preparation of (3R,4R)-3-({4-cyclohexyl-4-[(4,4-dimethyl-2-oxo-1,3oxazolidin-3-yl)methyl]piperidin-1-yl}carbonyl)-4-(4-fluorophenyl)pyrrolidinium chloride To a suspension of 4-cyclohexyl-4-[(4,4-dimethyl-2-oxo-1,3-oxazolidin-3-yl)methyl]piperidinium chloride (150 mg; 0.4532 mmol) in methylene chloride (4.0 mL) was added N-methylmorpholine (183 mg; 0.2 mL). After 20 min, the following reagents were added sequentially: 1-(3-dimethylaminopropyl)-3-ethylcarbodiimide hydrochloride (130 mg; 0.6798 mmol), 1-hydroxybenzotriazole (92 mg; 0.6798 mmol) and the product of step D (154 mg; 0.4985 mmol). The final reaction mixture was maintained at ambient temperature for 48 h. The reaction mixture was diluted with methylene chloride (100 mL) followed by washing the organic solution with saturated sodium bicarbonate and brine. The organic phase was dried ($Na_2SO_4$), filtered and concentrated in vacuo to provide the crude N-BOC protected pyrrolidine that was purified on silica gel (50% ethyl acetate/hexane as the elution solvent). The crude N-BOC protected pyrrolidine was then dissolved in ethyl acetate (2 mL) followed by the addition of a saturated solution of hydrogen chloride in ethyl acetate (2 mL). The reaction mixture was maintained at ambient temperature for 2 h at which time the volatiles were removed in vacuo. The crude product was triturated to high purity with diethyl ether which furnished 204 mg of the title compound as a hydrochloride salt.

Step F: Preparation of (3S,4R)-3-({4-cyclohexyl-4-[(4,4-dimethyl-2-oxo-1,3-oxazolidin-3-yl)methyl]piperidin-1-yl}carbonyl)-4-(4-fluorophenyl)-1-isopropylpyrrolidinium chloride A solution of the product of step E (100 mg; 0.1916 mmol) in methylene chloride (100 mL) was converted to the free-base by washing with saturated sodium bicarbonate. The organic phase was washed with brine, dried ($Na_2SO_4$), filtered and the volatiles were removed in vacuo. The residue was dissolved in methylene chloride (2 mL) and cooled to 0° C. Acetone (111 mg; 0.14 mmol) was added, followed by acetic acid (57 mg; 0.9579 mmol) and sodium triacetoxyborohydride (0.575 mmol). The reaction mixture was stirred and allowed to warm to room temperature over 36 h at which time the reaction was quenched with saturated sodium bicarbonate. After extracting three times with methylene chloride, the organic solution was washed with brine, dried ($Na_2SO_4$), filtered and concentrated in vacuo to provide the crude residue which was purified on silica gel (93:7 methylene chloride/methanol (contaiing 10% v/v ammonium hydroxide). The product was dissolved in ethyl acetate (2 mL) and converted to the hydrochloride salt by addition of a saturated solution of hydrogen chloride in ethyl acetate (2 mL). The reaction mixture was maintained at ambient temperature for 30 min at which time the volatiles were removed in vacuo. The solid was triturated to high purity with diethyl ether which furnished 95 mg of the title compound as the hydrochloride salt [MS: m/z 528 ($MH^+$)].

Following a procedure similar to that described above for Example 121 the following compounds were prepared:

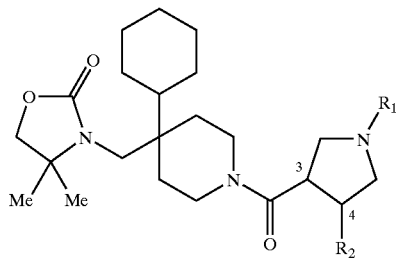

| Ex. # | Relative stereo. (3,4) | R¹ | R² | Parent Ion m/z |
|---|---|---|---|---|
| 122 | trans (SR,RS) | benzyl | 4-chlorophenyl | 592 |
| 123 | trans (SR,RS) | —H | 4-chlorophenyl | 502 |
| 124 | trans (R,S) | —H | 4-chlorophenyl | 502 |
| 125 | trans (R,S) | methyl | 4-chlorophenyl | 516 |
| 126 | trans (R,S) | isopropyl | 4-chlorophenyl | 544 |
| 127 | trans (S,R) | —H | 4-chlorophenyl | 502 |
| 128 | trans (S,R) | methyl | 4-chlorophenyl | 516 |
| 129 | trans (S,R) | isopropyl | 4-chlorophenyl | 544 |
| 130 | trans (SR,RS) | —H | 4-fluorophenyl | 486 |
| 131 | trans (SR,RS) | isopropyl | 4-fluorophenyl | 528 |
| 132 | trans (SR,RS) | ethyl | 4-fluorophenyl | 514 |
| 133 | trans (SR,RS) | —H | 3,4-dichlorophenyl | 536 |
| 134 | trans (SR,RS) | isopropyl | 3,4-dichlorophenyl | 578 |
| 135 | trans (S,R) | —H | 4-fluorophenyl | 486 |
| 136 | trans (S,R) | ethyl | 4-fluorophenyl | 514 |
| 137 | trans (S,R) | 2-pyrimidinyl | 4-fluorophenyl | 564 |
| 138 | trans (SR,RS) | —H | 3,4-difluorophenyl | 504 |
| 139 | trans (SR,RS) | isopropyl | 3,4-difluorophenyl | 546 |
| 140 | trans (SR,RS) | —H | 2,4-difluorophenyl | 504 |
| 141 | trans (SR,RS) | isopropyl | 2,4-difluorophenyl | 546 |
| 142 | trans (S,R) | —H | 2,4-difluorophenyl | 504 |
| 143 | trans (S,R) | isopropyl | 2,4-difluorophenyl | 546 |
| 144 | trans (S,R) | ethyl | 2,4-difluorophenyl | 532 |
| 145 | trans (S,R) | —CH₂C(CH₃)₃ | 2,4-difluorophenyl | 574 |
| 146 | trans (SR,RS) | —H | 3-chloro-4-fluorophenyl | 520 |
| 147 | trans (SR,RS) | isopropyl | 3-chloro-4-fluorophenyl | 562 |
| 148 | trans (SR,RS) | —H | 3,4-difluorophenyl | 503 |
| 149 | trans (SR,RS) | isopropyl | 3,4-difluorophenyl | 546 |
| 150 | trans (SR,RS) | —H | 2-thiophene | 474 |
| 151 | trans (SR,RS) | isopropyl | 2-thiophene | 516 |
| 152 | trans (SR,RS) | —H | 2-(3-chloro-thiophene) | 508 |
| 153 | trans (SR,RS) | isopropyl | 2-(3-chloro-thiophene) | 550 |

EXAMPLE 154

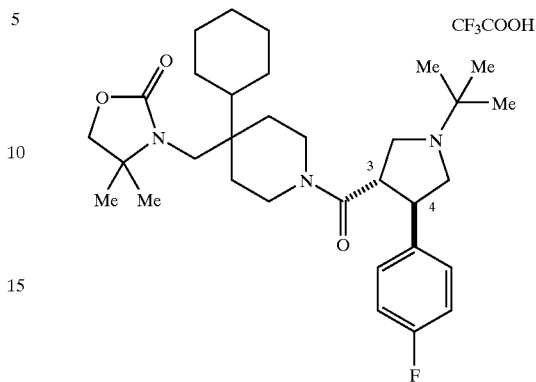

(±)-trans-1-Tert-butyl-3-({4-cyclohexyl-4-[(4,4-dimethyl-2-oxo-1,3-oxazolidin-3-yl)methyl]piperidin-1-yl}carbonyl)-4-(4-fluorophenyl)pyrrolidinium trifluoroacetate Step A: Preparation of N-tert-butyl-N-(trimethylsilylmethyl)amine A mixture of tert-butylamine (18.0 mL, 171 mmol) and (chloromethyl)trimethylsilane (7.00 g, 57.1 mmol) was heated in a thick-walled glass tube at 200° C. overnight. After cooling to ambient temperature, the reaction mixture was poured into 1 N sodium hydroxide and extracted three times with diethyl ether. The combined organic extracts were washed with brine, dried (MgSO₄), and the volatiles evaporated in vacuo. Distillation (atmospheric pressure; ~135° C.) of the residual liquid gave the title compound as a colorless liquid (7.67 g).

Step B: Preparation of N-tert-butyl-N-(methoxymethyl)-N-(trimethylsilylmethyl)amine N-tert-Butyl-N-(trimethylsilylmethyl)amine (8.47 g, 53.1 mmol) was added dropwise, over approximately 30 min, via a pressure equalizing addition funnel to a stirred solution of aqueous formaldehyde (5.98 mL of a 37 wt. % solution in water, 79.7 mmol) at 0° C. (ice cooling). After 45 min, methanol (6.45 mL, 159.3 mmol) was added and the resulting solution was saturated with potassium carbonate. After stirring vigorously for approximately 5 h, the aqueous phase was removed. The organic phase was saturated with potassium carbonate and stirred overnight. The reaction mixture was poured into water and extracted three times with diethyl ether. The combined organic extracts were washed with brine, dried (MgSO₄) and the volatiles evaporated in vacuo. Distillation (high vacuum; ~70° C.) of the residual liquid afforded the title compound as a colorless liquid (3.50 g).

Step C: Preparation of methyl (±)-trans-1-tert-butyl-4-(4-fluorophenyl)-pyrrolidine-3-carboxylate Trifluoroacetic acid (38.9 mL, 0.505 mmol) was added to a solution of the product of step B (1.03 g, 5.05 mmol) and methyl (2E)-3-(4-fluorophenyl)prop-2-enoate (1.00 g, 5.05 mmol) in methylene chloride (10 mL) at ambient temperature. After 18 h, the reaction mixture was poured into saturated aqueous sodium bicarbonate and extracted three times with methylene chloride. The combined organic extracts were washed with brine, dried (Na₂SO₄) and concentrated in vacuo. Purification of the crude residue by medium pressure liquid chromatography on silica gel (gradient elution; 0–9% methanol (containing 10% v/v ammonium hydroxide)/methylene chloride as eluent) furnished the title compound as a colorless liquid (1.06 g).

Step D: Preparation of (±)-trans-1-tert-butyl-3-carboxy-4-(4-fluorophenyl)pyrrolidinium chloride A solution of the product of Step C (50.0 mg, 0.179 mmol) in 8 N hydrochloric acid (1.0 mL) was heated at reflux overnight. After cooling to room temperature, the volatiles were evaporated and the residual solid used without further purification in the subsequent reaction.

Step E: Preparation of (±)-trans-1-tert-butyl-3-({4-cyclohexyl-4-[(4,4-dimethyl-2-oxo-1,3-oxazolidin-3-yl)methyl]piperidin-1-yl}carbonyl)-4-(4-fluorophenyl)pyrrolidinium trifluoroacetate 1-(3-Dimethylaminopropyl)-3-ethylcarbodiimide hydrochloride (51.5 mg, 0.269 mmol) was added to a stirred mixture of 4-cyclohexyl4-[(4,4-dimethyl-2-oxo-1,3-oxazolidin-3-yl)methyl]piperidinium chloride (54.9 mg, 0.166 mmol), crude product of step D (0.179 mmol), 1-hydroxybenzotriazole (36.3 mg, 0.269 mmol) and N-methylmorpholine (59.0 L, 0.537 mmol) in methylene chloride (1.8 mL) at ambient temperature. After approximately 18 h, the reaction mixture was poured into saturated aqueous sodium bicarbonate and extracted three times with methylene chloride. The combined organic extracts were washed with brine, dried (Na$_2$SO$_4$) and concentrated in vacuo. Purification of the residue by preparative reversed phase high pressure liquid chromatography on YMC Pack Pro C18 phase (gradient elution; 0–100% acetonitrile/water as eluent, 0.1% TFA as modifier) gave the title compound as an off-white solid [MS: m/z 542 (MH$^+$)].

Following a procedure similar to that described above for Example 154, the following compounds were prepared:

| Ex. # | Relative stereo. (3,4) | X | R$^2$ | Parent Ion m/z |
|---|---|---|---|---|
| 155 | trans (S,R) | 4,4-dimethyl-2-oxo-3-ethyl-1,3-oxazolidinylmethyl | 2,4-difluorophenyl | 560 |
| 156 | trans (R,S) | 4,4-dimethyl-2-oxo-3-ethyl-1,3-oxazolidinylmethyl | 2,4-difluorophenyl | 560 |
| 157 | trans (SR,RS) | 4,4-dimethyl-2-oxo-3-ethyl-1,3-oxazolidinylmethyl | 2,3,4-trifluorophenyl | 578 |
| 158 | trans (SR,RS) | 4,4-dimethyl-2-oxo-3-ethyl-1,3-oxazolidinylmethyl | 2-chloro-4-fluorophenyl | 576 |

-continued

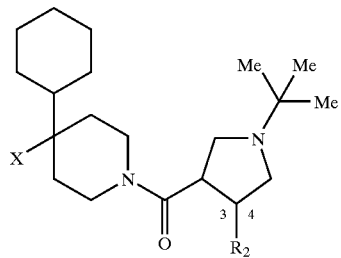

| Ex. # | Relative stereo. (3,4) | X | R² | Parent Ion m/z |
|---|---|---|---|---|
| 150 | trans (SR,RS) | 4,4-dimethyl-3-ethyl-oxazolidin-2-one | 2-iodo-4-fluoro-6-chlorophenyl | 686 |
| 160 | trans (SR,RS) | 4,4-dimethyl-3-ethyl-oxazolidin-2-one | 2,5-difluorophenyl | 574 |
| 161 | trans (SR,RS) | ethoxycarbonyl (Me-CH2-O-C(=O)-) | 2,4-difluorophenyl | 505 |
| 162 | trans (SR,RS) | ethoxycarbonyl | 4-fluorophenyl | 487 |
| 163 | trans (S,R) | 2-acetamido-2-methylpropyl | 2,4-difluorophenyl | 532 |
| 164 | trans (R,S) | 2-acetamido-2-methylpropyl | 2,4-difluorophenyl | 532 |
| 165 | trans (SR,RS) | 2-acetamido-2-methylpropyl | 2,4-difluorophenyl | 532 |
| 166 | trans (SR,RS) | 2-acetamido-2-methylpropyl | 4-fluorophenyl | 514 |
| 167 | trans (S,R) | 2-hydroxy-2-methylpentyl | 2,4-difluorophenyl | 519 |
| 168 | trans (R,S) | 2-hydroxy-2-methylpentyl | 2,4-difluorophenyl | 519 |

-continued

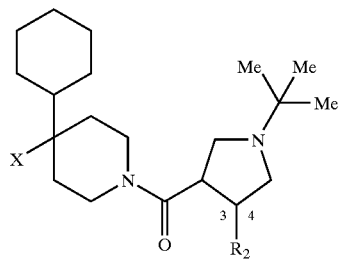

| Ex. # | Relative stereo. (3,4) | X | R² | Parent Ion m/z |
|---|---|---|---|---|
| 169 | trans (S,R) | Et₂N-C(O)-CH₂-CH₂- | 2,4-difluorophenyl | 546 |
| 170 | trans (S,R) | F₃C-CH₂-NH-C(O)-CH₂-CH₂- | 2,4-difluorophenyl | 572 |
| 171 | trans (S,R) | (iPr)(Et)N-C(O)-CH₂-CH₂- | 2,4-difluorophenyl | 560 |
| 172 | trans (S,R) | (1-Me-pyrazol-4-yl)CH₂-NH-C(O)-CH₂-CH₂- | 2,4-difluorophenyl | 584 |
| 173 | trans (S,R) | cyclopropyl(Me)N-C(O)-CH₂-CH₂- | 2,4-difluorophenyl | 544 |
| 174 | trans (S,R) | Et₂N-CH₂-CH₂-CH₂- | 2,4-difluorophenyl | 532 |
| 175 | trans (S,R) | (Et)(iPr)N-CH₂-CH₂-CH₂- | 2,4-difluorophenyl | 546 |
| 176 | trans (S,R) | (Et)(Me)N-C(O)-CH₂-CH₂- | 2,4-difluorophenyl | 532 |
| 177 | trans (S,R) | pyrrolidin-1-yl-CH₂-CH₂- | 2,4-difluorophenyl | 530 |

-continued

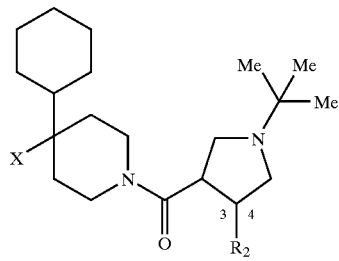

| Ex. # | Relative stereo. (3,4) | X | R² | Parent Ion m/z |
|---|---|---|---|---|
| 178 | trans (S,R) | morpholino-propyl | 2,4-difluorophenyl | 546 |
| 179 | trans (S,R) | t-BuNHC(O)CH₂CH₂- | 2,4-difluorophenyl | 516 |
| 180 | trans (S,R) | azetidinyl-propyl | 2,4-difluorophenyl | 516 |
| 181 | trans (S,R) | 2-oxa-5-azabicyclo acyl | 2,4-difluorophenyl | 572 |
| 182 | trans (S,R) | iPr-S-CH₂- | 2,4-difluorophenyl | 521 |
| 183 | trans (S,R) | iPr-S(O)-CH₂- | 2,4-difluorophenyl | 537 |
| 184 | trans (S,R) | iPr-SO₂-CH₂- | 2,4-difluorophenyl | 553 |
| 185 | trans (S,R) | Me-S-CH₂CH₂- | 2,4-difluorophenyl | 493 |
| 186 | trans (S,R) | Me-S(O)-CH₂CH₂- | 2,4-difluorophenyl | 509 |
| 187 | trans (S,R) | Me-SO₂-CH₂CH₂- | 2,4-difluorophenyl | 525 |

-continued

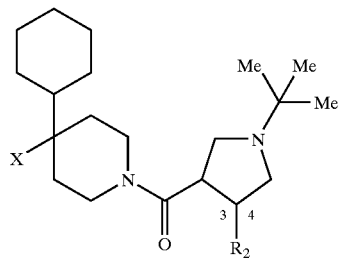

| Ex. # | Relative stereo. (3,4) | X | R² | Parent Ion m/z |
|---|---|---|---|---|
| 188 | trans (S,R) | Me-CH₂-S- | 2,4-difluorophenyl | 507 |
| 189 | trans (S,R) | Me-CH₂-S(O)- | 2,4-difluorophenyl | 523 |
| 190 | trans (S,R) | Me-CH₂-SO₂- | 2,4-difluorophenyl | 539 |
| 191 | trans (S,R) | Me-CH₂CH₂-S- | 2,4-difluorophenyl | 521 |
| 192 | trans (S,R) | Me-CH₂CH₂-S(O)- | 2,4-difluorophenyl | 537 |
| 193 | trans (S,R) | Me-CH₂CH₂-SO₂- | 2,4-difluorophenyl | 553 |
| 194 | trans (S,R) | cyclopropyl-CH₂-S(O)- | 2,4-difluorophenyl | 549 |
| 195 | trans (S,R) | cyclopropyl-CH₂-SO₂- | 2,4-difluorophenyl | 565 |
| 196 | trans (S,R) | cyclobutyl-SO₂- | 2,4-difluorophenyl | 565 |
| 197 | trans (S,R) | N-ethyl triazolyl | 2,4-difluorophenyl | 542 |
| 198 | trans (S,R) | 3,3-dimethyl-2-oxo-azetidinyl | 2,4-difluorophenyl | 544 |

-continued

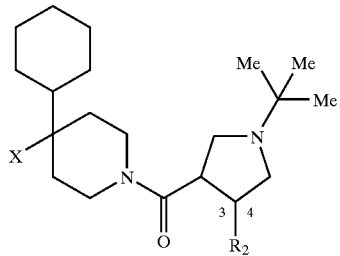

| Ex. # | Relative stereo. (3,4) | X | R² | Parent Ion m/z |
|---|---|---|---|---|
| 199 | trans (S,R) | (azetidinone-CH₂-) | 2,4-difluorophenyl | 516 |
| 200 | trans (S,R) | (pyrrolidinone-CH₂-) | 2,4-difluorophenyl | 530 |
| 201 | trans (S,R) | (3,3-dimethylpyrrolidinone-CH₂-) | 2,4-difluorophenyl | 558 |

EXAMPLE 202

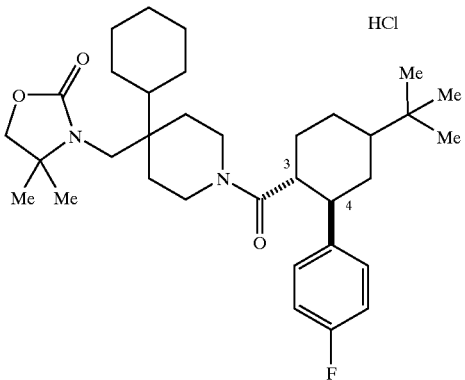

(±)-trans-1-Tert-butyl4-({4-cyclohexyl-4-[(4,4-dimethyl-2-oxo-1,3-oxazolidin-3-yl)methyl]piperidin-1-yl}carbonyl)-3-(2,4-difluorophenyl)piperidinium chloride Step A: Preparation of ethyl 4-(ten-butylamino)butanoate Ethyl 4-bromobutyrate (20 g; 102.6 mmol) was combined with tert-butylamine (37.2 g; 0.514 mol) and heated to 100° C. in a sealed tube for 24 h. The contents of the reaction were cooled to ambient temperature, the volatiles were removed in vacuo and the crude product was dissolved in 1 N hydrochloric acid. The aqueous layer was extracted twice with diethyl ether and the organic layer discarded. The aqueous layer was adjusted to pH 9 with 2.5 N sodium hydroxide. The aqueous layer was extracted three times with diethyl ether. The combined organic extracts (from the pH 9 aqueous layer) were washed with brine, dried ($Na_2SO_4$), filtered and the solvent was removed in vacuo to afford the title compound (14.2 g).

Step B: Preparation of ethyl N-(tert-butyl)-N-(2-ethoxy-2-oxoethyl)4-aminobutanoate To a solution of the product of step A (14.2 g; 75.5 mmol) in toluene (150 mL) was added potassium carbonate (20.8 g; 151.1 mmol) and ethyl bromoacetate (18.9 g; 113.3 mmol). The reaction was heated to 120° C. for 24 h. The reaction mixture was cooled to ambient temperature and partitioned between 1 N hydrochloric acid and diethyl ether. The aqueous layer was extracted twice with diethyl ether and the organic layer discarded. The aqueous layer was adjusted to pH 9 with 2.5 N sodium hydroxide and extracted three times with diethyl ether. The combined organic extracts (from the pH 9 aqueous layer) were washed with brine, dried ($Na_2SO_4$), filtered and concentrated in vacuo to furnish the title compound (19.2 g).

Step C: Preparation of ethyl 1-tert-butyl-3-oxopiperidine-4-carboxylate

To a solution of the product of step B (14.0 g; 50.9 mmol) in tetrahydrofuran (200 mL) was added 1.05 eq of potassium tert-butoxide (6.0 g; 53.5 mmol). The reaction was maintained at ambient temperature for 2 h and then quenched with a sufficient amount of saturated aqueous ammonium chloride to make the solution pH 8. The tetrahydrofuran was removed in vacuo and the aqueous layer was extracted three times with diethyl ether. The combined organic extracts were washed with brine, dried ($Na_2SO_4$), filtered and concentrated in vacuo to afford the title compound (7.15 g).

Step D: Preparation of ethyl 1-tert-butyl-5-{[(trifluoromethyl)sulfonyl]-oxy}-1,2,3,6-tetrahydropyridine-4-carboxylate To a cooled (−78° C.) solution of the product of step C (7.15 g; 31.2 mmol) in methylene chloride (100 mL) was added diisopropylethylamine (5.04 g; 39.0 mmol). Triflic anhydride (9.69 g; 34.3 mmol) was then added dropwise over 10 min and the reaction mixture was allowed to warm to ambient temperature over 16 h. The mixture was concentrated to about 50% of the initial volume and directly loaded onto silica gel eluted with 50% ethyl acetate/hexane. Evaporation of the purified fractions provided 5.05 g of the title compound.

Step E: Preparation of ethyl 1-tert-butyl-5-(2,4-difluorophenyl)-1,2,3,6-tetrahydropyridine-4-carboxylate The product of step D (5.05 g; 14.4 mmol), 2,4-difluorophenylboronic acid (2.85 g; 18.0 mmol) and [1,1'-bis(diphenylphosphino)ferrocene)dichloropalladium(II) (0.589 g; 0.7 mmol) were combined and dissolved a 2:1 mixture of toluene:ethanol (54 mL). The reaction was heated to 80° C. followed by the dropwise addition of 2 M aqueous sodium carbonate over 10 min. The reaction was maintained at 80° C. for 2 h. The reaction was quenched with saturated aqueous sodium bicarbonate and the aqueous layer was extracted three times with ethyl acetate. The combined organic extracts were washed with brine, dried ($Na_2SO_4$), filtered concentrated in vacuo. The crude residue was purified on silica gel using a gradient elution (30%→40%→60% ethyl acetate/hexane) which furnished the title compound (2.8 g).

Step F: Preparation of methyl (±)-trans-1-tert-butyl-3-(2,4-difluorophenyl)piperidine-4-carboxylate The product of step E (1 g; 3.1 mmol) was dissolved in ethanol (20 mL) and treated with acetic acid (280 mg; 4.6 mmol) and 20% palladium hydroxide on carbon catalyst (0.760 g). The reaction mixture was stirred for 24 h under 1 atmosphere of hydrogen gas. The reaction was filtered through celite® and the filter cake was rinsed with copious amounts of methanol. The solvents were evaporated and the crude residue was dissolved in methylene chloride. The organic solution was washed with saturated sodium bicarbonate, brine, dried ($Na_2SO_4$), filtered and concentrated in vacuo. The crude residue was purified on silica gel using 10% methanol/methylene chloride to provide predominantly the cis-disubstituted piperidine. The cis isomer, accumulated from several experiments as described above, (5.5 g; 17.0 mmol) was dissolved in methanol (75 mL) followed by the addition of freshly cut sodium metal (1.27 g; 55.3 mmol). The reaction mixture was heated to 70° C. for 12 h. The reaction was quenched with saturated aqueous ammonium chloride and the aqueous layer was extracted with ethyl acetate. The combined organic extracts were dried ($Na_2SO_4$), filtered and concentrated in vacuo. The crude residue was purified on silica gel (50% ethyl acetate/hexane) which furnished the title compound.

Step G: Preparation of (±)-trans-1-tert-butyl-4-carboxy-3-(2,4-difluorophenyl)piperidinium chloride The product of step F (160 mg; 0.515 mmol) was heated to 100° C. in concentrated hydrochloric acid for 16 h. The volatiles were removed in vacuo and the crude residue was suspended in toluene and evaporated to dryness. This process was repeated three times to provide 170 mg of the title compound.

Step H: Preparation of (±)-trans-1-tert-butyl-4-({4-cyclohexyl-4-[(4,4-dimethyl-2-oxo-1,3-oxazolidin-3-yl)methyl]piperidin-1-yl}carbonyl)-3-(2,4-difluorophenyl)piperidinium chloride To a suspension of 4-cyclohexyl-4-[(4,4-dimethyl-2-oxo-1,3-oxazolidin-3-yl)methyl]piperidinium chloride (45 mg; 0.136 mmol) in methylene chloride (2.0 mL) was added N-methylmorpholine (35 mg; 0.036 mL). A separate flask was charged with the product of step G (50 mg; 0.1497 mmol), methylene chloride (2.0 mL), and N-methylmorpholine (35 mg; 0.036 mL) was added. After 20 min, the following reagents were added sequentially to the flask containing the product of step G: 1-(3-dimethylaminopropyl)-3-ethylcarbodiimide hydrochloride (39 mg; 0.204 mmol), 1-hydroxybenzotriazole (28 mg; 0.204 mmol) followed by the dropwise addition of the piperidine solution from the first flask. The final reaction mixture was maintained at ambient temperature for 48 h. The reaction was diluted with methylene chloride (100 mL) then washed with saturated sodium bicarbonate and brine. The mixture was dried ($Na_2SO_4$), filtered and concentrated in vacuo to provide a crude product that was purified on silica gel (eluted first with 75% ethyl acetate/hexane followed by 95:5 methylene chloride/methanol (containing10% v/v ammonium hydroxide)). The purified product was dissolved in ethyl acetate (2 mL) and converted to the hydrochloride salt by treatment with a saturated solution of hydroogen chloride in ethyl acetate (2 mL). The reaction mixture was maintained at ambient temperature for 1 h at which time the volatiles were removed in vacuo. The crude hydrochloride salt was triturated to high purity with diethyl ether which furnished 50 mg of the title compound [MS: m/z 574 (MH$^+$)].

Following a procedure similar to that described above for Example 202, the following compounds can be prepared:

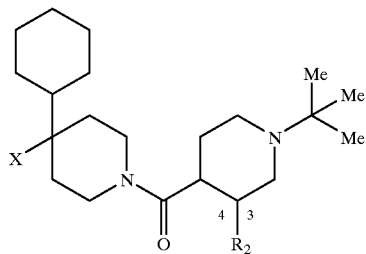

| Ex. # | Relative stereo. (3,4) | X | R² | Parent Ion m/z |
|---|---|---|---|---|
| 203 | trans (S,S) | 4,4-dimethyl-3-ethyl-oxazolidin-2-one | 2,4-difluorophenyl | 575 |
| 204 | trans (R,R) | 4,4-dimethyl-3-ethyl-oxazolidin-2-one | 2,4-difluorophenyl | 575 |
| 205 | trans (S,S) | HOC(Me)₂CH₂CH₃ | 2,4-difluorophenyl | |
| 206 | trans (R,R) | HOC(Me)₂CH₂CH₃ | 2,4-difluorophenyl | |
| 207 | trans (S,S) | Me₃C-NH-C(O)- | 2-fluorophenyl | |
| 208 | trans (S,S) | HOC(Me)₂CH₂CH₃ | 2-fluorophenyl | |
| 209 | trans (S,S) | Me₃C-NH-C(O)- | 2,4-difluorophenyl | 547 |
| 210 | trans (R,R) | Me₃C-NH-C(O)- | 2,4-difluorophenyl | 547 |
| 211 | trans (R,R) | Me₃C-NH-C(O)- | 2-fluorophenyl | |
| 212 | trans (R,R) | HOC(Me)₂CH₂CH₃ | 2-fluorophenyl | |

-continued

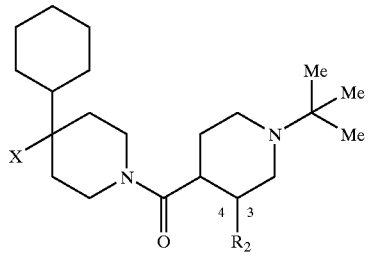

| Ex. # | Relative stereo. (3,4) | X | R² | Parent Ion m/z |
|---|---|---|---|---|
| 213 | trans (R,R) | HO-C(Me)₂-CH₂-NH-C(O)-CH₃ | 2,4-difluorophenyl | 563 |

EXAMPLE 214

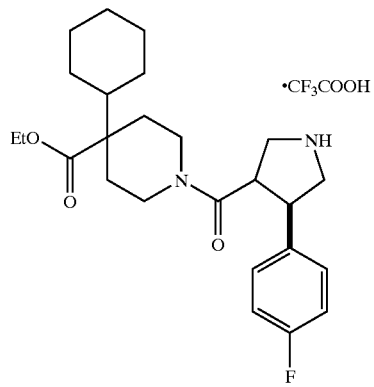

(±)-3-{[4-Cyclohexyl-4-(ethoxycarbonyl)piperidin-1-yl]carbonyl}-2-phenylpyrrolidinium trifluoroacetate Step A: Preparation of ethyl (±)-1-{[1-(tert-butoxycarbonyl)-2-phenylpyrrolidin-3-yl]carbonyl}-4-cyclohexylpiperidine-4-carboxylate 1-(3-Dimethylaminopropyl)-3-ethylcarbodiimide hydrochloride (1.09 mL of a 0.25 M solution in methylene chloride, 0.272 mmol) was added to a stirred mixture of 4-cyclohexyl-4-(ethoxycarbonyl)piperidinium chloride (50.0 mg, 0.181 mmol), (±)-1-(tert-butoxycarbonyl)-2-phenylpyrrolidine-3-carboxylic acid (68.6 mg, 0.235 mmol), 1-hydroxybenzotriazole (36.7 mg, 0.272 mmol) and N-methylmorpholine (59.7 µL, 0.543 mmol) in methylene chloride (0.7 mL) at ambient temperature. After approximately 18 h, the reaction mixture was poured into saturated aqueous sodium bicarbonate and extracted three times with methylene chloride. The combined organic extracts were washed with brine, dried (Na₂SO₄) and concentrated in vacuo. The crude residue was used without further purification in the subsequent reaction.

Step B: Preparation of (±)-3-{[4-cyclohexyl-4-(ethoxycarbonyl)piperidin-1-yl]carbonyl}-2-phenylprrolidinium chloride A saturated solution of hydrogen chloride in ethyl acetate (2.0 mL) was added to a solution of the crude product of step A in methylene chloride (1.0 mL) at room temperature. After 18 h, the volatiles were evaporated in vacuo, and the crude residue purified by preparative reversed phase high pressure liquid chromatography on YMC Pack Pro C18 phase (gradient elution; 0–100% acetonitrile/water as eluent, 0.1% TFA as modifier) to give the title compound (59.1 mg) as an off-white solid [MS: m/z 413 (MH⁺)].

Following a procedure similar to that described above for Example 214, the following compounds were prepared:

| Ex. # | X | R | Parent Ion m/z |
|---|---|---|---|
| 215 | Me-CH₂-O-C(O)- | 3-Ph-pyrrolidin-4-yl (racemic) | 413 |
| 216 | Me-CH₂-O-C(O)- | 4-Ph-piperidin-3-yl (racemic) | 427 |

-continued

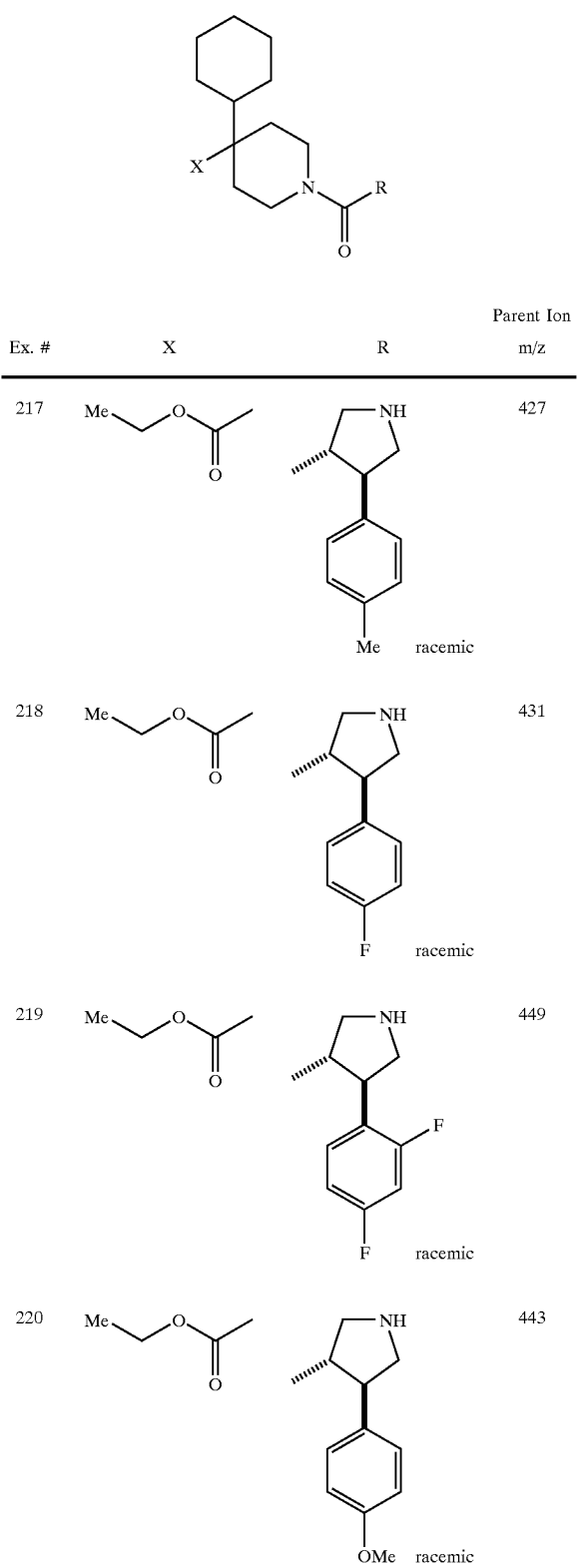

| Ex. # | X | R | Parent Ion m/z |
|---|---|---|---|
| 217 | Me-ethyl acetate | 3-methyl-4-(4-methylphenyl)pyrrolidine, racemic | 427 |
| 218 | Me-ethyl acetate | 3-methyl-4-(4-fluorophenyl)pyrrolidine, racemic | 431 |
| 219 | Me-ethyl acetate | 3-methyl-4-(2,4-difluorophenyl)pyrrolidine, racemic | 449 |
| 220 | Me-ethyl acetate | 3-methyl-4-(4-methoxyphenyl)pyrrolidine, racemic | 443 |

-continued

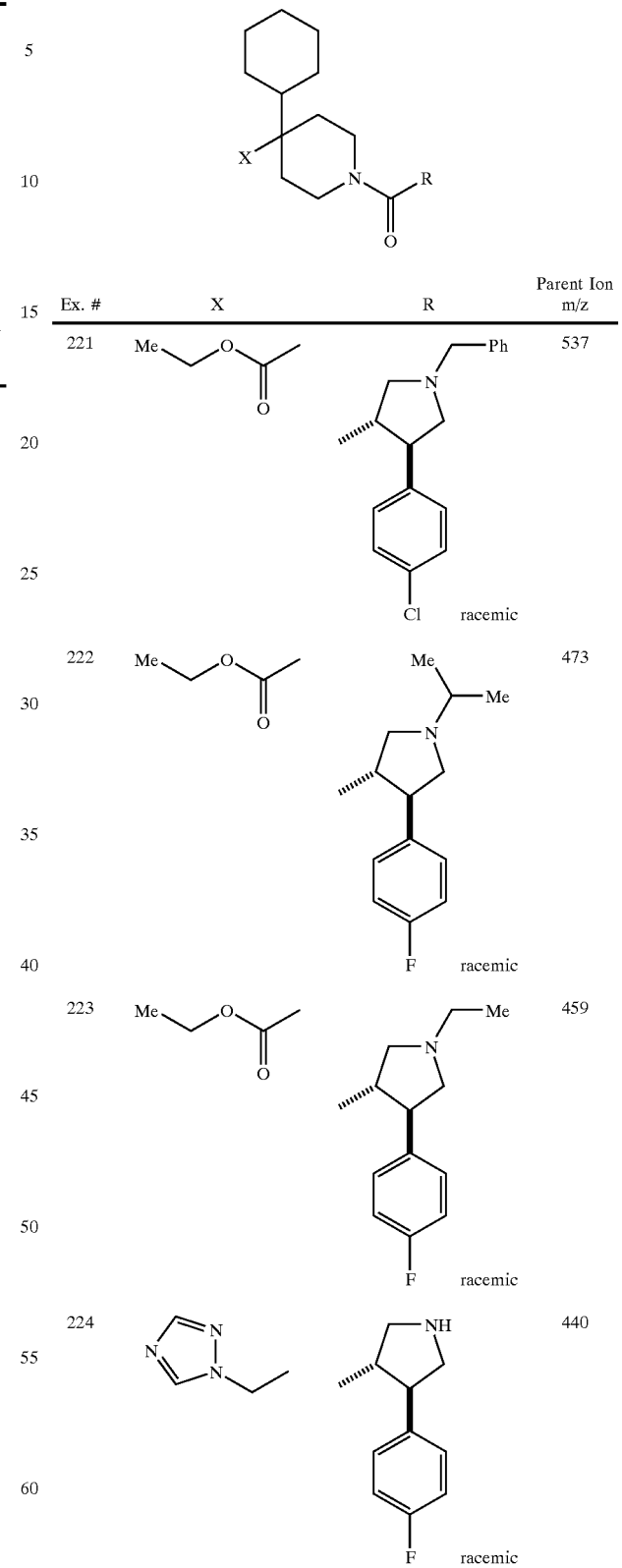

| Ex. # | X | R | Parent Ion m/z |
|---|---|---|---|
| 221 | Me-ethyl acetate | N-benzyl-3-methyl-4-(4-chlorophenyl)pyrrolidine, racemic | 537 |
| 222 | Me-ethyl acetate | N-isopropyl-3-methyl-4-(4-fluorophenyl)pyrrolidine, racemic | 473 |
| 223 | Me-ethyl acetate | N-ethyl-3-methyl-4-(4-fluorophenyl)pyrrolidine, racemic | 459 |
| 224 | 1-ethyl-1,2,4-triazole | 3-methyl-4-(4-fluorophenyl)pyrrolidine, racemic | 440 |

-continued

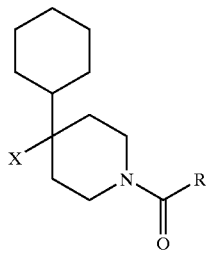

| Ex. # | X | R | Parent Ion m/z |
|---|---|---|---|
| 225 | ![triazole-ethyl] | Me-CH(Me)-N-pyrrolidine-(4-F-phenyl) racemic | 482 |
| 226 | HO-CH2-C(Me)2-NH-C(O)- | NH-pyrrolidine-(4-F-phenyl) | 474 |

Biological Assays

A. Binding Assay. The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRl); 100 ml 10% heat-inactivated fetal bovine serum (Sigma); 10 mL 10,000 unit/mL penicillin & 10,000 μg/mL streptomycin (Gibco/BRl); 10 ml 200 mM L-glutamine (Gibco/BRl); 1 mg/mL geneticin (G418) (Gibco/BRl). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mls/monolayer membrane preparation buffer having the composition: 10 mM Tris pH 7.2–7.4; 4 μg/mL Leupeptin (Sigma); 10 μM Phosphoramidon (Boehringer Mannheim); 40 μg/mL Bacitracin (Sigma); 5 μg/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500–1000 μL/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM $CaCl_2$; 1 mM $MgCl_2$; 5 mM KCl; 0.2% BSA; 4 μg/mL Leupeptin (SIGMA); 10 μM Phosphoramidon (Boehringer Mannheim); 40 μg/mL Bacitracin (SIGMA); 5 μg/mL Aprotinin (SIGMA); and 10 mM Pefabloc (Boehringer Mannheim). One hundred μL of membrane binding buffer containing 10–40 μg membrane protein was added, followed by 100 μM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 μL of Packard Microscint-20 was added to each well. The top was sealed and the radioactivity quantitated in a Packard Topcount Microplate Scintillation counter.

B. Functional Assay

Functional cell based assays were developed to discriminate melanocortin receptor agonists from antagonists.

Cells (for example, CHO— or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 Mar; 11(3): 274–80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5\times10^6$/mL. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an EC50 dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

C. In Vivo Food Intake Models

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276–R1285, 1991; McKenna K E et al, *Modulation By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

Representative compounds of the present invention were tested and found to bind to the melanocortin-4 receptor. These compounds were generally found to have $IC_{50}$ values less than 2 $\mu$M. Representative compounds of the present invention were also tested in the functional assay and found generally to activate the melanocortin-4 receptor with $EC_{50}$ values less than 1 $\mu$M.

Examples of a Pharmaceutical Composition

As a specific embodiment of an oral composition of a composition of the present invention, 5 mg of Example 169 is formulated with sufficient finely divided lactose to provide a total amount of 580 to 590 mg to fill a size O hard gelatin capsule.

As another specific embodiment of an oral composition of a compound of the present invention, 10 mg of Example 174 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

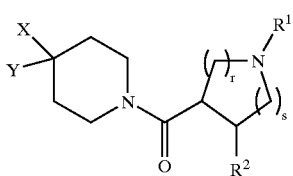

or a pharmaceutically acceptable salt thereof;
wherein
r is 1 or 2;
s is 1;
n is 0, 1 or 2;
p is 0, 1, or 2;
$R^1$ is selected from the group consisting of
hydrogen,
amidino,
$C_{1-4}$ alkyliminoyl,
$C_{1-10}$ alkyl,
$(CH_2)_n$-$C_{3-7}$ cycloalkyl,
$(CH_2)_n$-phenyl,
$(CH_2)_n$-naphthyl, and
$(CH_2)_n$-heteroaryl wherein heteroaryl is selected from the group consisting of
(1) pyridinyl,
(2) furyl,
(3) thienyl,
(4) pyrrolyl,
(5) oxazolyl,
(6) thiazolyl,
(7) imidazolyl,
(8) pyrazolyl,
(9) isoxazolyl,
(10) isothiazolyl,
(11) pyrimidinyl,
(12) pyrazinyl,
(13) pyridazinyl,
(14) quinolyl,
(15) isoquinolyl,
(16) benzimidazolyl,
(17) benzofuryl,
(18) benzothienyl,
(19) indolyl,
(20) benzthiazolyl, and
(21) benzoxazolyl;
in which phenyl, naphthyl, and heteroaryl are unsubstituted or substituted with one to three groups independently selected from $R^3$; and alkyl and cycloalkyl are unsubstituted or substituted with one to three groups independently selected from $R^3$ and oxo;
$R^2$ is selected from the group consisting of
phenyl,
naphthyl, and
heteroaryl wherein heteroaryl is selected from the group consisting of
(1) pyridinyl,
(2) furyl,
(3) thienyl,
(4) pyrrolyl,
(5) oxazolyl,
(6) thiazolyl,
(7) imidazolyl,
(8) pyrazolyl,
(9) isoxazolyl,
(10) isothiazolyl,
(11) pyrimidinyl,
(12) pyrazinyl,
(13) pyridazinyl,
(14) quinolyl,
(15) isoquinolyl,
(16) benzimidazolyl,
(17) benzofuryl,
(18) benzothienyl,
(19) indolyl,
(20) benzthiazolyl, and
(21) benzoxazolyl;
in which phenyl, naphthyl, and heteroaryl are unsubstituted or substituted with one to three groups independently selected from $R^3$;
$R^3$ is selected from the group consisting of
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_n C_{3-7}$ cycloalkyl,
halogen,
$OR^4$,
$(CH_2)_n N(R^4)_2$,
$(CH_2)_n C\equiv N$,
$CO_2R^4$,
$C(R^4)(R^4)N(R^4)_2$,
$NO_2$,
$(CH_2)_n NR^4SO_2R^4$
$(CH_2)_n SO_2N(R^4)_2$,
$(CH_2)_n S(O)_p R^4$,
$(CH_2)_n NR^4C(O)N(R^4)_2$,
$(CH_2)_n C(O)N(R^4)_2$,
$(CH_2)_n NR^4C(O)R^4$,
$(CH_2)_n NR^4CO_2R^4$,
$CF_3$,
$CH_2CF_3$,
$OCF_3$, and
$OCH_2CF_3$;
in which heteroaryl is as defined above; phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and $(CH_2)_n$ is unsubstituted or substituted with one to two groups independently selected from halogen, hydroxy, and $C_{1-4}$ alkyl;

each $R^4$ is independently selected from the group consisting of
hydrogen,
$C_{1-6}$ alkyl,
$(CH_2)_n$-phenyl,
$(CH_2)_n$-naphthyl, and
$(CH_2)_n C_{3-7}$ cycloalkyl;
wherein cycloalkyl is unsubstituted or substituted with one to three groups independently selected from halogen, $C_{1-4}$ alkyl, and $C_{1-4}$ alkoxy;
or two $R^4$ groups together with the atom to which they are attached form a 4- to 8-membered mono- or bicyclic ring system optionally containing an additional heteroatom selected from O, S, and $NC_{1-4}$ alkyl;

each $R^5$ is independently selected from the group consisting of
hydrogen,
$C_{1-8}$ alkyl,
$(CH_2)_n$-phenyl,
$(CH_2)_n$-naphthyl,
$(CH_2)_n$-heteroaryl, and
$(CH_2)_n C_{3-7}$ cycloalkyl;
wherein heteroaryl is as defined above; phenyl, naphthyl, and heteroaryl are unsubstituted or substituted with one to three groups independently selected from $R^3$; and alkyl, cycloalkyl, and $(CH_2)_n$ are unsubstituted or substituted with one to three groups independently selected from $R^3$ and oxo;
or two $R^5$ groups together with the atom to which they are attached form a 5- to 8-membered mono- or bicyclic ring system optionally containing an additional heteroatom selected from O, S, and $NC_{1-4}$ alkyl;

X is
$C_{1-8}$ alkyl, unsubstituted or substituted with one to three groups independently selected from $OR^4$;
$(CH_2)_n CON(R^5 R^5)$,
$(CH_2)_n CO_2 R^5$, and
$(CH_2)_n N(R^5)(R^5)$,
wherein alkyl, and $(CH_2)_n$, are unsubstituted or substituted with one to three groups independently selected from $R^3$ and oxo; and Y is cyclohexyl,
wherein cyclohexyl is optionally substituted with one to three groups independently selected from $R^3$ and oxo.

2. The compound of claim 1 wherein $R^1$ is selected from the group consisting of hydrogen, $C_{1-6}$ alkyl, $(CH_2)_{0-1}C_{3-6}$ cycloalkyl, and $(CH_2)_{0-1}$-phenyl; wherein phenyl is unsubstituted or substituted with one to three groups independently selected from $R^3$; and alkyl and cycloalkyl are optionally substituted with one to three groups independently selected from $R^3$ and oxo.

3. The compound of claim 1 wherein $R^2$ is phenyl or thienyl optionally substituted with one to three groups independently selected from $R^3$.

4. The compound of claim 3 wherein $R^2$ is phenyl optionally substituted with one to three groups independently selected from $R^3$.

5. The compound of claim 1 wherein X is selected from the group consisting of
$C_{1-6}$ alkyl, unsubstituted or substituted with one to three groups independently selected from $OR^4$;
$(CH_2)_{0-1}CO_2R^5$, and
$(CH_2)_{0-1}C(O)N(R^5)(R^5)$;

wherein alkyl is optionally substituted with one to three groups independently selected from $R^3$ and oxo.

6. The compound of claim 1 of structural formula IIa or IIb of the indicated trans relative stereochemical configuration:

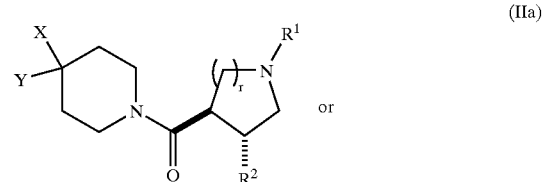

(IIa)

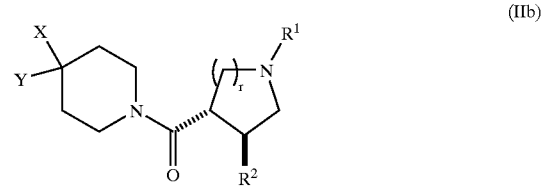

(IIb)

or a pharmaceutically acceptable salt thereof;
wherein
r is 1 or 2;
n is 0, 1, or 2;
p is 0, 1, or 2;
$R^1$ is hydrogen, amidino, $C_{1-4}$ alkyliminoyl, $C_{1-6}$ alkyl, $C_{3-6}$ cycloalkyl, $(CH_2)_{0-1}$ phenyl, or $(CH_2)_{0-1}$ heteroaryl; wherein phenyl and heteroaryl are unsubstituted or substituted with one to three groups independently selected from $R^3$; and alkyl and cycloalkyl are unsubstituted or substituted with one to three groups independently selected from $R^3$ and oxo;
$R^2$ is phenyl or thienyl optionally substituted with one to three groups independently selected from $R^3$;
$R^3$ is selected from the group consisting of
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_n C_{3-7}$ cycloalkyl,
halogen,
$OR^4$,
$(CH_2)_n N(R^4)_2$,
$(CH_2)_n C\equiv N$,
$CO_2 R^4$,
$C(R^4)(R^4)N(R^4)_2$,
$NO_2$,
$(CH_2)_n NR^4 SO_2 R^4$
$(CH_2)_n SO_2 N(R^4)_2$,
$(CH_2)_n S(O)_p R^4$,
$(CH_2)_n NR^4 C(O)N(R^4)_2$,
$(CH_2)_n C(O)N(R^4)_2$,
$(CH_2)_n NR^4 C(O)R^4$,
$(CH_2)_n NR^4 CO_2 R^4$,
$CF_3$,
$CH_2 CF_3$,
$OCF_3$, and
$OCH_2 CF_3$;
in which phenyl, naphthyl, heteroaryl, cycloalkyl, and heterocyclyl are unsubstituted or substituted with one to two substituents independently selected from halogen, hydroxy, $C_{1-4}$ alkyl, trifluoromethyl, and $C_{1-4}$ alkoxy; and $(CH_2)_n$ is unsubstituted or substituted with one to two groups independently selected from halogen, hydroxy, and $C_{1-4}$ alkyl;

each $R^4$ is independently selected from the group consisting of hydrogen, $C_{1-8}$ alkyl, and $C_{3-6}$ cycloalkyl;

wherein cycloalkyl is unsubstituted or substituted with one to three groups independently selected from halogen, $C_{1-4}$ alkyl, and $C_{1-4}$ alkoxy;

or two $R^4$ groups together with the atom to which they are attached form a 4- to 8-membered mono- or bicyclic ring system optionally containing an additional heteroatom selected from O, S, and $NC_{1-4}$ alkyl;

Y is cyclohexyl, wherein cyclohexyl is unsubstituted or substituted with one to three groups independently selected from $R^3$ and oxo; and X is selected from the group consisting of

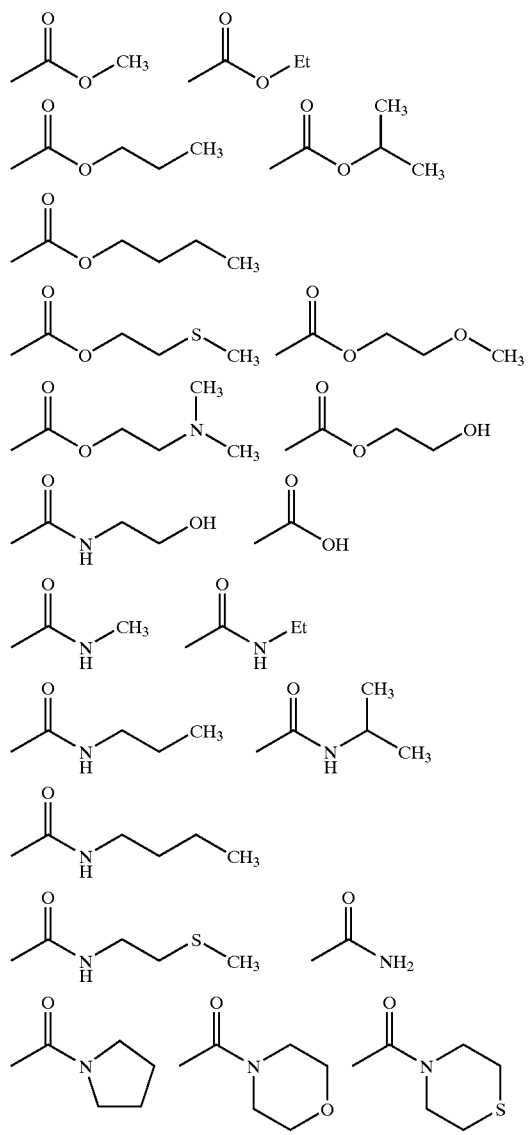

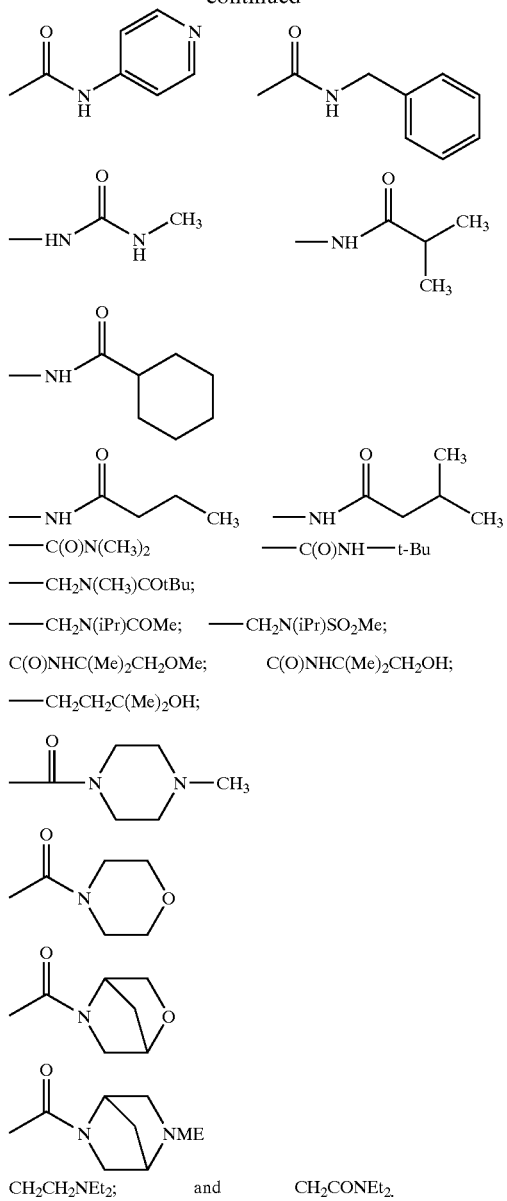

—C(O)N(CH₃)₂
—C(O)NH—t-Bu
—CH₂N(CH₃)COtBu;
—CH₂N(iPr)COMe;    —CH₂N(iPr)SO₂Me;
C(O)NHC(Me)₂CH₂OMe;    C(O)NHC(Me)₂CH₂OH;
—CH₂CH₂C(Me)₂OH;

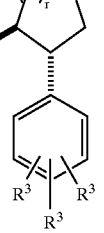

CH₂CH₂NEt₂;    and    CH₂CONEt₂.

7. The compound of claim 1 of structural formula IIIa or IIIb of the indicated trans relative stereochemical configuration:

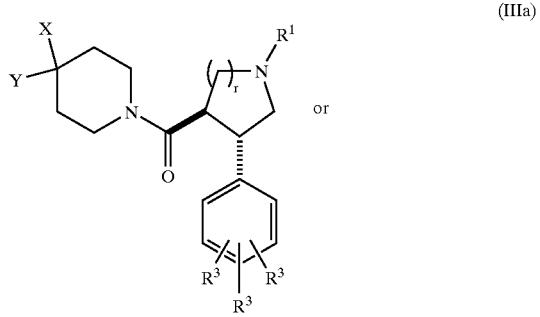

-continued

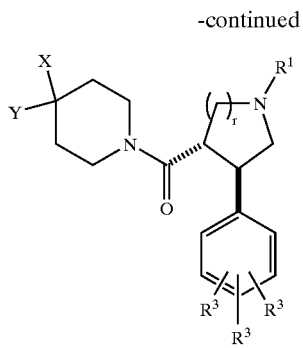
(IIIb)

or a pharmaceutically acceptable salt thereof;
wherein
  r is 1 or 2;
  $R^1$ is hydrogen, $C_{1-4}$ alkyl, or $(CH_2)_{0-1}$ phenyl;
  each $R^3$ is independently selected from the group consisting of hydrogen, halo, $C_{1-4}$ alkyl, trifluoromethyl, and $C_{1-4}$ alkoxy;
  Y is cyclohexyl; and
  X is selected from the group consisting of $CH_2CH_2NEt_2$; $CH_2CONEt_2$; 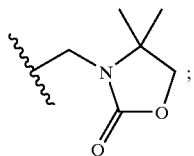

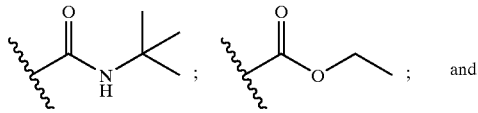 ; and

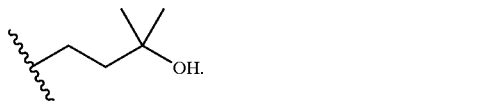

8. The compound of claim 7 selected from the group consisting of:

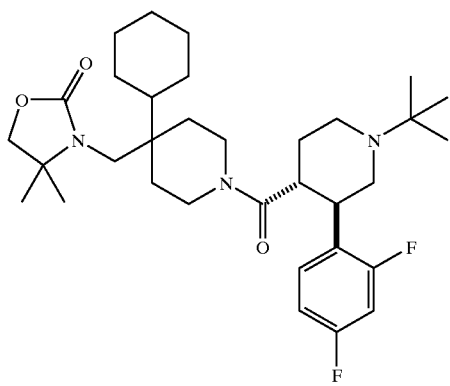

-continued

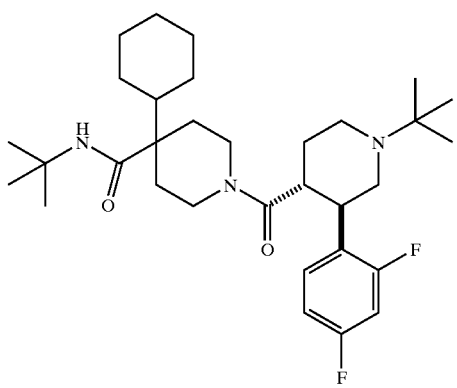

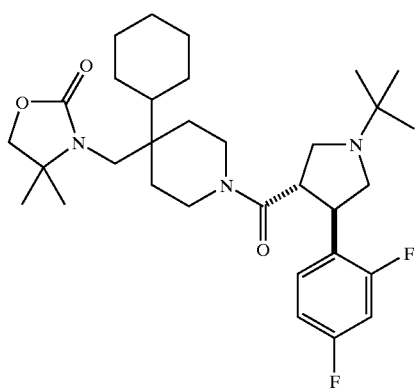

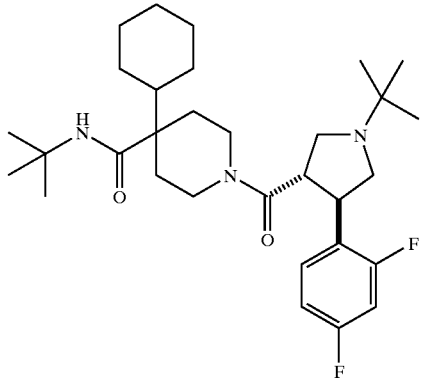

-continued
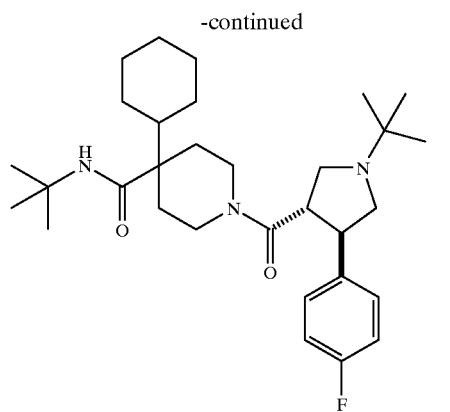
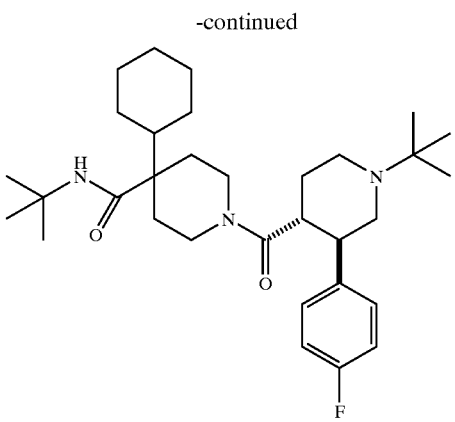
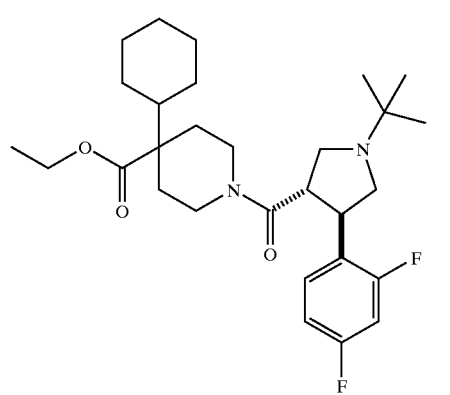
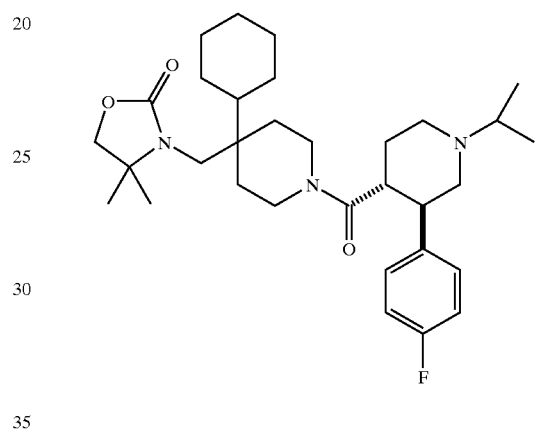
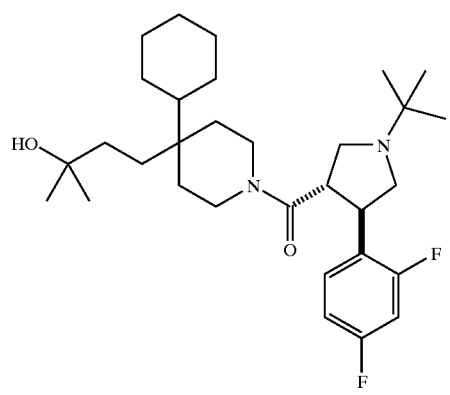
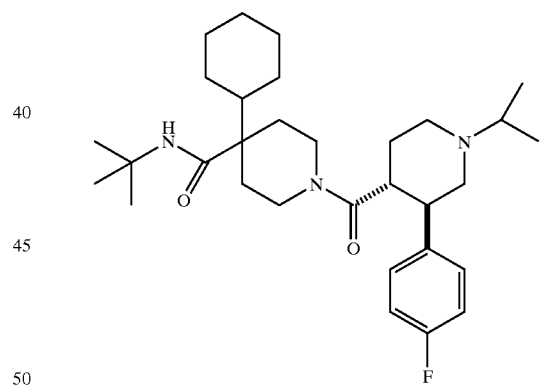
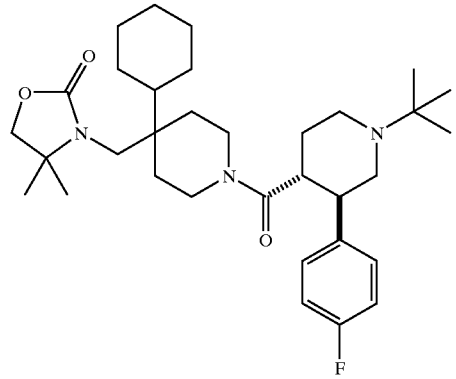
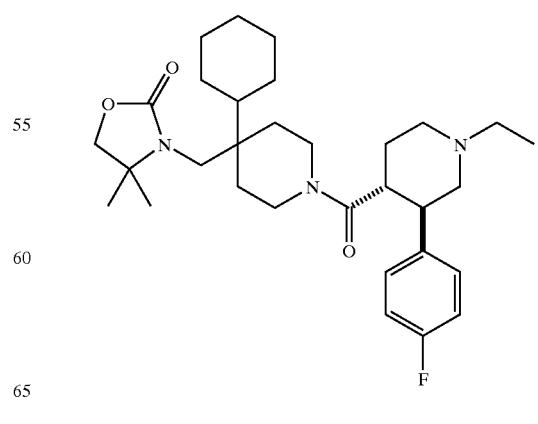

123
-continued
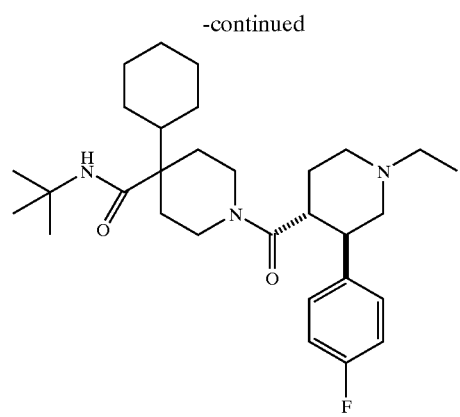
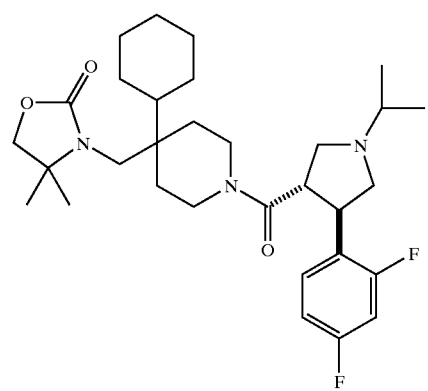
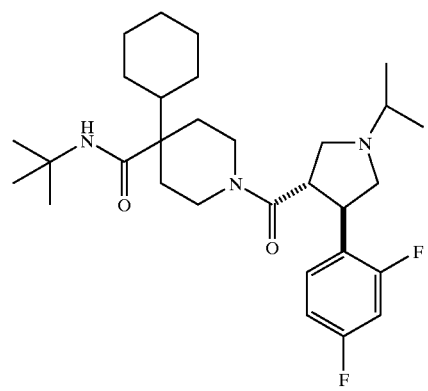
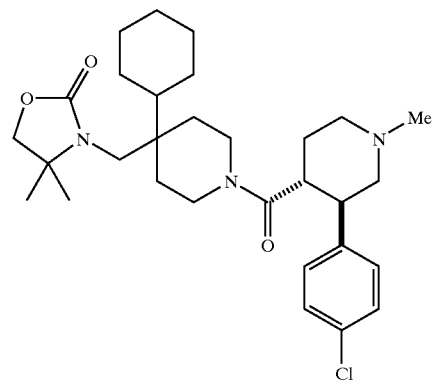
124
-continued
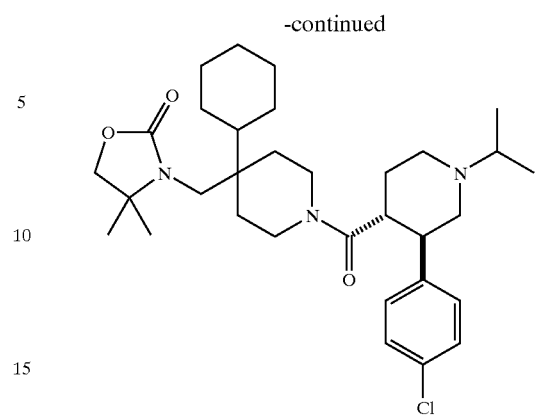
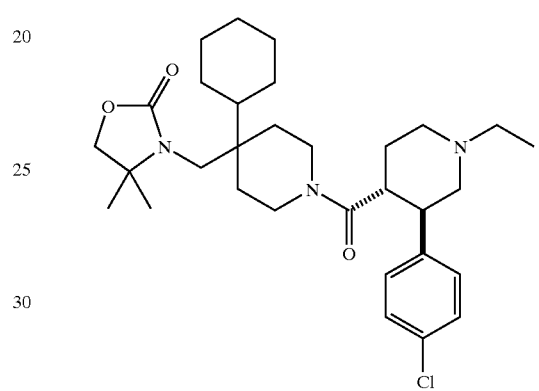
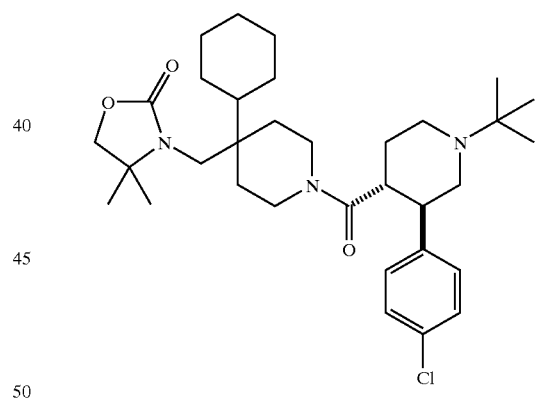
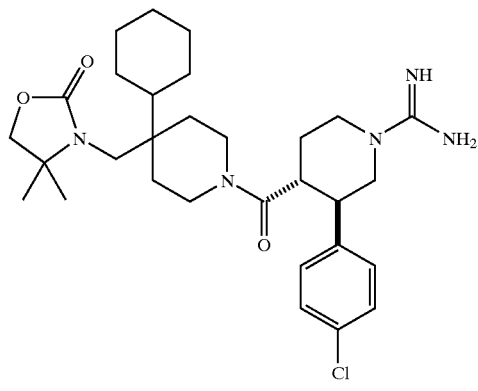

-continued

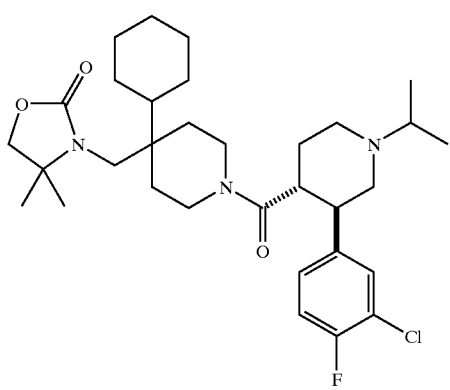

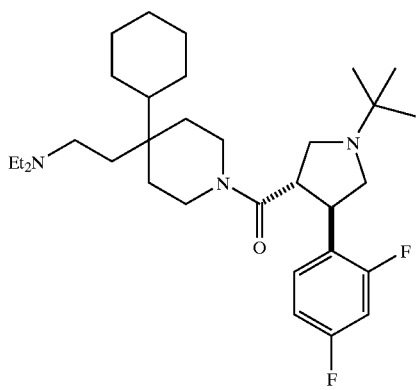

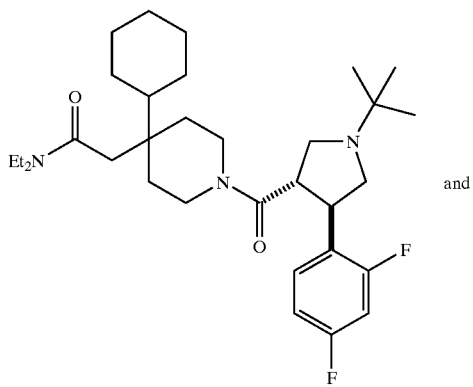

and

-continued

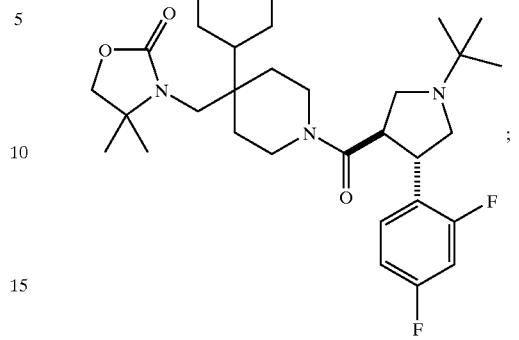

;

or a pharmaceutically acceptable salt thereof.

9. A pharmaceutical composition which comprises a therapeutically effective amount of a compound of claim 1 and a pharmaceutically acceptable carrier.

10. A method for the treatment of obesity in a subject in need thereof which comprises administering to the subject a therapeutically effective amount of a compound according to claim 1.

11. A method for the treatment of diabetes mellitus in a subject in need thereof comprising administering to the subject a therapeutically effective amount of a compound according to claim 1.

12. A method for the treatment of erectile dysfunction in a subject in need thereof comprising administering to the subject a therapeutically effective amount of a compound according to claim 1.

* * * * *